United States Patent [19]

Ellman

[11] Patent Number: 5,545,568

[45] Date of Patent: Aug. 13, 1996

[54] SOLID PHASE AND COMBINATORIAL SYNTHESIS OF COMPOUNDS ON A SOLID SUPPORT

[75] Inventor: Jonathan A. Ellman, Berkeley, Calif.

[73] Assignee: The Regents of the University of California, Oakland, Calif.

[21] Appl. No.: 161,677

[22] Filed: Dec. 2, 1993

Related U.S. Application Data

[63] Continuation-in-part of Ser. No. 944,469, Sep. 14, 1992, Pat. No. 5,288,514.

[51] Int. Cl.$^6$ .................................................. G01N 33/543
[52] U.S. Cl. ...................... 436/518; 436/501; 436/531; 435/7.1; 427/2.1; 427/2.13; 427/2.11; 427/2.23
[58] Field of Search .................................. 427/2.1, 2.13, 427/2.11, 2.12, 2.23; 436/518, 531, 501; 435/7.1

[56] References Cited

U.S. PATENT DOCUMENTS

| | | | |
|---|---|---|---|
| 3,297,755 | 1/1967 | Sternbach et al. | 260/566 |
| 4,758,623 | 7/1988 | Leznoff | 325/54.11 |
| 4,968,794 | 11/1990 | Weber et al. | 514/220 |
| 5,082,839 | 1/1992 | Weber et al. | 514/220 |
| 5,143,854 | 9/1992 | Pirrung et al. | 436/518 |
| 5,288,514 | 2/1994 | Ellman | 427/2.1 |
| 5,324,483 | 6/1994 | Cody et al. | 422/131 |

OTHER PUBLICATIONS

Hökfelt, T., et al, "Distribution Patterns of CCK and CCK mRNA in some Neuronal and Non–Neuronal Tissues," *Neuropeptides*, 19:(Suppl.)31–43 (1991).

Woodruff, G. N., et al., "Functional Role of Brain CCK Receptors," *Neuropeptides*, 19:(Suppl.)45–56 (1991).

Chang, R. S. L., et al., "Biochemical and pharmacological characterization of an extremely potent and selective non-peptide cholecystokinin antagonist," *Proc. Natl. Acad. Sci. USA*, 83:4923–4926 (Jul. 1986).

Davis, R., et al., "A Convergent Total Synthesis of (+)-Prostaglandin $F_{2\alpha}$ Via Conjugate Addition and Regiospecific Enolate Trapping," *Org. Chem.*, 44(22):3755–3759 (1979).

Suzuki, M., et al., "The Three–Component Coupling Synthesis of Prostaglandins," *J. Am. Chem. Soc.*, 110:4718–4726 (1988).

Lu, Gui–shen, et al., "Improved Synthesis of 4–Alkoxybenzyl Alcohol Resin," *J. Org. Chem.*, 46:3433–3436 (1981).

Ball, J. B., et al., "Conformational Constraints: Nonpeptide β–Turn Mimics," *J. of Molecular Recognition*, 3(2):55–64 (1990).

Evans, D. A., et al., "The Total Syntheses of the Isodityrosine–Derived Cyclic Tripeptides OF4949–III and K–13. Determination of the Absolute Configuration of K–13," *J. Am. Chem. Soc.*, 111:1063–1072 (1989).

Crowley, J. I., et al., "Solid–Phase Organic Synthesis: Novelty or Fundamental Concept?," *Accounts of Chemical Research*, 9:135–144 (1976).

Rose, G. D., et al., "Turns in Peptides and Proteins," *Advances in Protein Chemistry*, 37:1–109 (1985).

Taylor, R. J. K., "Organocopper Conjugate Addition–Enolate Trapping Reactions," *Synthesis*, pp. 364–392 (Apr. 1985).

Worster, P. M., et al., "Asymmetric Synthesis of 2–Alkylcyclohexanones on Solid Phases," *Angew. Chem. Int. Ed. Engl.*, 18(3):221–222 (1979).

Kraus, M. A., et al., "The Directed Mixed Ester Condensation of Two Acids Bound to a Common Polymer Backbone," *J. of Amer. Chem. Soc.*, 93(26):7325–7327 (Dec. 29, 1971).

Kaplan, B. E., et al., "Photochemical Loss of a Chloride Anion from an α–Chloroketone. The Photolysis of Exo–3–Chlorobicyclo[2.2.1]Hept–5–En–2–One in Methanol," *Tetrahedron Letters*, No. 55, pp. 4855–4856 (1970).

Baum, R. M., "Combinatorial Approaches Provide Fresh Leads for Medicinal Chemistry," *C&EN*, pp. 20–26 (Feb. 7, 1994).

Fyles, T. M., et al., "Some Solid–Phase Syntheses of the Sex Attractant of the Spruce Budworm—trans–11–Tetradecenal," *J. Chem. Ecol.*, 4(1):109–116 (1978).

Svirskaya, P. I., et al., "Syntheses of Unconjugated (Z,Z)–Diolefinic Insect Pheromones on Insoluble Polymer Supports," *J. of Chem. Ecology*, 10(2):321–333 (1984).

Yedidia, V., et al., "Regioselectivity in cycloaddition reactions on solid phases," *Canadian J. Chem.*, 58(11):1144–1150 (1980).

Svirskaya, P. I., et al., "Syntheses of Trans Alken–1–ols as Candidates for Insect Sex Attracts," *J. of Chemical and Engineering Data*, 24(2):152–155 (1979).

Neckers, D. C., "Solid phase synthesis," *Chemtech*, pp. 108–116 (Feb. 1978).

Keana, J. F. W., et al., "Functionalized Silica Gel as a Support Solid–Phase Organic Synthesis," *J. of Organic Chemistry*, pp. 1641–1644 (May 16, 1986).

Leznoff, C. C., et al., "The use of polymer supports in organic synthesis. VIII. Solid phase syntheses of insect sex attractants," *Can. J. Chem.*, 55:1143–1153 (1977).

Goldwasser, J. M., et al., "The solid phase synthesis of monoester monoamides and monoester monoalcohols from symmetrical diacid chlorides," *Can. J. Chem.*, 56:1562–1568 (1978).

Fyles, T. M., et al., "The use of polymer supports in organic synthesis. XII. The total stereoselective synthesis of *cis* insect sex attractants on solid phases," 55:4135–4143 (1977).

(List continued on next page.)

*Primary Examiner*—Robert T. Bond
*Attorney, Agent, or Firm*—Townsend and Townsend and Crew

[57] ABSTRACT

Methods, compositions, and devices for synthesizing combinatorial libraries of various useful compounds, such as benzodiazepines, prostaglandins, β-turn mimetics and glycerol-derived drugs is described. In order to expediently synthesize such combinatorial libraries of derivatives based upon these core structures, a general methodology for the solid phase synthesis of these derivatives is also provided. This disclosure thus also describes an important extension of solid phase synthesis methods to nonpolymeric organic compounds.

9 Claims, 4 Drawing Sheets

OTHER PUBLICATIONS

Leznoff, C. C., et al., "Festphasensynthese unsymmetrischer Tetraarylporphyrine," *Angew. Chem.*, 90(12):1001–1002 (1978).

Leznoff, C. C., et al., "Use of Insoluble Polymer Supports in Organic Synthesis. 9. Synthesis of Unsymmetrical Carotenoids on Solid Phases," *J. Org. Chem.*, 42(19):3203–3205 (1977).

Beebe, X., et al., "Polymer–Supported Synthesis of 2,5–Disubstituted Tetrahydrofurans," *J. Am. Chem. Soc.*, 114:10061–10062 (1992).

Sugasawa, T., et al., "1–Azacycloalkyl–1,4–benzodiazepin–2–ones with antianxiety–Antidepressant Actions," *J. Med. Chem.*, 28(6):699–707 (1985).

O'Donnell, M. J., et al., "A Mild and Efficient Route to Schiff Base derivatives of Amino Acids," *J. Org. Chem.*, 47:2663–2666 (1982).

Leznoff, C. C., et al., "Syntheses of Monometalated and Unsymmetrically Substituted Binuclear Phthalocyanines and a Pentanuclear Phtalocyanine by Solution and Polymer Support Methods," *J. Org. Chem.*, 56(1):82–90 (1991).

Fyles, T. M. et al., "The use of polymer supports in organic synthesis. V. The preparation of monoacetates of symmetrical diols," *Can. J. Chem.*, 54:935–942 (1976).

Leznoff, C. C., "Synthesis of Insect Sex Attractants on Solid Phases," *J.C.S. Chem. Comm.*, pp. 251–252 (1976).

McArthur, C. R., et al., "Polymer supported enantioselective reactions. II. α–Methylation of cyclohexanone," *Can. J. Chem.*, 60:1836–1841 (1982).

Leznoff, C. C., et al., "The Use of Insoluble Polymer Supports as Monoblocking Groups of Symmetrical Diacid Chlorides," *Tetrahedron Letters*, No. 22, pp. 1875–1878 (1977).

Dixit, D. M., et al., "Insoluble Polymer Supports as Monoblocking Agents of Symmetrical Diamines," *J.C.S. Chem. Comm.*, pp. 798–799 (1977).

Xu, Z., et al., "The monoblocking of symmetrical diketones on insoluble polymer supports," *Can. J. Chem.*, 61:1405–1409 (1983).

Schore, N. E., et al., "Pauson–Khand Cycloadditions on Polymer–Linked Substrates," *J. Am. Chem. Soc.*, 112:441–442 (1990).

Moon, H., et al., "A Polymer–Supported Chiral Auxiliary Applied to the Iodolactonization reaction: Preparation of γ–Butyrolactones," *J. Org. Chem.*, 57:6088–6089 (1992).

Leznoff, C. C., "The Use of Insoluble Polymer Supports in General Organic Synthesis," *Accounts of Chemical Research*, 11:327–333 (1978).

Zuckermann, R. N., et al., "Efficient Method for the Preparation of Peptoids [Oligo(N–substituted glycines)] by Submonomer Solid–Phase Synthesis," *J. Am. Chem. Soc.*, 114:10646–109647 (1992).

Baum, R., "Solid–phase synthesis of benzodiazepines," *C&EN*, pp. 33–34 (Jan. 18, 1993).

Hall, T. W., et al., "The Solid Phase Synthesis of Unsymmetrical Phthalocyanines," *Nouveau Journal De Chimie*, pp. 653–658 (1982).

Worster, P. M., et al., "Asymmetrische Synthese von 2–Alkylcyclohexanonen an festen Trägern," *Angew. Chem.*, 91(3):255 (1979).

Wong, J. Y., et al., "Festphasensynthese und Photochemie von 4,4'–Stilbendicarbaldehyd," *Angew. Chem.*, 86(20):743–744 (1974).

Kirk–Othmer, *Encyclopedia of Chem. Tech.*, 3rd Ed., vol. 18 (Wiley 1982).

Camps, F., "Organic syntheses with Functionalized polymers. IV. Synthesis of 1,3–dihydro–5–phenyl–2H–1,4–benzodiazepin–2–ones." *Chemical Abstracts*, No. 10018q, p. 841 (1975).

Bogatskii, A. V., et al., "1,4–Benzoidiazepines, their cyclic homologs and analogs. XVII. Synthesis and properties of 3–arylidene–and 3–heterylidene–1,2–dihydro–3H–1,4–benzodiazepin–2–ones," *Chemical Abstracts*, No. 10019r, p. 841 (1975).

DeWitt, S. H., et al., "'Diversomers': An Approach to nonpeptide, nonoligomeric chemical diversity," *Proc. Natl. Acad. Sci. USA*, 90:6909–6913 (Aug. 1993).

Jung, G., et al., "Multiple Peptide Synthesis Methods and their Applications," *Angew. Chem. Int. Ed. Engl.*, 31:367–383 (1992).

Evans, B. E., et al., "Methods for Drug Discovery: Development of Potent, Selective, Orally Effectie Cholecystokinin Antagonists," *J. Med. Chem.*, 31:2235–2246 (1988).

Sternbach, L. H., et al., "The Benzodiazepine Story," *J. of Med. Chem.*, 22(1):1–7 (Jan. 1979).

Baum, R. M., "Combinatorial Approaches Provide Fresh Leads for Medicinal Chemistry", *C&EN* pp. 20–26 (Feb. 1994).

Yankeelov, J. A., Jr., et al., "Peptide–Gap Inhibitors. Stereoselective synthesis of Enantiomeric Dipeptide Analogues of Glycylleucine Which Contain Methylene Thioether Groups Substituted for Peptide Linkages," *J. Org. Chem.*, 43(8):1623–1624 (1978).

Spatola, A. F., et al., "Pseudodipeptides: A Novel Route to Serine–Containing Diastereomeric Analogues," *J. Org. Chem.*, 46:2393–2394 (1981).

Felix, A. M., et al., "Applications of BOP reagent in solid phase synthesis," *Int. J. Peptide Protein Res.*, 31:231–238 (1988).

Felix, A. M., et al., "Synthesis, biological activity and conformational analysis of cyclic GRF analogs," *Int. J. Peptide Protein Res.*, 32:441–454 (1988).

Fodor, S. P. A., et al., "Light–Directed, Spatially Addressable Parallel Chemical Synthesis," *Science*, 251:767–773 (15 Feb. 1991).

Camps, F., et al., "Organic Syntheses with Functionalized Polymers: I. Preparation of Polymeric Substrates and Alkylation of Esters," *Tetrahedron Letters*, No. 20, pp. 1713–1714 (1971).

Camps, F., et al., "Organic Syntheses with Functionalized Polymers: II. Wittig Reaction with Polystyryl–p–Diphenylphosphoranes," *Tetrahedron Letters*, No. 20, pp. 1715–1716 (1971).

Bunin, B. A., et al., "A General and Expedient Method for the Solid–Phase Synthesis of 1,4–Benzodiazepine Derivatives," *J. Am. Chem. Soc.*, 1992(114):10997–10998.

Lam, K. S., et al., "A new type of synthetic peptide library for identifying ligand–binding activity," *Nature*, 354:82–84 (7 Nov. 1991).

Houghten, R. A., et al., "Generation and use of synthetic peptide combinatorial libraries for basic research and drug discovery," *Nature*, 354:84–86 (7 Nov. 1991).

Wetzel, R., "Learning from the immune system: laboratory methods for creating and refining molecular diversity in polypeptides," *Protein Engineering*, 4(4):371–374 (1991).

Evans, B. E., et al., "Design of potent, orally effective, nonpeptidal antagonists of the peptide hormone cholecystokinin," *Proc. Natl. Acad. Sci. USA*, 83:4918–4922 (Jul. 1986).

Römer, D., et al., "An opioid benzodiazepine," *Nature*, 298:759–760 (19 Aug. 1982).

Carpino, L. A., et al., "((9–Fluoroenylmethyl)osy)carbonyl (FMOC) amino Acid Fluorides. Convenient New Peptide Coupling Reagents Applicable to the FMOC/tert–Butyl Strategy for Solution and Solid–Phase Syntheses," *J. Am. Chem. Soc.*, 112:9651–9652 (1990).

Pauwels, R., et al., "Potent and selective inhibition of HIV–1 replication in vitro by a novel series of TIBO derivatives," *Nature*, 343:470–474 (1 Feb. 1990).

Frechet, J. M. J., "Synthesis and Applications of Organic Polymers as Supports and Protecting Groups," *Tetrahedron*, 37:663–683 (1981).

Hsu, Ming–Chu, et al., "Inhibition of HIV Replication in Acute and Chronic Infections in Vitro by a Tat Antagonist," *Science*, 254:1799–1802 (20 Dec. 1991).

Pirkle, W. H., et al., "Direct Liquid Chromatographic Separation of Benzodiazepinone Enantiomers," *J. of Chromatography*, 291:291–298 (1984).

Geysen, H. M., et al., "Strategies for epitope analysis using peptide synthesis," *J. of Immunological Methods*, 102:259–274 (1987).

Saragovi, H. U., et al, "Design and Synthesis of a Mimetic from an Antibody Complementarity–Determining Region," *Science*, 253:792–795 (16 Aug. 1991).

Spatola, A. F., et al, "Synthesis and Biological Activities of Pseudopeptide Analogues of LH–RH: Agonists and Antagonists," *Biochemical and Biophysical Research Communications*, 97(3):1014–1023 (Dec. 16, 1980).

SOLID PHASE AND COMBINATORIAL SYNTHESIS OF COMPOUNDS ON A SOLID SUPPORT

RELATION TO U.S. PATENT APPLICATION

This application is a continuation-in-part of U.S. patent application Ser. No. 07/944,469, filed Sep. 14, 1992, now U.S. Pat. No. 5,288,514.

FIELD OF THE INVENTION

The present invention relates to the field of solid phase chemistry. More specifically, in one embodiment the invention provides a method, device, and compositions for solid phase and combinatorial synthesis of diverse groups of organic compounds.

BACKGROUND OF THE INVENTION

Chemical methods have been developed recently for the synthesis of large combinatorial libraries of peptides and oligonucleotides that are later screened against a specific receptor or enzyme to determine the key molecular recognition elements of the compound for that receptor or enzyme. Unfortunately, peptides and oligonucleotides tend to have limited oral activities due to their large size and rapid clearing times resulting in part from their susceptibility to enzymatic degradation. Therefore, such materials tend to have limited utility as therapeutic agents. In such cases it would be beneficial to have access to small molecules which have inherently greater oral activities and are resistant to enzymatic attack.

Virtually any biologically active organic compound can be accessed by chemical synthesis; however, such organic compounds are still synthesized and evaluated one at a time in many cases. This limitation is especially severe when the magnitude of the challenge of finding a biologically active compound is considered. A recent report concluded that, on average, over 10,000 compounds must be screened before one biologically active compound is discovered. *Science*, Vol. 259 p. 1564 (Mar. 12, 1993). This limitation could be overcome by developing a methodology for the combinatorial synthesis of large numbers of derivatives of therapeutically important classes of organic compounds. Screening these compounds against key receptors or enzymes would then greatly accelerate the acquisition of useful structure versus recognition data and would revolutionize the search for potent new therapeutic agents.

From the above it is seen that improved methods, compositions, and devices for synthesis of therapeutically useful compounds are desired.

SUMMARY OF THE INVENTION

Improved methods, compositions, and devices for synthesis of therapeutically useful compounds are provided by virtue of the present invention. The invention provides a rapid approach for combinatorial synthesis and screening of libraries of derivatives of organic compounds. Included in the present invention are three therapeutically important classes of compounds in specific embodiments; benzodiazepines, prostaglandins, β-turn mimetics. A fourth class of compounds, glycerol derivatives, provide an important avenue to the synthesis of a wide variety of important chemicals and pharmaceuticals.

In order to expediently synthesize a combinatorial library of derivatives based upon these monomeric organic compounds, a general methodology for the solid phase synthesis of these derivatives is provided. When synthesis on solid support proceeds according to preferred aspects of the present invention, purification and isolation steps can be eliminated; thus dramatically increasing synthesis efficiency. This patent disclosure thus also describes an important extension of solid phase synthesis methods to nonpolymeric organic compounds.

In one embodiment of the invention, a method is provided for the formation of a library of monomeric compounds having a plurality of chemical structures on a solid substrate, the method comprising the steps of binding non-α-amino acid monomers to a solid substrate and reacting said monomers with a plurality of reagents under conditions effective to create a plurality of chemical structures.

In preferred embodiment, the reacting of non-γ-amino acid monomers with reagents comprises exposing the monomers to the reagents simultaneously.

In another preferred embodiment, the library created by the method of the invention is screened against a receptor to determine which of the compounds are ligands for the receptor.

In still another preferred embodiment, the present invention includes a kit comprising at least 50 different compounds, chosen from the group consisting of benzodiazepines, β-turn mimetics, prostaglandins and glycerol derivatives, and having biological activity, which are bound to a solid support.

A further understanding of the nature and advantages of the inventions herein may be realized by reference to the remaining portions of the specification and the attached drawings.

DESCRIPTION OF THE PREFERRED EMBODIMENTS

Contents

Figure 1:
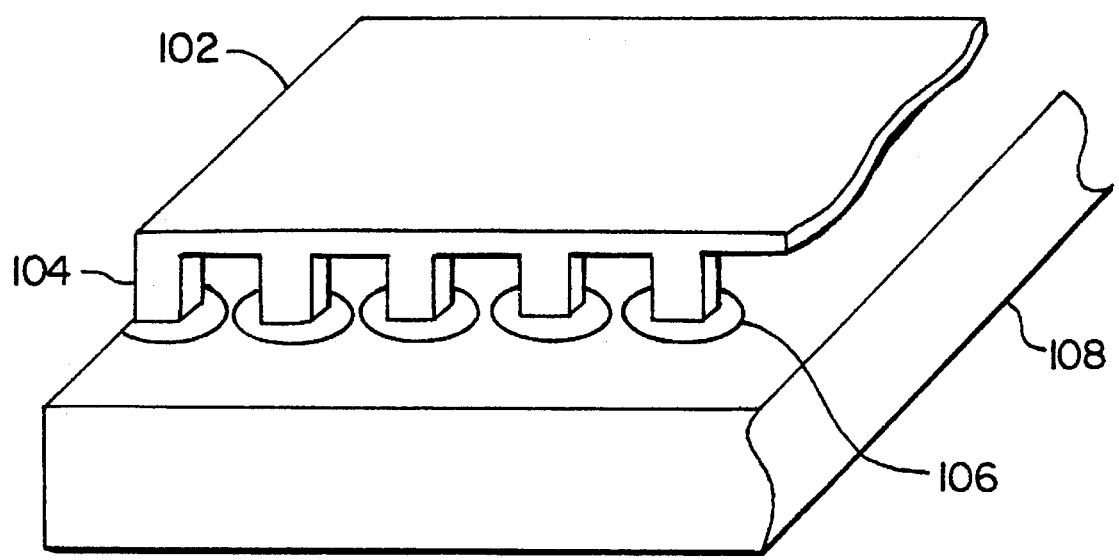
FIG. 1 is an illustration of pin based synthesis techniques.

I. General
  A. Terminology
  B. Overall Description of the Invention
II. Benzodiazepines
  A. Description
  B. Examples
III. Prostaglandins
  A. Description
  B. Formation of Compounds of Scheme I
  C. Pin-based Combinatorial Synthesis
IV. β-Turn Mimetics
  A. Description
  B. Examples
V. Glycerol Derivatives
  A. Description
  B. Examples
VI. Methods of Forming Libraries of Monomers
VII. Screening VIII. Conclusion I. General A. Terminology The following terms are intended to have the following general meanings:

1. Complementary: Refers to the topological compatibility or matching together of interacting surfaces of a ligand molecule and its receptor. Thus, the receptor and its ligand can be described as complementary, and furthermore, the contact surface characteristics are complementary to each other.

2. Ligand: A ligand is a molecule that is recognized by a particular receptor. Examples of ligands that can be investigated by this invention include, but are not restricted to, agonists and antagonists for cell membrane receptors, toxins and venoms, viral epitopes, hormones (e.g., opiates, steroids, etc.), hormone receptors, peptides, enzymes, enzyme substrates, cofactors, drugs, lectins, sugars, oligonucleotides (such as in hybridization studies), nucleic acids, oligosaccharides, proteins, and monoclonal antibodies.

3. Benzodiazepines: A seven-membered organic ring with two nitrogens in the ring, normally with nitrogens at positions 1 and 4, often with an aromatic ring attached to the seven-membered ring, normally at positions 6 and 7. Benzodiazepines include compounds having a 5-phenyl-3H-1,4-benzodiazepin-2-(1H)-one nucleus, including those with substitutions at the 1-, 3-, 5- and 6- through 9-positions. Many of these compounds will have a phenyl ring at the 5-position, thereby resulting in two phenyl rings in the structure, both optionally substituted.

4. Prostaglandins: A cyclo-pentane core structure with appropriate functional groups, normally including hydroxy groups, oxo groups and/or alkyl groups extending from the ring, that produces a biological response. Prostaglandins include compounds having a 3-hydroxy-5-oxocyclopentane nucleus with variable alkyl chains, including substituted alkyls, at the 2- and 3-positions.

5. β-Turn: β-turns are normally described as a reverse in the direction of a peptide chain which takes place over about four amino acid residues. β-turn mimetics are small to medium size cyclic ring structures that mimic the structure of the β-turn. β-turn mimetics include compounds having structures which mimic β-turns in protein structures. The compounds are generally short chains of α-amino acids with variations in the side chains and substitutions in the peptide bonds.

6. Radiation: Energy which may be selectively applied including energy having a wavelength of between $10^{-14}$ and $10^4$ meters including, for example, electron beam radiation, gamma radiation, x-ray radiation, light such as ultra-violet light, visible light, and infrared light, microwave radiation, and radio waves. "Irradiation" refers to the application of radiation to a surface.

7. Receptor: A molecule that has an affinity for a given ligand. Receptors may be naturally-occurring or synthetic molecules. Also, they can be employed in their unaltered state or as aggregates with other species. Receptors may be attached, covalently or non-covalently, to a binding member, either directly or via a specific binding substance. Examples of receptors which can be employed by this invention include, but are not restricted to, antibodies, cell membrane receptors, monoclonal antibodies and antisera reactive with specific antigenic determinants (such as on viruses, cells, or other materials), drugs, oligonucleotides, polynucleotides, nucleic acids, peptides, cofactors, lectins, sugars, polysaccharides, cells, cellular membranes, and organelles. Receptors are sometimes referred to in the art as anti-ligands. As the term receptors is used herein, no difference in meaning is intended. A "Ligand Receptor Pair" is formed when two macromolecules have combined through molecular recognition to form a complex. Other examples of receptors which can be investigated by this invention include but are not restricted to microorganism receptors, enzymes, catalytic polypeptides, hormone receptors, and opiate receptors.

8. Substrate: A material having a rigid or semi-rigid surface, generally insoluble in a solvent of interest such as water. In some embodiments, at least one surface of the substrate will be substantially flat, although in some embodiments it may be desirable to physically separate synthesis regions for different polymers with, for example, wells, raised regions, etched trenches, or the like. According to other embodiments, small beads may be provided on the surface which may be released upon completion of the synthesis, or individual beads may be used ab initio.

9. Protecting group: A material which is chemically bound to a monomer unit and which may be removed upon selective exposure to an activator such as a selected chemical activator such as an acidic or basic environment, or to another selected activator such as electromagnetic radiation and, especially light, such as ultraviolet and visible light. Examples of protecting groups with utility herein include those comprising fluorenylmethyloxycarbonyl, nitropiperonyl, pyrenylmethoxycarbonyl, nitroveratryl, nitrobenzyl, and other orthonitrobenzyl groups, dimethyl dimethoxybenzyl, 5-bromo-7-nitroindolinyl, o-hydroxy-α-methyl cinnamoyl, and 2-oxymethylene anthraquinone.

10. Predefined Region: A predefined region is a localized area on a surface which is, was, or is intended to be activated for formation of a polymer. The predefined region may have any convenient shape, e.g., circular, rectangular, elliptical, wedge-shaped, etc. For the sake of brevity herein, "predefined regions" are sometimes referred to simply as "regions." A predefined region may be illuminated in a single step, along with other regions of a substrate.

11. Substantially Pure: A molecule such as a benzodiazepine is considered to be "substantially pure" within a predefined region of a substrate when it exhibits characteristics that distinguish it from molecules in other predefined regions. Typically, purity will be measured in terms of biological activity or function as a result of uniform composition. Such characteristics will typically be measured by way of binding with a selected ligand or receptor. Preferably the region is sufficiently pure such that the predominant species in the predefined region is the desired molecule. According to preferred aspects of the invention, the molecules synthesized on the pin or other structure are 5% pure, more preferably more than 10% pure, preferably more than 20% pure, more preferably more than 80% pure, more preferably more than 90% pure, more preferably more than 95% pure, where purity for this purpose refers to the ratio of the number of desired ligand molecules formed in a predefined region to the total number of molecules formed in the predefined region.

12. Activator: A material or energy source adapted to render a group active and which is directed from a source to a predefined location on a substrate, such as radiation. A primary illustration of an activator is light such as visible, ultraviolet or infrared light. Other examples of activators include ion beams, electric fields, magnetic fields, electron beams, x-ray, and the like.

13. Combinatorial Synthesis Strategy: An ordered strategy for parallel synthesis of diverse polymer sequences by sequential addition of reagents and which may normally be represented by a reactant matrix, and a switch matrix, the product of which is a product matrix. A reactant matrix is a 1 column by m row matrix of the building blocks to be added. The switch matrix is all or a subset of the binary numbers, preferably ordered, between 1 and m arranged in columns. A "binary strategy" is one in which at least two successive steps illuminate a portion, often half, of a region of interest on the substrate. In a binary synthesis strategy, all possible compounds which can be formed from an ordered set of reactants are formed. In most preferred embodiments, binary synthesis refers to a synthesis strategy which also factors a previous addition step. For example, a strategy in which a switch matrix for a masking strategy halves regions that were previously illuminated, illuminating about half of the previously illuminated region and protecting the remaining half (while also protecting about half of previously protected regions and illuminating about half of previously protected regions). It will be recognized that binary rounds may be interspersed with non-binary rounds and that only a portion of a substrate may be subjected to a binary scheme. A combinatorial "masking" strategy is a synthesis which uses light or other deprotecting or activating agents to remove protecting groups from materials for addition of other materials such as amino acids. In some embodiments, selected columns of the switch matrix are arranged in order of increasing binary numbers in the columns of the switch matrix. Such strategies and the representational notation therefor are discussed in Fodor et al., *Science* (1991) 251:767–773.

14. Linker: A molecule or group of molecules attached to a substrate and spacing a synthesized polymer from the substrate, such as for exposure/binding to a receptor.

15. Alkyl: A cyclic, branched, or straight-chain aliphatic group containing only carbon and hydrogen. This term is further exemplified by groups such as methyl, heptyl, —$(CH_2)_2$—, and adamantyl. Alkyl groups can either be unsubstituted or substituted with one or more non-interfering substituents, e.g., halogen, alkoxy, acyloxy, hydroxy, mercapto, carboxy, benzyloxy, phenyl, or benzyl, each optionally substituted with additional non-interfering substituents, The term "non-interfering" characterizes the substituents as not adversely affecting any reactions to be performed in accordance with the process of this invention.

16. Lower alkyl: An alkyl group of one to six carbon atoms. Lower alkyl groups include those exemplified by methyl, ethyl, n-propyl, i-propyl, n-butyl, t-butyl, i-butyl (2-methylpropyl), cyclopropylmethyl, i-amyl, n-amyl and hexyl. Preferred lower alkyls are methyl and ethyl. If more than one alkyl group is present in a given molecule, each may be independently selected from "lower alkyl" unless otherwise stated.

17. Aryl: A monovalent unsaturated aromatic carbocyclic group having a single ring (e.g., phenyl) or multiple condensed rings (e.g., naphthyl or anthryl), which can optionally be unsubstituted or substituted with hydroxy, lower alkyl, alkoxy, chloro, halo, mercapto, and other non-interfering substituents.

18. Heteroaryl or HetAr: A monovalent unsaturated aromatic carbocyclic group having a singly ring (e.g., pyridyl or furyl) or multiple condensed rings (e.g., indolizinyl or benzo[b]thienyl) and having at least one hetero atom, such as N, O or S, within the ring, which can optionally be unsubstituted or substituted with hydroxy, alkyl, alkoxy, halo, mercapto, and other non-interfering substituents.

19. Arylalkyl: The groups —R"—Ar and —R"—HetAr, where Ar is an aryl group, HetAr is a heteroaryl group, and R" is straight-chain or branched-chain aliphatic group. Examples of arylalkyl groups include the sidechains of the amino acids phenylalanine and tryptophan.

20. Carboxyalkyl refers to the group —C(O)—R", where R" is lower alkyl.

21. Acyloxy refers to the group —OC(O)R", where R" is alkyl.

22. Abbreviations: The following frequently used abbreviations are intended to have the following meanings:
BOC: t-butoxycarbonyl.
BOP: benzotriazol-1-yloxytris-(dimethylamino)-phosphonium hexafluorophosphate.
DCM: dichloromethane; methylene chloride.
DMF: dimethyl formamide.
Fmoc: fluorenylmethyloxycarbonyl.
NV: nitroveratryl.
NVOC: 6-nitroveratryloxycarbonyl.
P: solid support structure
THF: tetrahydrofuran.
HMPA: 2-(4-hydroxymethylphenoxy)acetate.

23. Monomer: A molecule which is not substantially comprised of repeating molecular subunits. See, *Kirk-Othmer Encyclopedia of Chemical Technology* 3rd ed., Vol. 18, page 745 (Wiley 1983), the entire disclosure of which is incorporated herein by reference.

B. Overall Description of the Invention

The invention provides novel approaches for the combinatorial synthesis and screening of libraries of derivatives of therapeutically important classes of compounds including 1,4-benzodiazepines, prostaglandins, β-turn mimetics and glycerol library of derivatives based upon these core structures, generalized methodologies for the solid phase synthesis of these derivatives are also provided. In another aspect of the present invention, a method of synthesizing combinatorial libraries of compounds on a solid support that proceeds in sufficiently high yield in preferred embodiments such that purification and isolation steps can be eliminated thus dramatically increasing synthesis efficiency is described.

II. Benzodiazepines

A. Description

One application of the present invention is the preparation and screening, preferably in parallel and simultaneous fashion, of large numbers of benzodiazepine derivatives. Benzodiazepines are useful drugs for the targeting of enzymes, regulatory proteins and receptors of various kinds, and a variety of benzodiazepines, as well as their binding affinities, are known. Many more benzodiazepine structures may be postulated, however, and considered as potential active drugs for the same target species, and benzodiazepines as well as other drugs which target other enzymes, regulatory proteins and receptors are often sought.

To achieve the preparation and screening of large numbers of compounds that have benzodiazepine structures, the present invention provides solid-phase synthesis methods for benzodiazepines in which variable substituent groups are attached to a common central benzodiazepine structure. In one aspect of the solid-phase synthesis methods of the invention, a benzodiazepine precursor which contains a phenyl ring of the benzodiazepine without the closed heterocyclic ring is bonded to a solid support through a linkage on the phenyl ring. Either phenyl ring of the benzophenone system may be bonded to the solid support. Once the precursor is bonded to the solid support, a series of reactions is performed by contacting the solid support with a series of liquid-phase reagents. These reactions include closure of the heterocyclic ring and derivatization of the compound at various locations on the rings or other reactive sites on the compound structure. Appropriate protecting group(s) are attached to the precursor prior to the reaction with the solid support and to various sites on the molecule and the reagents to ensure that the desired reaction in each case occurs at the desired location on the structure.

This solid-phase synthesis permits each reaction to be confined to the surface area of a small solid structure. The physical joining of a multitude of small solid structures into a single unit, for example, then permits the simultaneous handling of a multitude of compounds and reagents. The use of structures of this kind for certain multiple simultaneous reactions is known in the art, and its application to the present invention will become apparent from the description which follows.

An overall illustration of a method for the solid-phase synthesis of benzodiazepines is shown in Reaction Scheme I.

B. Compounds of Scheme I

1. Preparation of Compounds of Formula 1

The starting material 1 is a 2-aminobenzophenone bearing substituents $R^A$ on one phenyl ring and $R^{A'}$ on the other, and in which the amino group bears the protecting group Fmoc. Those skilled in the art will appreciate that any of the wide variety of available amino protecting groups may be used in place of Fmoc, and that the choice of a particular protecting group will depend on the specific nature of the substituents and reactions contemplated. Also, more than one type of protecting may be included at any given point in the synthesis. See, e.g., Green, T., and Wuts, P. G. M., PROTECTIVE GROUPS IN ORGANIC SYNTHESIS $2^{ND}$ ED., Wiley, 1991, which is incorporated herein by reference. In addition, it will be recognized that a wide variety of ring systems may be used with this technique, including, inter alia and/or combinations of five- and six-membered rings, rings containing heteroatoms, varying degrees of saturation, and fused rings systems.

Moreover, the above-described amine moiety may itself be derived from the transformation of other functional groups, e.g., the reduction of a 2-nitrobenzophenone to form 2-aminobenzophenone. Functional groups which may be converted into amines include nitro, halogen, hydroxyl, azide, —$SO_2R$, —OR, —SR, and —N=NAr where R is alkyl and Ar is aromatic. See, e.g., March, ADVANCED ORGANIC CHEMISTRY $4^{TH}$ ED., Wiley, 1991, which is incorporated herein by reference. It will be apparent to those skilled in the art that this offers great flexibility in adding substituents to the phenyl rings (described below) since the various directing effects of the above-listed substituents may be employed to achieve a desired result (see, e.g., March). Therefore, many routes are available to synthesizing the substituted 2-aminobenzophenones 1.

REACTION SCHEME I

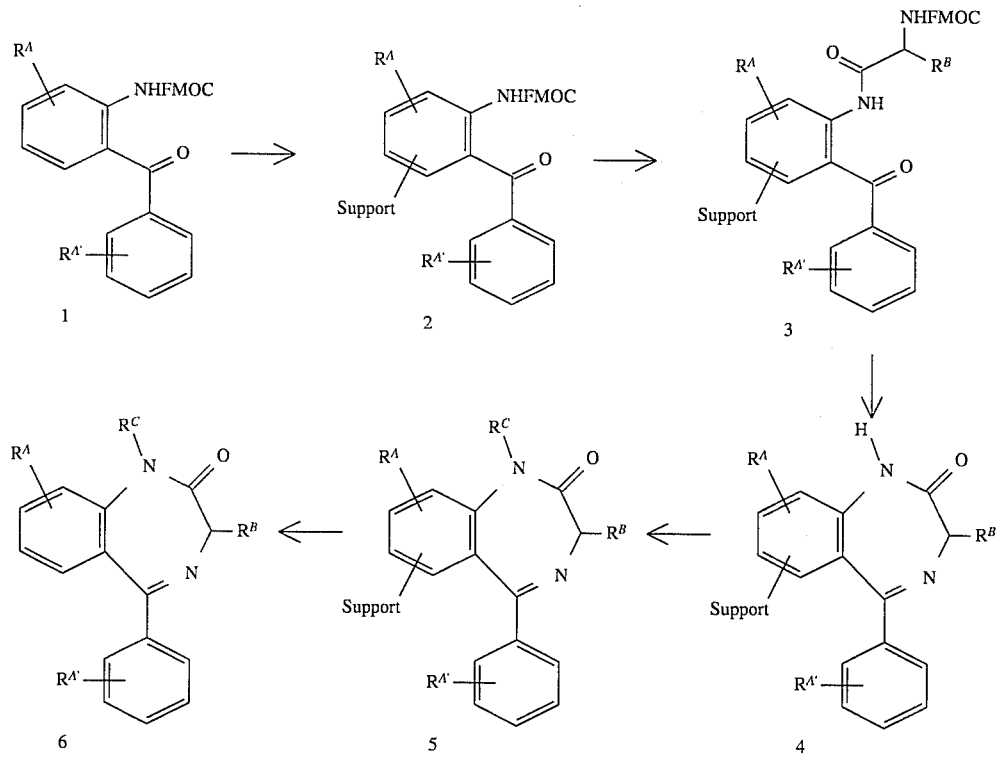

The $R^A$ and $R^{A'}$ substituents may be varied widely in both their identity and the positions which they occupy on the phenyl rings, and can thus be studied as variables for the screening which is performed subsequent to the synthesis.

examples are 2-(4-hydroxymethyl phenoxy) acetic acid (HMPA) and allyl 2-(4-bromomethyl phenoxy) acetate, and various analogs and derivatives of these compounds. Reaction Scheme II is an illustration of this type of coupling:

REACTION SCHEME II

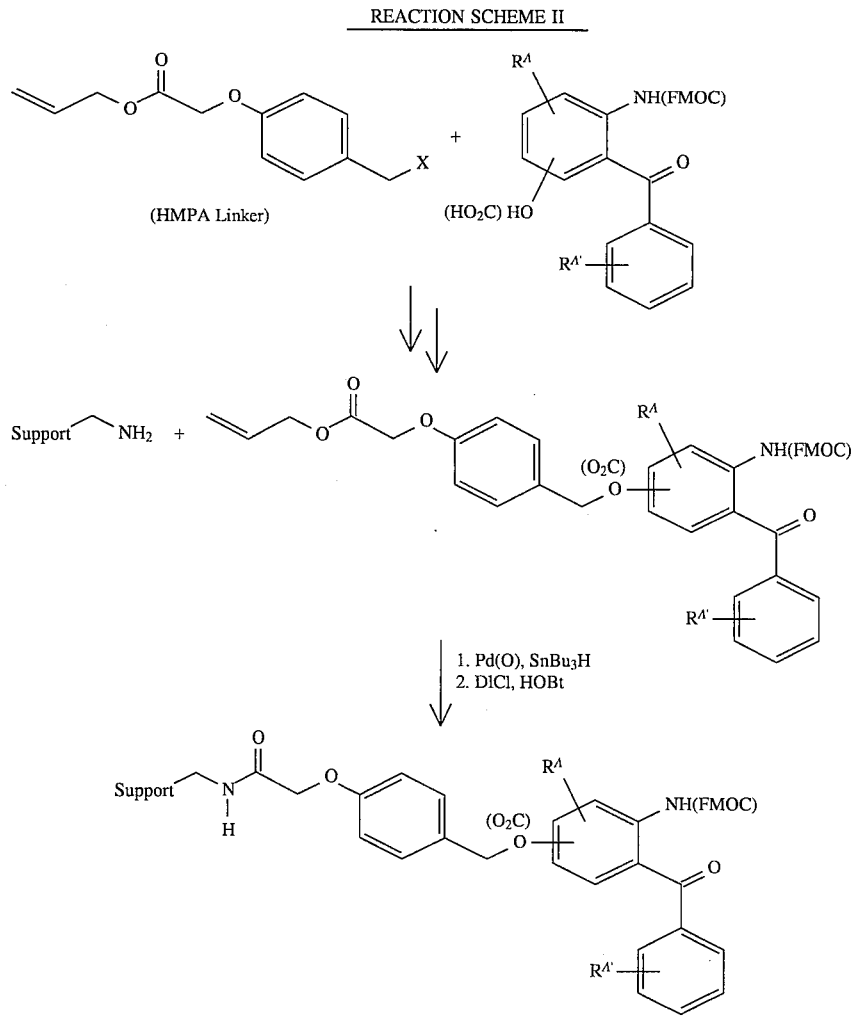

For example, $R^A$ and $R^{A'}$ may be selected independently from the group consisting of alkyl, aryl, arylalkyl, heteroaryl, halogen, carboxyalkyl, acyloxy, thioalkyl, phosphoroalkyl, carboxamide, trifluroracetyl or cyano. Those having skill in the art will appreciate that the methods for forming the substituted phenyl rings of 1 will are well-known. See, e.g., March. Some of these substituents will be inert to reagents which are used in the succeeding steps of the synthesis for activation or derivatization of the compound at other sites on the structure, while other substituents will be susceptible to the action of such reagents or by use of appropriate protecting groups. This type of susceptibility can be avoided by the appropriate selection of less active reagents. This will be explained in more detail below.

2. Preparation of Compounds of Formula 2

The substituted 2-aminobenzophenone 1 is coupled to the solid support, preferably by a clearable linker such as an acid-clearable linker, thereby forming a support-bound substituted 2-aminobenzophenone 2. A wide variety of acid-cleavable linkers are known among those skilled in the art, as described by Atherton et al., *J. Chem. Soc. Perkin I* (1981) 238–546, incorporated herein by reference. Prominent Once the coupling is achieved, the Fmoc protecting group is removed by conventional means, leaving an amine group.

A specific example is shown in Reaction Scheme III below. 2-amino-5-chloro-4'-hydroxybenzophenone 21 is reacted with allyl (2-bromomethylphenoxy)acetate 22 and KHMDS in dimethylformamide solution to form compound 23. The amine is then protected as the Fmoc derivative by the reaction of 23 with FmocCl and pyridine in THF solution. The allyl group is removed using Pd(0) and $Bu_3SnH$ to form 24. These procedures are known in the art (see March, Greene). It will also be appreciated that other protecting groups for the amine may be employed (see Greene). Finally, the carboxyl group of the linker is attached to a free amino group of the support with HOBt and diisopropylcarbodiimide (DICI) to form support-bound, Fmoc-protected aminobenzophnone 25. These procedures are also known in the art. See the Examples below for details.

Reaction Scheme III

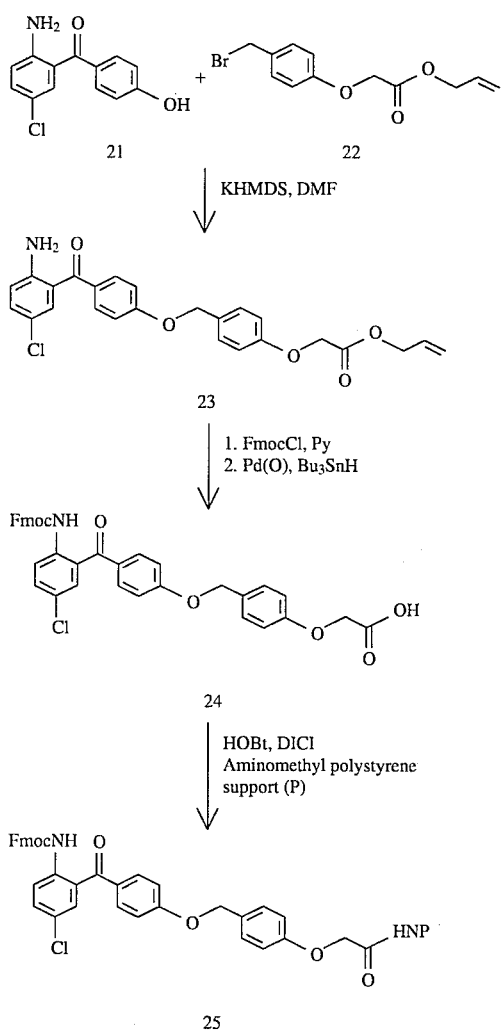

REACTION SCHEME IV

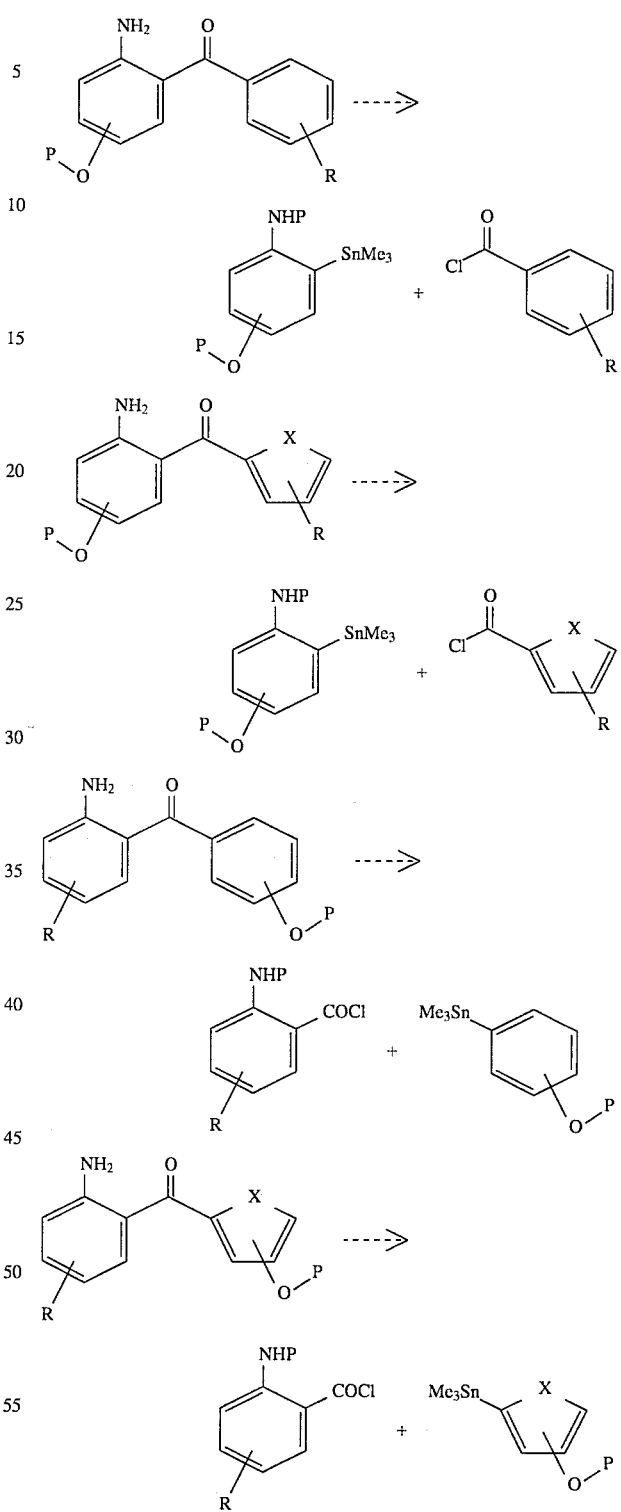

In another aspect, the invention provides a second, more flexible method for forming support-bound benzophenones as illustrated generally in Reaction Scheme IV. This second route employs the well-known Stille reaction for synthesizing aryl ketones (see, Milstein, D., Stille, J. K., *J. Org. Chem.*, 1979, 44, 1613–1618, which is incorporated herein by reference). The Stille reaction allows for the construction of the benzophenone portion of the benzodiazapine on the solid support, in contrast to the method outlined in Reaction Scheme III, where the benzophenone precursor must be synthesized separately.

As Reaction Scheme IV illustrates generally, the desired ketone may be accessed from a support-bound, substituted aryltrimethyltin compound and a substituted aryl chloride. These groups may include the range of substituents described above. Therefore, the number of available permutations accessible by solid-phase synthesis techniques using the Stille reaction is far greater than through the more conventional methods described above. In addition, it will be recognized that a wide variety of ring systems may be used with this technique, including, inter alia and/or combinations of five- and six-membered rings, rings containing heteroatoms (e.g., X=N, O, S), varying degrees of saturation, and fused rings systems.

A major advantage with the strategy outlined in Scheme IV is that more than one hundred aryl chlorides are available commercially (from, e.g., Aldrich or Sigma) and many more can by synthesized using techniques which are well known in the art (see, e.g., March). Thus, it will be appreciated that the use of the Stille reaction in concert with the methods of the invention will provide for still greater flexibility and scope in synthesizing efficiently large numbers of related compounds.

However, if the Stille method is employed the linker should not be an allyl ester (for example, compound 22 of Reaction Scheme III) as the use of Pd(0) with Bu₃SnH to remove the allyl group also destannylates rapidly the aryltrimethyltin compound. To avoid this problem, the carboxylic acid of compound 22 may be protected as the methyl ester 31 as shown in Reaction Scheme V. The reactions shown therein are well-known to those skilled in the art (see March). Of course, the coupling of the ester to the solid support can be performed as described above, as there is no destannylation side-reaction to consider.

The desired arylstannanes may be formed readily using techniques well-known in the art (see Stille, March). One example is illustrated in Reaction Scheme VI below. There 3-nitrophenol 41 is brominated to give 3-nitro-4-bromophenol 42. The free phenol hydroxyl is protected with Tips-Cl (triisopropylsilyl chloride) and the resulting silyl ether 43 is stannylated with hexamethylditin to form 44. Reaction of 44 with sodium hydroxide in dioxane/water regenerates the free hydroxyl 45, and this is reacted with KN(SiCH₃)₂ and linker 31 to form ether 46. Removal of the ester followed with the coupling of the linker to the support under the conditions described in Reaction Scheme III affords the bound stannane. The coupling of the free acid to the support should immediately follow the saponification of ester 46, as the free acid is not stable for prolonged periods. Again, these procedures are well known in the art.

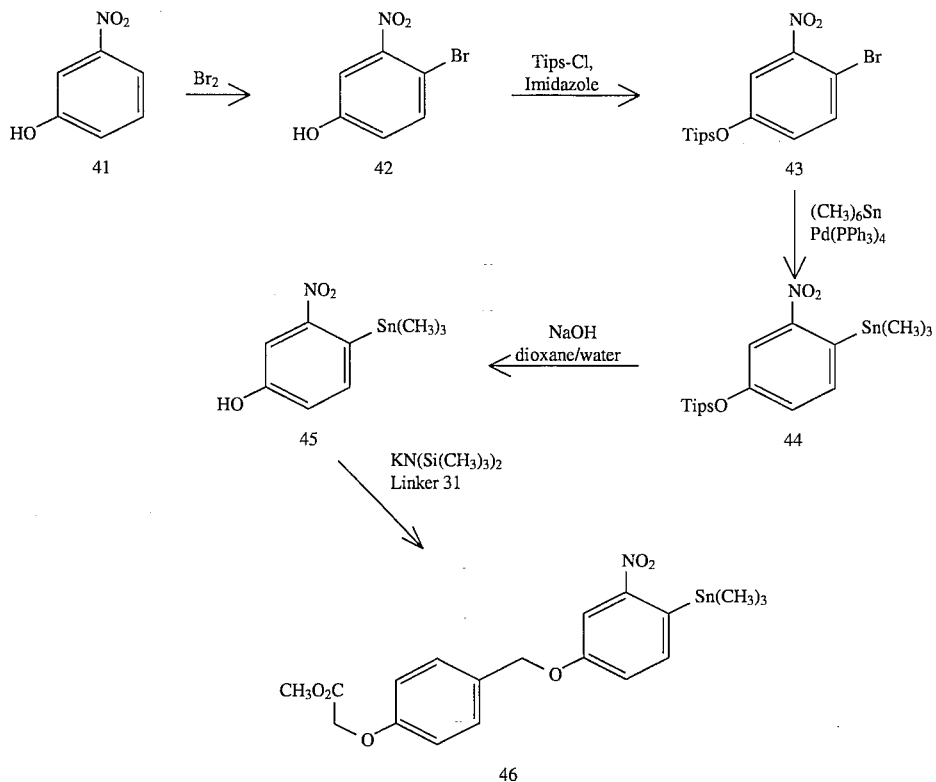

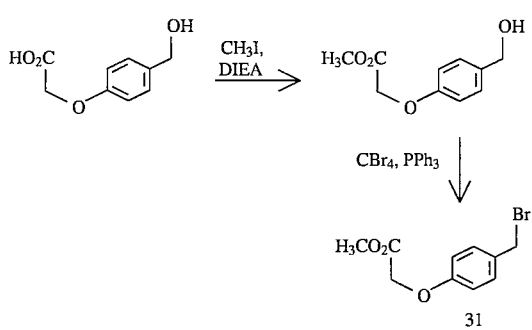

Having formed the desired bound aryltrimethyltin 46, the final steps to finishing the aminobenzophenone synthesis are performed as shown in Reaction Scheme VII (the linker is denoted as P). Support-bound compound 51 is reacted with benzoyl chloride, and acid scavenger such as diisopropylethylamine (DIEA) and a catalytic amount of bis-(dibenzylidineacetone)palladium to give the nitrobenzophenone 52. The nitro group is then reduced using any one of several well-known methods (see March). The resulting aminobenzophenone 53 is ready for further derivitization as described below. It will be appreciated that where the benzoyl chloride is bound to the substrate, the sequence of reactions will remain the same, the only change being the addition of the aryltrimethyl stannane to the bound benzoyl chloride.

REACTION SCHEME VII

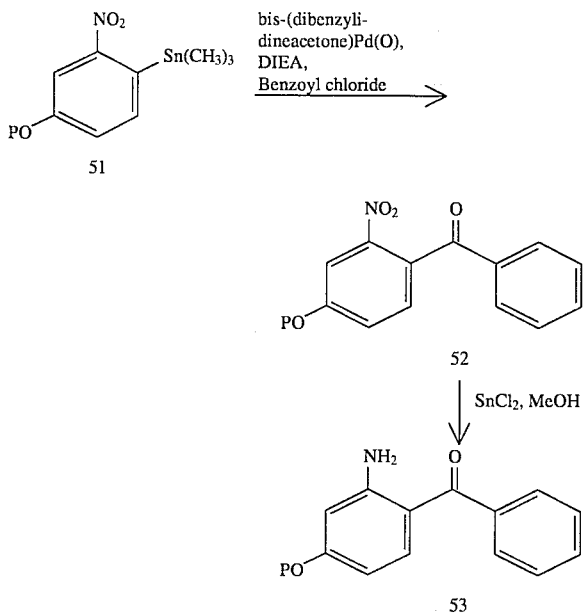

The above-described coupling between aryltin and benzoyl halides to form benzophenones may be performed using organometallic compounds other than aryltins such as 45. Couplings between benzoyl halides and organomanganese compounds, organothalliums, lithium trialkylarylborates, bis(triphenylphosphine)arylrhodium(I) compounds $(Rh(I)R(CO)(Ph_3P)_2$, where R is aryl), and arylmagnesium halides may be used as well. See, e.g., March pp. 487–488. In addition, the benzoyl halide reagents described above may be substituted with aryl anhydrides, esters, or amides if aryllithium reagents are used instead of aryltins. See, e.g., March pp. 488–489. Finally, Reaction Schemes VI and VII illustrate that the amine moiety of the 2-aminobenzophenone need not be supplied by a protected amine directly. Many other groups may be located adjacent the aryl halide or organometallic group of the phenyl ring which are easily converted to amines. Such groups include nitro, halogen, hydroxyl, azide, —$SO_2R$, —OR, —SR, and —N═NAr where R is alkyl and Ar is aromatic (see March). It will be apparent to those skilled in the art that this offers great flexibility in adding substituents to the phenyl rings since the various directing effects of the above-listed substituents may be employed to achieve a desired result (see, e.g., March). Therefore, many routes are available to synthesizing the substituted 2-aminobenzophenones.

One preferred organometallic coupling involving compounds other than aryltins employs the well-known Suzuki reaction (*Pure and Applied Chemistry*, 63:419–422 (1991), incorporated herein by reference for all purposes). This reaction allows the conversion of aryl halides Ar—X to substituted aryl compounds Ar—R, where R is alkyl, aryl or alkenyl. Typically, an aryl bromide (X═Br) is reacted with a borane having the formula $BRZ_2$, where R is aryl, alkenyl or alkyl and Z is a group such as alkyoxy or alkyl, and a palladium metal catalyst to form the desired substituted aryl compound. It will be appreciated that employment of the Suzuki reaction allows an efficient entry to substrate-bound benzodiazepines of formula 2 wherein A' is alkyl, aryl or alkenyl.

Thus, it will be appreciated that the synthetic strategy outlined above with respect to the Stille reaction can be generalized to include those methods of forming benzodiazapines and/or their analogs using any appropriate organometallic synthetic routes. A first compound which may be aryl, heteroaryl, cycloalkyl, or substituted aryl, heteroaryl, cycloalkyl, and which includes a first substituent selected from the group consisting of acyl halide or organometallic, and a second substituent selected from the group consisting of protected amino, nitro, halogen, hydroxyl, azide, —$OSO_2R$, —OR, —SR, and —N═NAr where R is alkyl and Ar is aromatic, hydrogen, alkyl, aryl, heteroaryl, substituted alkyl, substituted aryl or substituted heteroaryl, is attached to a substrate. This attached derivative is then reacted with a second compound which may be aryl, heteroaryl, cycloalkyl, or substituted aryl, heteroaryl, cycloalkyl, and which also includes a first substituent selected from the group consisting of acyl halide or organometallic, and a second substituent which is also selected from the group consisting of substituted amino, nitro, halogen, hydroxyl, azide, —$OSO_2R$, —OR, —SR, and —N═NAr where R is alkyl and Ar is aromatic, hydrogen, alkyl, aryl heteroaryl, substituted alkyl, substituted aryl or substituted heteroaryl; provided that, if the first phenyl derivative includes an acyl halide substituent, then the substituent of the second phenyl derivative should be organometallic and vice versa, and further provided that one of the second substituents of either phenyl ring must be selected from the group consisting of substituted amino, nitro, halogen, hydroxyl, azide, —$OSO_2R$, —OR, —SR, and —N═NAr where R is alkyl and Ar is aromatic and be located adjacent the first substituent. The first and second compounds are reacted under conditions effective to form a ketone. The free amine is formed and this in turn is reacted with an amino acid derivative and cyclized the form the desired benzodiazepine or analog thereof.

3. Formation of Compounds of Formula 3–6

A wide variety of natural and unnatural amino acids with Fmoc-protected amine groups are readily available from suppliers to the industry (for example, from Aldrich Chemical Co., Milwaukee, Wis.). Any one of these may be coupled to the support-bonded unprotected 2-aminobenzophenone to form an amino acid-derivatized 2-aminobenzophenone 3. This is readily accomplished by first converting the amino acid to an activated acyl fluoride derivative, which results in efficient coupling to the 2-aminobenzophenone. A discussion of this technique is found in Carpino et al., *J. Am. Chem. Soc.* (1990) 112:9651–9652. The amino acid used in Reaction Scheme I has a variable side chain $R^B$, which introduces a third site for variation of the structure of the final benzodiazepine derivative. Base-catalyzed removal of the Fmoc protecting group from 3 followed by exposure to 5% acetic acid in dimethyl formamide (DMF) results in cyclization to provide the benzodiazepine structure 4.

Variation at a fourth site on the structure is achieved by alkylation of the amide nitrogen atom, i.e., at the 1-position on the benzodiazepine structure. This is accomplished by conventional techniques involving deprotonation of 4 by the use of a base followed by reaction with an alkylating agent. Examples of suitable bases are lithiated 5-phenylmethyl 2-oxazolidone in tetrahydrofuran (THF), lithium diisopropyl amide in THF, and lithium dicyclohexyl amide in THF, and in some cases depending on the susceptibility of other groups on the molecule, sodium hydride or potassium hydride in DMF. The alkylating agent may be either an activated alkylating agent such as methyl iodide or t-butyl bromoacetate, or an inactivated alkylating agent such as ethyl iodide or isopropyl iodide in the presence of DMF. The use of lithiated 5-phenylmethyl 2-oxazolidone (pKa in dimethyl sulfoxide (DMSO) 20.5) as the base for deprotonation allows alkylation of the benzodiazepine without alkylation of any groups represented by $R^A$, $R^{A'}$ or $R^B$ with higher pKa values, such as amides (pKa in DMSO of approximately 25–26), carbamates (pKa in DMSO of approximately 24.5), or esters (pKa in DMSO of approximately 30). The N-alkylated benzodiazepine 5 is then optionally cleaved from the support by conventional methods for cleaving an acid-labile linkage. This may be achieved for example by treatment with 85:5:10 trifluoroacetic acid/water/dimethylsulfide.

piperidine, followed by reaction in 5% acetic acid in DMF solution to form the imide. A fourth substituent may then be added by deprotonating the free amine of 4 using XpLi (lithium 5-(phenylmethyl)-2-oxazolidinone) in THF solution at −78° C. followed by reaction with an alkyl or aryl halide in DMF solution to give compound 5. The final product 6 may be removed from the solid support by reaction in a solution of trifluoroacetic acid, water and dimethylsulfide (85:10:5).

REACTION SCHEME VIII

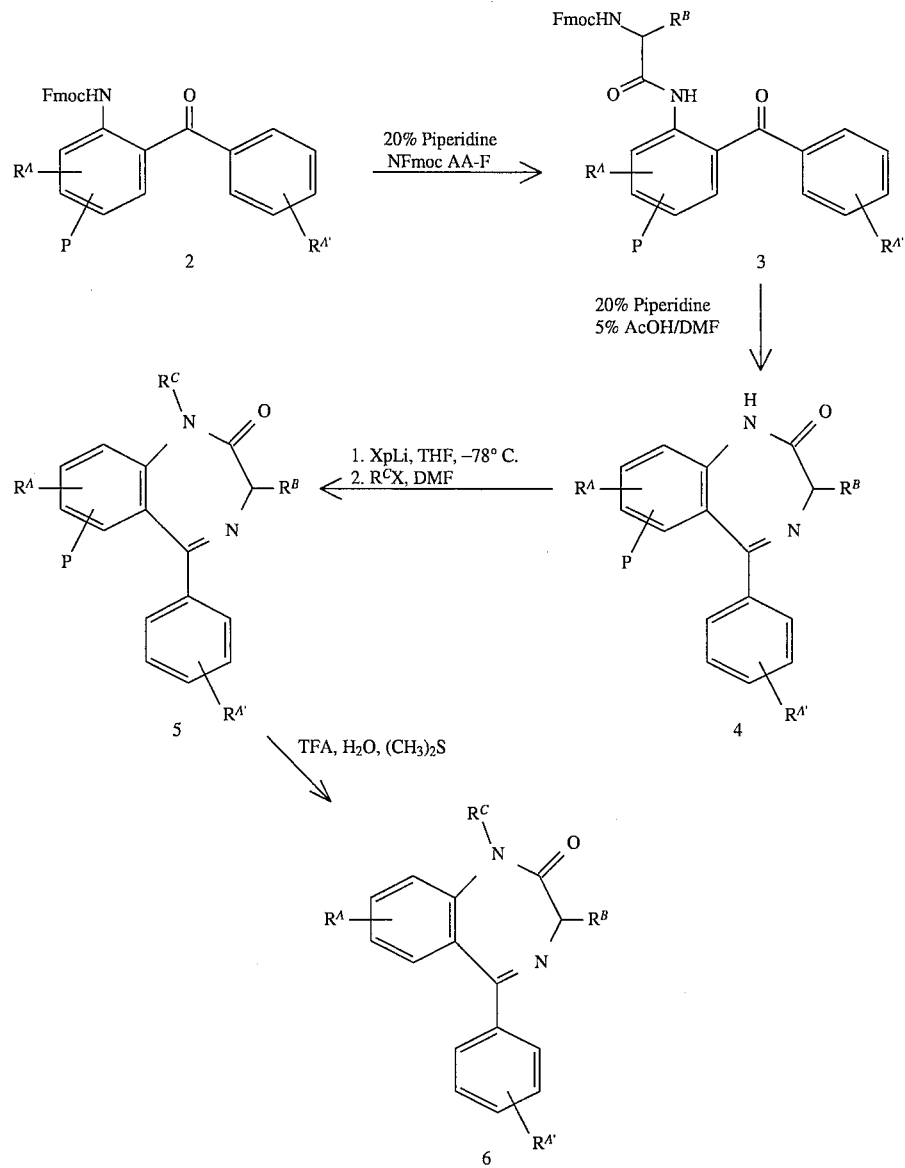

Reaction Scheme VIII illustrates in more detail the series of conversions just discussed. Support-bound aminobenzophenone 2 (the support is denoted by P) is reacted with 20% piperidine in DMF to remove the Fmoc protecting group. The free amine is then reacted with an Fmoc-protected amino acid fluoride in methylene chloride with 2,6-ditertbutylpiperidine as an acid scavenger to form amino acid 3. Cyclization to form benzodiazapine 4 is accomplished by first removing the Fmoc protecting group in 20%

Still further variations in the basic benzodiazepine structure may be made. For example, the amide formed by the adjacent NH and C=O groups of the heterocyclic ring can be converted to a thioamide; the imine (i.e., the =N— on the heterocyclic ring) can be reduced to an amine; or a second alkylation can be performed on an amide or carbamate functionality present in the molecule at a location other than the amide nitrogen that has been alkylated. Each of these reactions is performed by conventional means readily apparent to those skilled in the art (see, e.g., March).

Using this method of synthesis, a combinatorial library of benzodiazepine derivatives is constructed by methods which are analogous to any of the variety of similar methods known in the art for the synthesizing peptide derivatives.

C. Pin-Based Combinatorial Synthesis

1. Overview

One example of such a method is the pin method developed by Geysen et al., for combinatorial solid-phase peptide synthesis. A description of this method is offered by Geysen et al., *J. Immunol. Meth.* (1987) 102:259–274, incorporated herein by reference. According to this method as it may be practiced in the present invention, a series of 96 pins are mounted on a block in an arrangement and spacing which correspond to a 96-well Microtiter reaction plate, and the surface of each pin is derivatized to contain terminal aminomethyl groups. The pin block is then lowered over a series of reaction plates in sequence to immerse the pins in the wells of the plates where coupling occurs at the terminal aminomethyl groups and the various reactions in the reaction schemes described above are performed as discussed in greater detail below.

Reagents varying in their substituent groups occupy the wells of each plate in a predetermined array, to achieve as ultimate products a unique benzodiazepine on each pin. By using different combinations of substituents, one achieves a large number of different compounds with a common central benzodiazepine structure. For example, the synthesis may begin with ten different 2-aminobenzophenone derivatives (Compound I in Reaction Scheme I above, differing in terms of the substituents represented by $R^A$ and/or $R^{A'}$), and each of these ten may be reacted with different amino acids such as thirty different amino acids (differing in terms of the side chain represented by $R^B$ in Compound 3) to provide 300 different cyclic intermediates (Compound 3). Reaction of each of these 300 intermediates with fifteen different alkylating agents (as represented by the substituent $R^C$ in Compound 5) would result in 4,500 unique benzodiazepine derivatives. It will be appreciated that still more permutations may be formed by applying the Stille and other organometallic reactions as described above.

Once formed in this manner, each benzodiazepine derivative may be cleaved from its pin by treatment with acid, as described above. In one preferred embodiment of the invention, each benzodiazepine derivative will be prepared in sufficient quantity for screening purposes, and for analysis by such methods as high performance liquid chromatography (HPLC) and mass spectral analysis to verify the purity and integrity of the compound. Quantities on the order of approximately 50 nanomoles will generally suffice.

The resulting benzodiazepine combinatorial library may then be screened using the pin configuration in combination with appropriately charged and indexed Microtiter plates, or with similar multiwell arrangements. A typical screening, for example, may seek to compare the derivatives in the library in terms of their ability to bind to a particular receptor. Cholecystokinin receptors, which are widely distributed throughout the central and peripheral nervous system and mediate numerous physiological responses, are one example of such a receptor. Other examples will be readily apparent to those skilled in the arts of physiology and biotechnology. The screening method is based on assays for the receptors, the chemistry of the assays being conventional and well known. Radioligand assays are one example. For cholecystokinin, for example, crude membrane homogenates are prepared with minimal effort, in accordance with the procedures described by Chang et al., *Proc. Natl. Acad. Sci.* (1986) 83:4923–4926, incorporated herein by reference, and radiolabeled cholecystokinin can be purchased from New England Nuclear, Massachusetts, U.S.A. The screening may thus be based on any type of receptor, and will identify compounds within the library which show high affinity for the particular receptor chosen.

The methods described above may be used to prepare and screen large numbers of compounds, in the hundreds, the thousands and even the ten thousands in a reasonable period of time. Synthesis may be combined with screening in various different ways to screen compounds in unusually large libraries.

As one example of a strategy for a large library, the scheme may begin by the preparation of an equimolar mixture of a variety of 2-aminobenzophenone derivatives to which a common linker is attached (such as by the first reaction of Reaction Scheme II). Each pin of the 96-well array, surface-derivatized to contain a terminal amino group, is then contacted with this equimolar mixture to effect the coupling reaction. The result is that the entire combination of 2-aminobenzophenone derivatives will be evenly distributed over the surface of each pin. Each pin will then be reacted with a unique combination of amino acyl fluoride and alkylating agent to form a first library of benzodiazepine mixtures, each mixture distinguishable by the substituents $R^B$ and $R^C$ but not by the substituents $R^A$ and $R^{A'}$ for which each mixture will contain the full range. Screening this first library will provide the optimal combination of amino acid and alkylating agent. A second library is then constructed in which each pin is derivatized with only one 2-aminobenzophenone derivative, the array of pins thus representing an array of 2-aminobenzophenone derivatives, each pin however being then reacted with the optimal amino acid and alkylating agent identified in the first library. By screening the second library, one identifies the optimal 2-aminobenzophenone derivative.

2. Formation of a Pin-Bound Benzodiazapine Library

The formation of a pin-bound library of benzodiazapines having a variety of skeletal and side-chain variations will now be discussed. A library of substituted benzodiazapines was formed from the combination of eight amino acids (Ala, Val, Phe, Lys, Tyr, Asp, Nle, Gly) and 2-aminobenzophenones. The 2-aminobenzophenones were attached to sixteen pins, two pins for each amino acid. The yields of benzodiazapine products are listed below in Table I.

Starting from aminobenzophenone 21, the steps outlined in Reaction Scheme III were followed to attach linker 22, remove the allyl protecting group and affix the resulting compound 25 onto amino-functionalized pins (available commercially from Cambridge Research Biochemicals). See, Geyson, et al., *J. Immun. Methods,* 1987 102, 259–274; Rich, D. H., et al., In THE PEPTIDES, Gross, E., Meienhofer, J., eds., Academic Press, New York 1979, Vol. 1, pp. 242–264, both of which are incorporated herein by reference. A preferred concentration of aminobenzophenone-linker 25 is less than about 0.2 mM for efficient coupling. More preferred is a concentration of between about 0.025 to 0.075 mM, and most preferred is a concentration of about 0.05 mM.

Once attached to the pins, the aminobenzophenones were reacted with the $N^\alpha$-Fmoc-protected acyl fluoride derivatives of the above-listed amino acids, as illustrated above in Reaction Scheme VIII. The Fmoc-protected amino acid fluorides were subjected to additional purification steps by either additional acid and base extractions (3 washes with 1N NaHSO$_4$ followed by 3 washes with 1N NaHCO$_3$) or by chromatography. The coupling of the amino acid fluorides to the aminobenzophenones was accomplished as described above; although the use of an acid scavenger, such as 4-methyl-2,6-di-t-butylpyridine, was not required due to the small amounts of HF produced. It is noteworthy that the reaction of valine ($R^B$=(CH$_3$)$_2$CH—) required three days to proceed to completion due to the steric hinderance created by the side-chain. The cyclization to form the seven-membered ring also proceeded as described above; except that a temperature of 85° C. and 5% acetic acid/butanol were determined to be more preferred conditions.

To determine the relative yield of reaction products, the benzodiazapines were diluted with a DMF stock solution containing fluorenone as an internal standard. This solution was then analyzed using UV HPLC. As expected, different extinction coefficients were found for different 2-aminobenzophenones (see Levillain, P. et al., *Eur J. Med. Chem.*, 1975, 10: 433–439, which is incorporated herein by reference). However, all structures derived from the same 2-aminobenzophenone had approximately the same extinction coefficient. Thus, the yield for each benzodiazapine may be determined relative to the standard fluorophenone. The Table below indicates the results. Generally the results of the reactions were favorable.

TABLE I

| Fmoc-AA-F | Relative Yield |
| --- | --- |
| Ala | 1.00–1.04 |
| Val | 0.79–0.87 |
| Phe | 0.60–0.86 |
| Lys | 0.73–0.76 |
| Tyr | 0.72–0.78 |
| Asp | 0.70–0.79 |
| Nle | 1.04–1.10 |
| Gly | 0.96–0.106 |

3. Further Derivitization of the Benzodiazapines

N-alkylation of the free amino group ($R^C$, see Reaction Scheme VIII) was performed as follows. Lithium 5-(phenylmethyl)-2-oxazolidinone was prepared by adding n-butyllithium to 5-(phenylmethyl)-2-oxazolidinone in distilled THF with 10% DMF at −78° C. under nitrogen atmosphere to form the base lithium 5-(phenylmethyl)-2-oxazolidinone (XpLi in Scheme VIII). The base was then reacted with the pin-bound benzodiazapines for *** at 0° C. to deprotonate the amine and an alkyl or aryl halide was added to derivatize the free amine.

The relative yield of alkylation between different alkylating groups was determined by HPLC retention times and peak areas relative to a fluorenone standard. One half of this sample was then benzylated as described above with respect to Scheme VIII. The two samples were combined and their ratio was determined by comparing the peak areas of the $^1$H NMR spectrum of the combined samples. An aliquot of the combined samples was then diluted and analyzed by HPLC. Having determined a standard, eight alkylating agents were added to valine-derived benzodiazapines attached to eight different pins. The results are shown in Table II. Again, favorable conversion efficiencies were found.

TABLE II

| Substituent ($R^C$) | Ratio of Unalkylated/Alkylated Species |
| --- | --- |
| H | 85/0 |
| Bn | 3/44 |
| Me | 3/54 |

TABLE II-continued

| Substituent ($R^C$) | Ratio of Unalkylated/Alkylated Species |
| --- | --- |
| Et | 3/60 |
| Pr | 3/60 |
| Acetamide | 2/21 |
| Cinnamyl | 2/30 |
| Xylene | 5/32 |
| MeOBn | 10/30 |

B. Examples

Two methods of coupling substituted 2-aminobenzophenones to a solid phase substrate in accordance with Reaction Scheme II are illustrated below, in one of which the coupling is achieved through an HMPA linker by way of an ether linkage, and in the other by way of an ester linkage. This is followed by a description of a general procedure for the solid-phase synthesis of 1,4-benzodiazepines according to Reaction Scheme I, with results for each of a variety of specific structures actually prepared by the procedure. The solid-phase used in the synthesis is a particulate resin, and the description is followed by a description and examples of how the procedures in the synthesis are translated into a pin-based protocol suitable for multiple and simultaneous reactions.

1. General

Unless otherwise noted, materials were obtained from commercial suppliers and used without further purification. Fmoc-protected amino acids were purchased from Nova-Biochem, and anhydrous N,N-dimethylformamide (DMF) was purchased from Aldrich. Tetrahydrofuran (THF) was distilled from Na/benzophenone, and CH$_2$Cl$_2$ was distilled from CaH$_2$. The concentration of commercially available solutions of n-butyllithium in hexanes was periodically checked by titration with diphenylacetic acid, as described in Kendall, et al., *J. Org. Chem.*, 1979:44, 1421–1424, incorporated by reference. Organic extracts were dried over Na$_2$SO$_4$ and concentrated with a rotary evaporator. Flash chromatography was performed according to the procedure of Still (J. Org. Chem., 1978:43 2923, incorporated herein by reference) using Merck 60 230–400 mesh silica gel. Reactions and chromatography fractions were analyzed using Analtech 250-μm TLC plates. Analytical high pressure liquid chromatography was performed on a Rainin HPLC chromatography system employing a 5μ particle C18 column (4.6 mm×25 cm). Chemical shifts are expressed in ppm relative to internal solvent and J values are in hertz. Melting points were determined in open Pyrex capillaries and are uncorrected.

2. Formation of Linker

Allyl-2-(4-hydroxymethylphenoxy)acetate

To a flame-dried three-neck 250-mL round bottom flask fitted with stir bar and reflux condenser was added hydroxymethylphenoxyacetic acid (5.0 g, 27.5 mmol). Ethyl acetate (100 mL) was added and to the resulting solution was added diisopropylethylamine (3.55 g, 27.5 mmol) with stirring. To the resulting white slurry was added allyl bromide (3.33 g, 27.5 mmol) and the mixture was heated at reflux with stirring. After 5 hours, an additional portion of allyl bromide (2.8 g, 23 mmol) was added, and the slurry was refluxed for 12 hours. After allowing the mixture to cool to room temperature, ethyl acetate (100 mL) was added and the slurry was extracted with water (100 mL), 1N aqueous sodium bisulfate (100 mL), 1N aqueous sodium bicarbonate (100 mL), and 1N aqueous sodium chloride (100 mL), then dried over sodium sulfate and concentrated in vacuo to give pure product (5.8 g, 95% yield) which became an off-white solid upon storage at −20° C., with melting point 33.5°–34.5° C. The structure was confirmed by proton NMR, carbon-13 NMR, electron impact mass spectroscopy and elemental analysis.

Allyl-2-(4-bromomethylphenoxy)acetate

The allyl 2-(4-hydroxymethylphenoxy)acetate prepared above (3.03 g, 13.6 mmol) was dissolved in 20 mL of $CH_2Cl_2$. Triphenylphosphine (3.75 g, 14.3 mmol, 1.05 equivalents) was added and the resulting clear and colorless solution was cooled to 0° C. at which time carbon tetrabromide (4.77 g, 14,3 mmol, 1.05 equivalents) was added in one portion with stirring. The resulting yellow slurry was stirred at 0° C. for 0.5 hour. The slurry was then concentrated in vacuo followed by purification on a 5 cm×20 cm silica gel column with 60:40 $CH_2Cl_2$/hexane as the eluent. The pure product upon storing at −20° C. became a white solid, with $R_f$ 0.23 in 50:50 hexane. The structure was confirmed by proton NMR and carbon-13 NMR.

3. Attachment of Linker to Substituted 2-Aminobenzophenone Through Ether Coupling In the first three illustrations of 2-aminobenzophenone in this example, $R^A$ is a chlorine atom at the position on the ring directly opposite the amino group. The compound does not contain a substitution corresponding to $R^{A'}$. In the second three, both $R^A$ and $R^{A'}$ are hydrogen.

4-(4-(2-Amino-5-chloro-benzoyl)-phenoxymethyl) phenoxyacetic acid allyl ester

A solution was formed by dissolving 2-amino-5-chloro-4'-hydroxybenzophenone (1.72 g, 8.07 mmol) in 40 mL of DMF. Potassium bis(trimethylsilyl)amide that was 0.5M in toluene (16.1 mL, 8.07 mmol, 1.0 equivalents) was added dropwise with stirring. Allyl 2-(4-bromomethylphenoxy)acetate (2.30 g, 8.07 mmol, 1.0 equivalents) was then added and the resulting orange slurry was stirred at ambient temperature for 45 minutes. The slurry was concentrated in vacuo, then diluted with $CH_2Cl_2$ (150 mL) and was extracted with 1N aqueous sodium bicarbonate (100 mL) and with 1N aqueous sodium chloride (100 mL), then dried over sodium sulfate and concentrated in vacuo to give the product as a yellow solid which was approximately 95% pure and was taken to the next step without purification. The product had $R_f$ of 0.55 in 50:50:2 ethyl acetate/hexane/triethylamine. The structure was confirmed by proton NMR, carbon-13 NMR, and electron impact mass spectroscopy.

4-(4-(5-Chloro-2-fluorenylmethoxycarbonylamino-benzoyl)phenoxymethyl)phenoxyacetic acid allyl ester The product of the preceding paragraph (4.90 g, 10.8 mmol) and pyridine (1.02 g, 13 mmol, 1.2 equivalents) were dissolved in 60 mL of $CH_2Cl_2$. The resulting yellow solution was cooled to 0° C. and fluorenylmethoxycarbonyl chloride (2.95 g, 1.14 mmol, 1.05 equivalents) was added. The resulting solution was stirred at 0° C. for 15 minutes and then at ambient temperature for 1 hour. The solution was then diluted with $CH_2Cl_2$ (150 mL) and extracted twice with 1N aqueous sodium bisulfate (100 mL) and once with 1N aqueous sodium chloride (100 mL), then dried over sodium sulfate and concentrated in vacuo to give a yellow foam. The product was purified by recrystallization from $CH_2Cl_2$ and hexanes. The structure was confirmed by proton NMR, carbon-13 NMR, FAB mass spectroscopy and elemental analysis.

4-(4-(5-Chloro-2-fluorenylmethoxycarbonylamino-benzoyl)phenoxymethyl)phenoxyacetic acid The allyl ester of the preceding paragraph (1.80 g, 2.66 mmol) was dissolved in 30 mL of $CH_2Cl_2$. Tetrakis(triphenylphosphine)palladium (65 mg, 0.096 mmol, 0.02 equivalents) was added, and after flushing the reaction flask with nitrogen gas, tributyltin hydride (0.900 g, 3.09 mmol, 1.1 equivalents) was added slowly and dropwise with stirring over 2 minutes. The reaction solution turned from bright yellow to orange over 0.5 hour. The reaction solution was then diluted with $CH_2Cl_2$ (150 mL) and was extracted three times with 0.5N aqueous hydrochloric acid (100 mL) and once with aqueous sodium chloride (100 mL), then dried over sodium sulfate and concentrated in vacuo to give an off-white solid which was recrystallized from $CH_2Cl_2$ and hexanes. The structure was confirmed by proton NMR, carbon-13 NMR, FAB mass spectroscopy and elemental analysis.

4-(3-Amino-4-benzoylphenoxymethyl)phenoxyacetic acid allyl ester 2-amino-4-hydroxybenzophenone (3.55 g, 16.7 mmol) was dissolved in 90 mL of N,N-dimethylformamide (DMF). Potassium bis(trimethylsilyl)amide that was 0.5M in toluene (33.0 mL, 16.5 mmol, 1.0 equiv) was added dropwise with stirring. Allyl 2-(4-bromomethylphenoxy)acetate (4.47 g, 15.7 mmol, 0.95 equiv) was added and the resulting brown slurry was stirred at ambient temperature for 45 min. The slurry was concentrated in vacuo, diluted with $CH_2Cl_2$ (150 mL) and extracted with I N aqueous sodium bicarbonate (3×100 mL) and with 1N aqueous sodium chloride (100 mL), and then concentrated to give a yellow solid. Chromatography on silica gel (4 cm×20 cm) with ethyl acetate/hexane 25:75 to 33:66 provided 4.79 g (69% yield) pure product as a colorless oil: $R_f$0.6 (50:50 ethyl acetate/hexane). IR (film from $CH_2Cl_2$, partial) 3473, 3360, 1757, 1615, 1514 $cm^{-1}$; $^1H$ NMR (300 MHz, $CDCl_3$) δ 4.63 (s,2), 4.67 (d, 2, J=5.8), 4.90 (s,2), 5.23 (dd, 1, J=1.0, 10.4), 5.31 (dd, 1, J=1.3, 7.2), 5.89 (m, 1), 6.17 (dd, 1, J=2.3, 8.9), 6.20 (d, 1, J=2.1) 6.45 (s, 2), 6.90 (d, 2, J=8.6, 7.30–7.47 (m, 5), 7.54 (d, 1, J=1.7), 7.56 (s, 1). $^{13}C$ NMR (75.5 MHz, $CDCl_3$) δ 65.4, 65.8, 69.8, 114.2, 114.4, 114.9, 118.3, 119.1, 119.7, 120.0, 129.2, 129.5, 131.4, 131.7, 132.7, 133.5, 148.8, 157.8, 161.8, 168.4, 196.4. Anal. Calcd for $C_{25}H_{23}NO_5$: C, 71.90; H, 55.5; N, 3.36. Found: C, 71.75; H, 5.49; N, 3.37.

4-(4-Benzoyl-3-fluorenylmethoxycarbonylamino-phenoxymethyl) phenoxyacetic acid allyl ester 4-(3-Amino-4-benzoylphenoxymethyl)phenoxyacetic acid allyl ester (4.74 g, 11.4 mmol) and pyridine (1.09 g, 13.7 mmol, 1.2 equiv) were dissolved in 60 mL of $CH_2Cl_2$. The resulting yellow solution was cooled to 0° C., and fluorenylmethoxycarbonyl chloride (2.65 g, 1.14 mmol, 1.05 equiv) was added. The resulting solution was stirred at 0° C. for 15 min and then at ambient temperature for 1 h. The solution was diluted with $CH_2Cl_2$ (150 mL), extracted twice with 1N aqueous sodium bisulfate (100 mL), once with dilute aqueous sodium chloride (100 mL), and then concentrated to give a yellow foam. The unpurified product was crystallized from $CH_2Cl_2$ and hexanes to give 4.87 g (79% yield) purified material as a white solid: mp 96.5°–97.5° C. $R_f$0.45 ($CH_2Cl_2$); IR (film from $CH_2Cl_2$, partial) 3230(b), 1740, 1610, 1575 $cm^{-1}$; $^1H$ NMR (300 MHz, $CDCl_3$) δ 4.32 (t, 1, J=7.4), 4.44 (s, 1, J=0.5), 4.71 (dd, 2, J=1.2, 5.9), 5.11 (s, 2), 5.26 (dd, 1, J=1.2, 10.4), 5.30 (dd, 1, J=1.4, 17.2), 5.85–598 (m, 2), 6.58 (dd, 2, J=2,5m 8.9) 6.92 (d, 2, J=8.8, 6.92 (q, 2, J=4.8, 9.6), 7.30–7.59 (m, 8), 7.63–7.70 (m,5), 7.76 (d, 2, J=8.9), 7.77 (d, 2, J=7.5), 8.29 (d, 1, J=2.3). $^{13}C$ NMR (75.5 MHz, $CDCl_3$) δ 47.3, 65.6, 66.2, 67.9, 70.0, 104.4, 109.6, 115.2, 115.8, 119.5, 120.4, 125.6, 127.5, 128.1, 128.8, 129.6, 129.8, 131.7, 131.9, 137.6, 140.0, 141.6, 144.1, 144.6, 154.1, 158.5, 164.1, 167.8, 199.1. Anal. Calcd for $C_{40}H_{33}NO_7$: C, 75.10; H, 5.20; N, 2.19. Found: C, 75.21; H, 5.33; N, 2.28.

4-(4-Benzoyl-3-fluorenylmethoxycarbonylaminophenoxymethyl) phenoxyacetic acid 4-(4-Benzoyl-3-fluorenylmethoxycarbonylaminophenoxymethyl)-phenoxyacetic acid allyl ester (2.76 g, 4.33 mmol) was dissolved in 50 mL of $CH_2Cl_2$. Tetrakis(triphenylphosphine)palladium (11 mg, 0.087 mmol, 0.02 equiv) was added to the solution, and after flushing the reaction flask with $N_2$, tributyltin hydride (1.28 g, 4.75 mmol, 1.10 equiv) was added dropwise with stirring over 2 min. The reaction solution turned from bright yellow to orange over 0.5 h. The reaction solution was then diluted with $CH_2Cl_2$ (150 mL), extracted three times with 0.5N aqueous hydrochloric acid (100 mL), once with dilute aqueous sodium chloride (100 mL), and then concentrated to give an off-white solid which was recrystallized from $CH_2Cl_2$ and hexanes to provide 1.92 g (75% yield) of purified material: mp 176°–177° C.; $R_f$ 0.25 (75:25:1 ethyl acetate/hexane/acetic acid); IR (film from $CH_2Cl_2$, partial) 3340(b), 1732, 1637, 1598, 1514 $cm^{-1}$; $^1H$ NMR (400 MHz, $d_6$-DMSO) δ 4.32 (t, 1, J=7.5), 4.45 (d,2, J=7.6), 4.68 (s, 2), 5.10 (s, 2), 6.59 (dd, 1, J=2.5, 9.0), 6.94 (d, 2, J=8.8), 7.32 (q, 1, J=1.1, 7.4), 7.35 (d, 1, J=1.2), 7.39–7.75 (m, 4), 7.63–7.70 (m, 9), 7.77 (d, 2, J=7.4), 8.24 (d, 1, J=2.5), 8.81 (s, 1). $^{13}C$ NMR (101 MHz, $d_6$-DMSO) δ 46.4, 64.4, 66.1, 69.3, 114.3, 114.4, 120.1, 125.1, 125.6, 127.1, 127.6, 128.1, 128.6, 129.2, 129.6, 131.1, 131.9, 132.9, 135.3, 140.7, 143.5, 153.7, 157.0, 162.3, 170.1, 192.2. HRMS (FAB, m-nitobenzyl alcohol) calcd for $C_{37}H_{30}NO_7$ (M+H) 600.2024, found 600.2022.

4. Coupling 2-Aminobenzophenone-Linker Complex to Solid Support

To a 30 mL peptide reaction flask was added 4-(4-(5-chloro-2-fluorenylmethoxycarbonylamino-benzoyl)-phenoxymethyl)phenoxyacetic acid (1.52 g, 2.4 mmol, 2.0 equivalents), aminomethyl resin (1.99 g, 1.19 mmol of 1% crosslinked divinylbenzene-styrene, 100 mesh size, substitution level 0.60 milliequivalents/g), and hydroxybenzotriazole monohydrate (0.808 g, 5.28 mmol, 4.4 equivalents). Anhydrous DMF (12 mL) was added to the flask and the mixture was vortexed for 0.5 hour to fully solvate the resin. Diisopropylcarbodiimide (808 mg, 5.28 mmol, 4.4 equivalents) was added by syringe. The reaction flask was stoppered and then vortexed for 24 hours at which point the ninhydrin test on approximately 10 mg of the solid support demonstrated that coupling was complete. The solvent and reagents were filtered away from the solid support and the support was rinsed five times with 20 mL DMF and five times with 20 mL $CH_2Cl_2$ (for each rinse the mixture was vortexed for at least 30 seconds before filtering off the solvent) and then dried in vacuo for 12 hours.

5. Attachment of Linker to Aminobenzophenone Through Ester Coupling

A different substituted aminobenzophenone and linker from those used in the preceding paragraphs are used here, with a variation in the type of connecting group joining the two together.

4-Benzoyl-6-chloro-3-fluorenylmethoxycarbonylaminobenzoic acid

A solution was prepared by diluting 3-amino-4-benzoyl-6-chlorobenzoic acid (5.59 g, 20.3 mmol) with approximately 70 mL of $CH_2Cl_2$. Chlorotrimethylsilane (5.50 g, 51 mmol, 2.5 equivalents) was added by syringe and the resulting white slurry was heated at gentle reflux for 1.5 hours. After cooling the mixture to 0° C., pyridine (3.69 g, 46.7 mmol, 2.3 equivalents) was added by syringe, immediately followed by addition of fluorenylmethoxycarbonyl chloride (5.78 g, 22.3 mmol, 1.1 equivalents). The resulting slurry was stirred for one hour under a nitrogen atmosphere. The reaction solution was then diluted with $CH_2Cl_2$ (150 mL) and was extracted three times with 1.0N aqueous sodium bisulfate (100 mL) and once with aqueous sodium chloride (100 mL), then dried over sodium sulfate and concentrated in vacuo to give a viscous oil. Pure product was obtained in 64% yield (6.50 g) as a white solid by flash chromatography with 5 cm×25 cm silica gel and 40:60 ethyl acetate and then 75:25:1 ethyl acetate/hexane/acetic acid as the eluent. The structure was confirmed by proton NMR, carbon-13NMR, and FAB mass spectroscopy.

4-Benzoyl-6-chloro-3-fluorenylmethoxycarbonyl aminobenzoyloxymethylphenoxyacetic acid allyl ester To a flame-dried 50 mL flask fitted with stir bar was added 4-benzoyl-6-chloro-3-fluorenylmethoxycarbonylaminobenzoic acid (2.50 g, 5.02 mmol) and allyl 2-(4-bromomethylphenoxy)acetate (1.12 g, 5.02 mmol). To this was added $CH_2Cl_2$ (15 mL), followed by addition of N,N-dimethylformamide dineopentyl acetal (1.16 g, 5.02 mmol, 1.0 equivalents) by syringe. The resulting red solution was stirred for 15 hours at ambient temperature, then diluted with $CH_2Cl_2$ (150 mL), then extracted once with 1.0N sodium bisulfate (100 mL) and once with aqueous sodium chloride (100 mL), then dried over sodium sulfate and concentrated in vacuo to give a red oil. Pure product was obtained in 63% yield (2.23 g) as a pale yellow oil by flash chromatography on 5 cm×25 cm silica gel eluting with 25:75 hexane/$CH_2Cl_2$ followed by 100% $CH_2Cl_2$. The structure was confirmed by proton NMR, carbon-13NMR, FAB mass spectroscopy and elemental analysis.

4-Benzoyl-6-chloro-3-fluorenylmethoxycarbonyl aminobenzoyloxymethylphenoxyacetic acid The product of the preceding paragraph (2.2 g, 3.13 mmol) was dissolved in 40 mL of $CH_2Cl_2$. To this was added tetrakis(triphenylphosphine)palladium (72 mg, 0.063 mmol, 0.02 equivalents), and after flushing the reaction flask with nitrogen gas, tributyltin hydride (1.00 g, 3.44 mmol, 1.1 equivalents) was added slowly dropwise with stirring over 3 minutes. The reaction solution turned from bright yellow to brown over 0.75 hour. The reaction solution was then diluted with $CH_2Cl_2$ (150 mL), then extracted three times with 0.5N aqueous hydrochloric acid (100 mL) and once with aqueous sodium chloride (100 mL), then dried over sodium sulfate and concentrated in vacuo to give an off-white solid which was recrystallized from $CH_2Cl_2$ and hexanes to provide the pure product as an off-white solid (1.60 g, 77% yield). The structure was confirmed by proton NMR, carbon-13NMR, and FAB mass spectroscopy.

6. Coupling 2-Aminobenzophenone-Linker Complex to Solid Support

To a 30 mL peptide reaction flask was added the product of the preceding paragraph (2.0 g, 3.02 mmol, 2.0 equivalents), aminomethyl resin (1.91 g, 1.51 mmol of 1% crosslinked divinylbenzene-styrene, 200–400 mesh size, substitution level 0.79 milliequivalents/g), and hydroxybenzotriazole monohydrate (0.925 g, 6.04 mmol, 4.4 equivalents). Anhydrous DMF (10.4 mL) was added to the flask and the mixture was vortexed for 0.5 hour to fully solvate the resin. Diisopropylcarbodiimide (762 mg, 6.04 mmol, 4.4 equivalents) was added by syringe and an additional 2.0 mL of DMF was added to rinse down the sides of the peptide reaction flask. The reaction flask was stoppered and then vortexed for 24 hours at which point the ninhydrin test on approximately 10 mg of the solid support demonstrated that coupling was complete. The solvent and reagents were filtered away from the solid support and the support was rinsed five times with 20 mL DMF and five times with 20 mL $CH_2Cl_2$ (for each rinse the mixture was vortexed for at least 30 seconds before filtering off the solvent) and then dried in vacuo for 12 hours.

7. General Protocol for Synthesis of 1,4-Benzodiazepine Derivatives on Solid Support A quantity of the dry solid support to which is bound the substituted 2-aminobenzophenone as prepared above, corresponding to structure 2 of Reaction Scheme I above, in which the quantity of substituted 2-aminobenzophenone amounts to 0.5–0.15 mmol, is added to a 50 mL round bottom flask fitted with a stir bar. Approximately 15 mL of DMF is added to the reaction flask and the resulting slurry is stirred for 1 hour at ambient temperature to ensure that the support is solvated. The DMF is then removed by a filtration cannula. To the remaining solvated solid support is added 15 mL of 20% piperidine in DMF, and the resulting yellow slurry is stirred for 20 to 30 minutes at ambient temperature. The solvent is then removed by the filtration cannula and the remaining yellow solid support is rinsed five times in 10 mL DMF and five times in 10 mL $CH_2Cl_2$, each washing continuing for approximately thirty seconds with stirring, with cannula filtration between successive washings. This results in the removal of the protecting group from the support-bound 2-aminobenzophenone.

The support with the unprotected 2-aminobenzophenone is now combined with a $CH_2Cl_2$ solution containing 0.2M of an Fmoc-protected aminoacyl fluoride (with any of various groups for $R^B$) and 0.2M 2,6 -di-t-butyl-4-methylpyridine (at least eight-fold excess relative to the molar amount of support-bound 2-aminobenzophenone). After stirring the resulting slurry for 15 hours at ambient temperature, the solution is removed by filtration cannula, and the support-bound intermediate (which corresponds to structure 3 of Reaction Scheme I) is washed three times each with 10 mL $CH_2Cl_2$ and 10 mL DMF in the manner described above. A yellow slurry is then formed by adding 15 mL of 20% piperidine in DMF. The slurry is stirred for twenty to thirty minutes at ambient temperature. The solvent is then removed by filtration cannula, and the yellow support is rinsed three times each with 10 mL DMF and 10 mL $CH_2Cl_2$ in the manner described above. The resulting intermediate is then diluted with 25 mL of 5% acetic acid in DMF, and the slurry is stirred at 40°–45° C. for 12 hours. The solvent is then removed by filtration cannula, leaving the cyclic product attached to the support, corresponding to structure 4 of Reaction Scheme I. The support is then rinsed three times each with 10 mL DMF and 10 mL freshly dried tetrahydrofuran (THF) in the manner described above. The reaction flask is then sealed with a fresh rubber septum, flushed with nitrogen, and placed under positive nitrogen pressure. Once pressurized, the flask is placed in a –78° C. acetone/dry ice bath.

In a separate flame-dried 25 mL round bottom flask fitted with a stir bar is added 12 mole equivalents of 5-phenylmethyl-2-oxazolidinone relative to the molar amount of the support-bound cyclic product. The flask is then stoppered with a rubber septum and flushed with nitrogen for five minutes, then maintained under positive nitrogen pressure. To the flask is then added freshly distilled THF in a volume appropriate to provide a 0.12 M solution of 5-phenylmethyl-2-oxazolidinone in THF. The resulting clear and colorless solution is then cooled to –78° C. and 10 mole equivalents of 2.0M n-butyl lithium in hexanes relative to the molar amount of the support-bound material is then added dropwise with stirring. The solution is then stirred at –78° C. for 15 minutes, and then transferred by cannula to the reaction flask containing the solid support, with stirring at –78° C.

The resulting slurry is stirred at –78° C. for 1.5 hours at which point 15 mole equivalents of the appropriate alkylating agent (the alkyl group corresponding to the substituent $R^C$ in Reaction Scheme I) is added by syringe, followed by approximately 10 mL of anhydrous DMF. The resulting slurry is allowed to warm to ambient temperature with stirring. After 3 hours of stirring at ambient temperature, the solvent is removed by filtration cannula. The support is then washed once with 10 mL THF, twice with 10 mL of 1:1 THF/water, twice with mL THF, and twice with 10 mL $CH_2Cl_2$. The product on the solid support at this point is the alkylated benzodiazepine represented by the structure 5 of Reaction Scheme I.

To the solid support is then added 15 mL of 95:5:10 trifluoroacetic acid/water/dimethylsulfide. The resulting slurry is stirred to 3½ hours, then concentrated in vacuo. The yellow solid is then diluted with 5 mL of 1:2 methanol/$CH_2Cl_2$ and filtered to remove the solid support. The solid support is then rinsed three times with mL of the same solvent. Concentration of the combined filtrate then provides the unpurified product corresponding to structure 6 of Reaction Scheme I, with a purity of 80–100%. The product is then purified by silica gel chromatography with either methanol (2–10%) in $CH_2Cl_2$ or with hexane/ethyl acetate/acetic acid 48-0/50-98/2.

Following this general procedure, the following benzodiazepine derivatives were prepared, the structure of each confirmed as indicated:

---

7-Chloro-1,3-dihydro-5-(4-hydroxyphenyl)-3-methyl-(2H)1,4-benzodiazepin-2-one
(Structure confirmed by proton NMR, carbon-13 NMR, and electron impact mass spectrometry.)

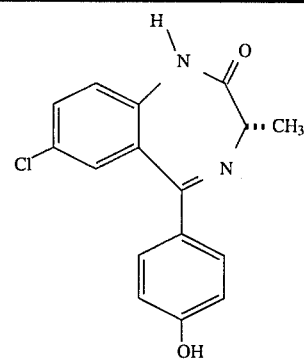

7-Chloro-1,3-dihydro-5-(4-hydroxyphenyl)-1,3-dimethyl-
(2H)1,4-benzodiazepin-2-one
(Structure confirmed by proton NMR, carbon-13 NMR,
and electron impact mass spectrometry.)

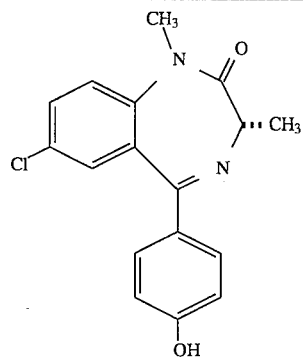

7-Chloro-1,3-dihydro-5-(4-hydroxyphenyl)-1-ethyl-3-methyl-
(2H)1,4-benzodiazepin-2-one
(Structure confirmed by proton NMR, carbon-13 NMR,
and FAB mass spectrometry in m-nitrobenzyl alcohol.)

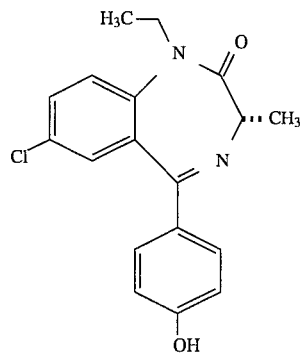

1-Allyl-7-chloro-1,3-dihydro-5-(4-hydroxyphenyl)-3-methyl-
(2H)1,4-benzodiazepin-2-one
(Structure confirmed by proton NMR, carbon-13 NMR,
and FAB mass spectrometry in m-nitrobenzyl alcohol.)

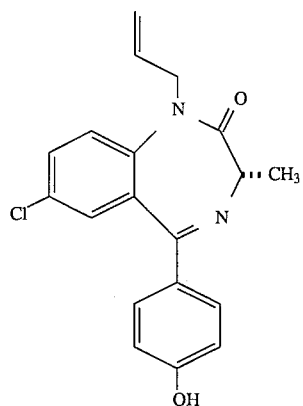

7-Chloro-1,3-dihydro-5-(4-hydroxyphenyl)-1-ethyl-3-(4-
hydroxyphenylmethyl)-(2H)1,4-benzodiazepin-2-one
(Structure confirmed by proton NMR, carbon-13 NMR,
and electron impact mass spectrometry.)

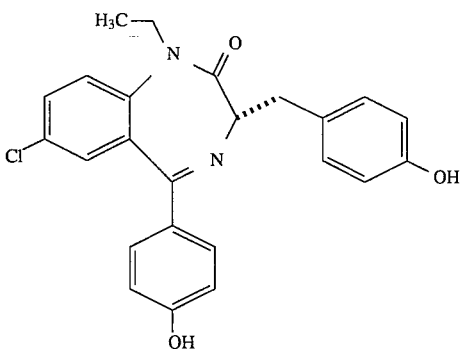

-continued

8-Carboxy-7-chloro-1,3-dihydro-1,3-dimethyl-5-phenyl-(2H)1,4-benzodiazepin-2-one
(Structure confirmed by proton NMR and carbon-13 NMR.)

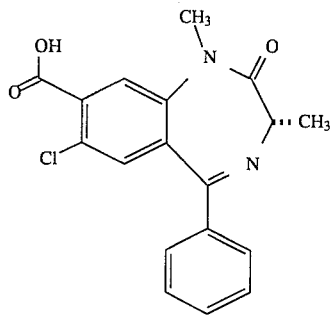

7-Chloro-1,3-dihydro-1-ethyl-5-(4-hydroxyphenyl)-3-isopropyl-(2H)1,4-benzodiazepine-2-one
(Structure confirmed by proton NMR, carbon-13 NMR and FAB mass spectrometry in m-nitrobenzyl alcohol.)

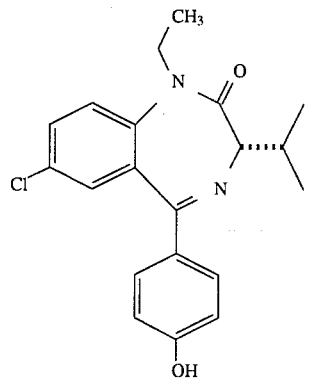

7-Chloro-1,3-dihydro-3-carboxymethyl-1-ethyl-5-(4-hydroxyphenyl)-(2H)1,4-benzodiazepine-2-one
(Structure confirmed by proton NMR, carbon-13 NMR and FAB mass spectrometry in m-nitrobenzyl alcohol.)

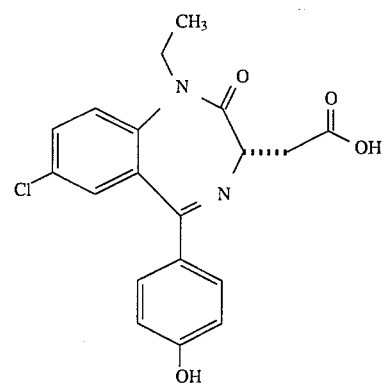

8-Carboxy-7-chloro-1,3-dihydro-1-methyl-5-phenyl-3-phenylmethyl-(2H)1,4-benzodiazepine-2-one
(Structure confirmed by proton NMR, carbon-13 NMR and FAB mass spectrometry in m-nitrobenzyl alcohol.)

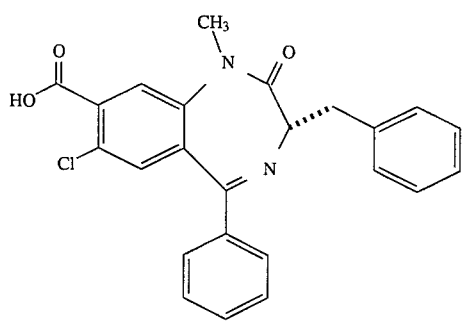

8-Carboxy-7-chloro-1,3-dihydro-3-methyl-5-phenyl-1-phenylmethyl-(2H)1,4-benzodiazepine-2-one
(Structure confirmed by proton NMR, carbon-13 NMR and FAB mass spectrometry in m-nitrobenzyl alcohol.)

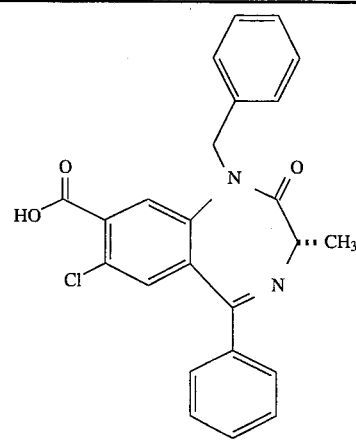

7-Chloro-1,3-dihydro-1-ethyl-5-(4-hydroxyphenyl)-1-ethyl-3-(4-aminobutyl)-(2H)1,4-benzodiazepine-2-one
(Structure confirmed by proton NMR and FAB mass spectrometry in m-nitrobenzyl alcohol.)

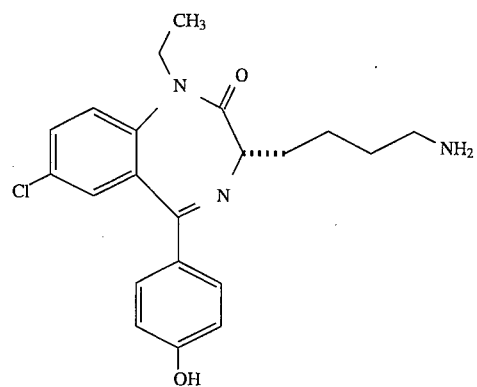

8. Racemization Assay

The following assay confirmed that racemization had not occurred during any step of the reaction sequence. The test species were the benzodiazepine derivative (S)- and (R)-isomers of 7-chloro- 1,3-dihydro-5-(4-hydroxyphenyl)-1-ethyl-3-methyl-(2H)1,4-benzodiazepin- 2-one, the third of the eleven products shown above ($R^A$=Cl at the 7-position on the structure, i.e., para- relative to the amide group, $R^B$=methyl and $R^C$=ethyl).

The (S)-isomer was prepared according to the general protocol described above, using (S)-N-Fmoc-alanyl fluoride for amide bond formation and ethyl iodide as the alkylating agent. The benzodiazepine was treated with excess diazomethane in 5:1 THF/methanol for 2 hours to give the methyl ether product. The ether product was evaluated for optical purity by HPLC analysis on a 10 mm×25 cm 3,5-dinitrobenzoylphenylglycine chiral Pirkle column with 2% isopropanol in hexane as the eluent, a flow rate of 6 mL/min and with absorbance monitored at 260 nm. The (S)-benzodiazepine eluted at 22.24 min. None of the (R)-benzodiazepine was observed (i.e., less than 1%), confirming that racemization had not occurred.

The procedure was repeated, except that (R)-N-Fmoc-alanyl fluoride was used in place of (S)-N-Fmoc-alanyl fluoride. The (R)-benzodiazepine eluted at 21.628 min.

9. Solid Phase Synthesis of 1,4-Benzodiazepines on Amino-derivatized Polyethylene Pins in 96 Well Microtiter Plates Amino-derivatized polyethylene pins (commercially available from Cambridge Research Biochemicals) were presolvated in $CH_2Cl_2$ (0.8 mL for 5 min) as described by Bellamy, et al., *Tet. Lett.*, 1984:25, 839–842, which is incorporated herein by reference, and then rinsed with MeOH (air dried to 10 min), DMF, prior to Fmoc deprotection with 1:4 piperidine in DMF (1×1 min, then 1×20 min.). After rinses with DMF, MeOH (air dry), DMF (x2), a 0.05M solution of aminobenzophenone-linker 24 in DMF was coupled to the pins for 12 h with hydroxybenzatriazole and diisopropylcarbodiimide for form 25. After rinses with DMF (x2), MeOH (air dried), $CH_2Cl_2$ (x2), DMF, the Fmoc of 25 was removed with 1:4 piperidine in DMF (1×1 min, then 1×20 min). The yellow pins were rinsed with DMF (x3), MeOH (air dried), $CH_2Cl_2$, and then coupled with a 0.2M solution of Fmoc AA-F in $CH_2Cl_2$ with the microtiter plates in a $CH_2Cl_2$ for 3 days to form 53. Coupling could be monitored by the disappearance of the yellow color of the pins (the aminobenzophenone is yellow, while the anilide product is clear). After 3 days the pins were rinsed with $CH_2Cl_2$ (x3), MeOH (air dried), DMF (x2), followed by a second Fmoc deprotection with 1:4 piperidine in DMF (1×1 min, then 1×20 min). The pins were rinsed with DMF (30 min), MeOH, DMF (x2), then 53 was exposed to 5% acetic acid/butanol at 90° C. for 12 h to give the cyclic product 55. Compound 55 was rinsed with DMF (x3) and THF. The pins, and all necessary reagents, were then transferred to a glove bag preflushed with $N_2$ (g). After another THF rinse, compound 55 was deprotonated for 30 min at 0° C. with 0.14M lithium oxazolidinone in THF (with 10% v/v DMF), and alkylated with 0.40 M alkylating agent in DMF for 12 h at ambient temperature all in the glove bag. Lithiated oxazolidinone was prepared in a flame-dried round bottom flask by dissolving 5-phenylmethyl-2-oxazolidinone (0.15 g, 0.85 mmol) in 5 mL THF and cooling to −78° C., then 1.6M n-butyllithium in hexanes was added dropwise with stirring by syringe (0.8 mole equiv relative to oxazolidinone). The solution was stirred for 15 min and 0.5 mL of dry DMF was added via syringe prior to deprotonation of compound 55.

Alkylating agents were purchased from Aldrich Chemical Co. and filtered through alumina except when they were solids. The 0.4M solutions of alkylating agents in dry DMF were prepared immediately prior to alkylation. After alkylation the benzodiazepine product 57 was removed from the glove bag, rinsed with DMF, DMF/H$_2$O, MeOH (air dried), CH$_2$Cl$_2$, and cleaved from the support for 6 h with 85:5:10 trifluoroacetic acid/water/dimethylsulfide. TFA solution was removed from the wells with a Jouan rotary evaporator (model #RT105) to give unpurified 1,4-benzodiazepines 59 spatially separate in the microtiter plates. Benzodiazepines were dissolved in exactly 200 μl of a DMF stock solution containing 4 mg/mL of fluorenone as an internal standard. Percent yields were determined relative to other benzodiazepines and fluorenone on a Rainin UV-HPLC using a 15–100% methanol/water (0.1% TFA) gradient over 40 min with a 1 mL/min flow rate and monitoring absorbance at 350 nm.

Benzodiazepines Synthesized on Pins
and Their Retention Times by HPLC

| 1,4-benzodiazepines[a] | Retention Times[b] |
|---|---|
| A/H[c] | 17[d] |
| V/H | 24 |
| F/H | 28 |
| K/H | 15 |
| Y/H | 22 |
| R/H | 18 |
| W/H | 30 |
| N/H | 27 |
| G/H | 16 |
| V/Me | 27 |
| V/Et | 29 |
| V/nPr | 31 |
| V/Bn | 32 |
| V/MeOBn | 32 |
| V/Acetamide | 21 |
| V/Xyl | 34 |
| V/Cinnamyl | 35 |
| A/Bn | 27 |
| A/Acetamide | 18 |
| A/Cinnamyl | 30 |
| A/Et | 17 |
| A/Me | 25 |
| A/Xyl | 34 |
| A/H/aminobenzophenone 2b (2-amino-5-chloro-4'-hydroxybenzophenone) | 16 |

[a]Unless otherwise stated, benzodiazepines were derived from aminobenzophenone 2b.
[b]Retention times are given in minutes. For relative yields of individual experiments, see the Results and Discussion section.
[c]Benzodiazepines are abbreviated by amino acid and alkylating agent, i.e., valine/benzylated/benzodiazepine derivative is abbreviated V/Bn.
[d]Fluorenone, the internal standard, has a retention time of 33 min.

10. Combinatorial Synthesis and Screening

The procedures described in the preceding sections of this example are used in a combinatorial synthesis by using pins in place of the solid phase particles in one embodiment. The removal of reaction solutions and rinses from the support is accomplished by physically lifting the pins out of the reaction solutions which are retained in 96-well Microtiter plates, and dipping them into rinse solutions, rather than employing a filtration cannula. Air- and water-sensitive reactions are conducted in a glove bag or glove box. The benzodiazepine derivatives are cleaved from the pins into the wells of a 96-well Microtiter plate by treatment with the acid cleavage cocktail 95:5:10 trifluoroacetic acid/water/dimethylsulfide. The cleavage cocktail is then removed by employing a Microtiter plate speed vacuum apparatus (such as Savant Speed Vac and Microtiter Rotor, Model #SS). Screening is then performed by any of the standard methods for performing screens on Microtiter plates. These methods represent an adaptation of the methods described by Geysen and coworkers in Geysen et al., *J. of Immunological Methods* (1987) 102:259–274, incorporated herein by reference.

III. Prostaglandins

A. Description

In a similar manner, the invention is applicable to preparing and screening derivatives of prostaglandins, which are local hormones that regulate a wide variety of physiological processes. Naturally occurring prostaglandins and synthetic derivatives have served as important therapeutic agents for treating many physiological disorders. The present invention may be used for the study of prostaglandins with such goals as developing more potent derivatives or developing derivatives specific for disorders for which no known prostaglandins are effective.

Here as well, a solid-phase synthesis method has been developed. An illustration of this method is shown in Reaction Scheme IX.

REACTION SCHEME IX

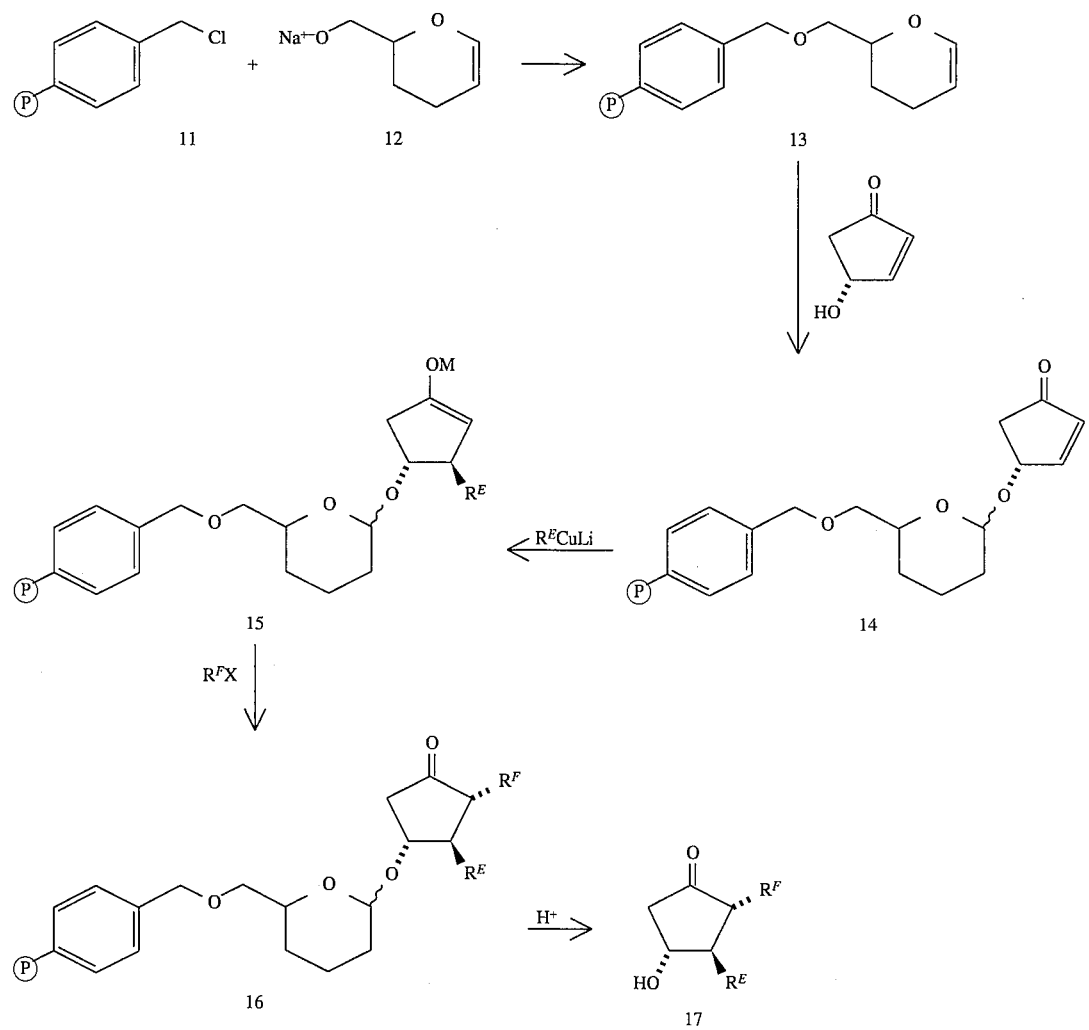

The solid phase in this method is a polystyrene/divinyl benzene resin (represented by the circled P in the Reaction Scheme) that has been surface-derivatized to include terminal benzyl chloride groups 61. A functionalized dihydropyran 62 is coupled to the resin through an alkylative process in accordance with the procedure of Merrifield, as described in Lu et al., *J. Org. Chem.* (1981) 46:3433–3436, to form the further derivatized resin 63. The resin is then reacted with in the presence of acid to form the coupled product 64a. The coupling not only serves to immobilize the β-hydroxycyclopentenone, but also to prevent intermolecular proton transfer between unreacted hydroxycyclopentenone and the enolate which would be formed upon cuprate addition to the hydroxycyclopentenone if the latter were not coupled in this manner.

A second, more preferred route to the intermediate β-hydroxycyclopentenone pyranyl ether, such as 64a, is shown as 64b in Reaction Scheme X below. The di-dihydropyranyl ester 68, available commercially (Fluka) is hydrolized in a basic water/dioxane solution to form in part alcohol 12 which is coupled to a bromoalkyl derivatized poly(styrene)block(polyoxoethylene) support 69, known commercially as "Tentagel-S" (Rapp Polymere), using NaHMDS and N,N dimethylacetamide (DMAc) at dry-ice temperature to form the polymer-bound ether 70. Reaction of 70 with β-hydroxycyclopentenone with acid catalysis—pyridinium p-toluenesulfonate (PPTS) in methylene chloride—provides 64b.

REACTION SCHEME X

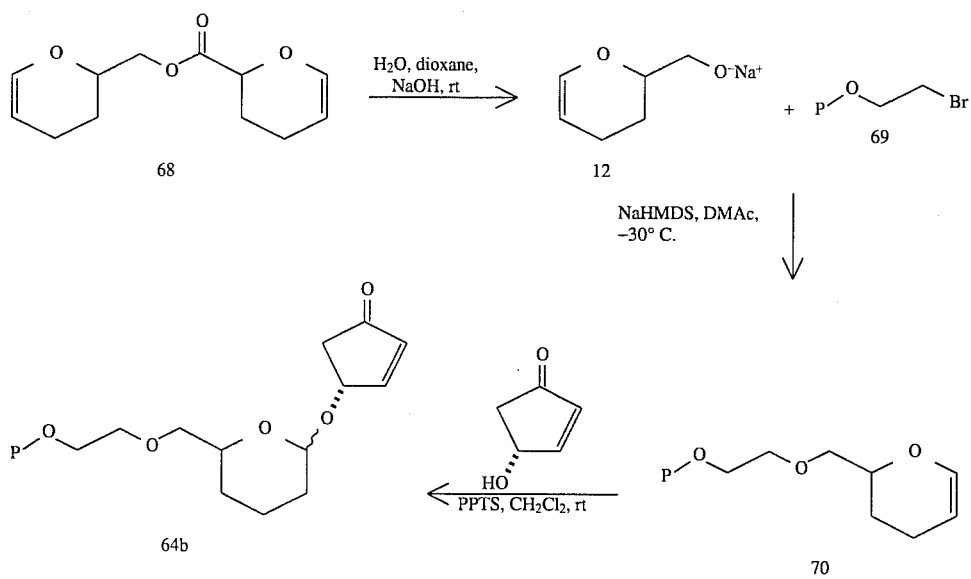

Referring back to Reaction Scheme IX, alkylation of 64a at the 4- and 5-positions on the pentenone ring is achieved by the well-known reaction with $R^E$CuLi (where $R^E$ is alkyl or substituted alkyl) under anhydrous conditions, inert atmosphere and low reaction temperatures, to form the intermediate enolate 65a, followed by reaction with an alkyl halide $R^F X$ (where $R^F$ is alkyl or substituted alkyl) to form the fully alkylated yet still immobilized prostaglandin derivative 66a (see March). The same reactions would be applied to 64b to obtain the corresponding products. Further manipulations can then be performed to extend the range of derivatives. Examples are reduction or addition of alkyl lithiums or Grignard reagents, olefination of the ketone functionality (by, e.g., using the Witting reaction), or modification of either or both of the alkyl side chains on the pentanone ring. For example, the side chains $R^E$ and $R^F$ may be later joined to form a ring adjacent the cyclopentane ring, or a new ring may be added using a Diels-Alder addition of butadiene derivative. Other manipulations will be apparent to those of skill in the art.

Cleavage of the prostaglandin derivative from the resin is readily achieved by treatment with a 3:1:1 mixture of acetic acid (HOAc), tetrahydrofuran (THF) and water to liberate the desired product 67.

Screening may then be performed in a manner analogous to that described above for the benzodiazepine derivatives.

B. Examples

The following generalized protocol follows Reaction Scheme IX. The protocol describes a solid-phase synthesis using a particulate resin. Translation of the protocol into a combinatorial synthesis and screening is achieved in the same manner described above in the benzodiazepine derivative examples.

General

Unless otherwise noted, all reagents were obtained from commercial suppliers and used without further purification. Pyridinium p-toluenesulfonate (PPTS) was prepared according to the procedure of Yoshikoshi (*J. Org. Chem.*, 1977, 42, 3772), and Jones' reagent was prepared according to the procedure of Djerassi (*J. Org. Chem.*, 1956, 21, 1547). Bis(cyclopentadienyl)zirconiumhydridochloride (Schwartz's reagent) was prepared according to the method of Buchwald (*Organic Syntheses* 1992, 71, 77). All solvents were distilled under nitrogen from the following drying agents immediately before use: Ether, tetrahydrofuran (THF), 1-4 dioxane, and 1,2-dimethoxyethane (DME) were distilled from sodium/benzophenone ketyl, dichloromethane ($CH_2Cl_2$), pyridine, and N,N-dimethylacetamide (DMAc) were distilled from calcium hydride, toluene was distilled from sodium, and ethanol was distilled from $Mg(OEt)_2$. All reagent solutions were handled under an inert nitrogen atmosphere using syringe and cannula techniques. All reactions unless otherwise noted were carried out in flame or oven dried glassware under inert nitrogen atmosphere. Thin-layer chromatography $R_f$ values were recorded on Merck 60 $F_{254}$ 0.25 micron silica gel plates, using cobalt nitrate/ammonium molybdate staining. Chromatography was carried out using Merck 60 230–400 mesh silica gel according to the procedure reported by Still (*J. Org. Chem.*, 1978, 43, 2923). The concentrations of commercially available alkyllithium reagents were periodically checked by titration with diphenylacetic acid (*J. Org. Chem.*, 1976, 41, 1879). Unless otherwise noted, all organic layers were dried over anhydrous $MgSO_4$, and all solvents were removed with a rotary evaporator under aspirator pressure. Gas chromatography data were obtained using a Hewlett-Packard 5890A Gas Chromatograph with a flame ionization detector and HP3393A integrator. Unless otherwise noted, IR spectra were recorded as thin films on NaCl plates and referenced against a polystyrene film. Chemical shifts in NMR spectra are expressed in ppm downfield from internal tetramethylsilane or relative to internal $CHCl_3$. J values are in Hertz. Mixtures of stereoisomers frequently had overlapping resonances in $^{13}C$ NMR spectra, so the correct number of resonances may not be shown. Stereoisomers are reported as isomers A and B.

1. Preparation of Functionalized Dihydropyran

The compound prepared by this procedure is the sodium salt of 2-hydroxymethyl-3,4-dihydro-2H-pyran, which is compound 62 of Reaction Scheme IX.

To a 0.2M solution of (3,4-dihydro-2H-pyran-2-ylmethyl)-3,4-dihydropyran-2H-pyran-2-carboxylate (a commercially available compound) in 2:1 dioxane/water is added 1.5 equivalents of 1N aqueous sodium hydroxide with stirring. The reaction is continued at ambient temperature until complete as confirmed by thin-layer chromatography (TLC). The solvents are then removed in vacuo and the residue is partitioned between 1N aqueous sodium carbonate solution and ethyl acetate. The organic layer is washed twice with sodium carbonate solution and once with aqueous sodium chloride solution, then dried over sodium sulfate and concentrated in vacuo to give the product. If necessary, the product can be purified by silica gel chromatography using ethyl acetate/hexane/triethylamine as eluent.

The compound prepared by this procedure is (3,4-Dihydro-2H-pyran-2-yl)methanol, which is compound 66 of Reaction Scheme X.

To a solution of 18.0 g (80.2 mmol) of (3,4-Dihydro-2H-pyran-2-ylmethyl) 3,4-dihydro-2H-pyran-2-carboxylate (65) in 90 mL of water and 30 mL of dioxane was added 4.95 g (124 mmol) of NaOH. The reaction solution was stirred 30 min, then extracted directly with ethyl acetate (3×150 mL). The combined organic layers were dried and evaporated to provide a yellow oil. Chromatography on 100 g of silica gel eluting with 2 L of 1:3 ethyl acetate/hexanes afforded 6.61 g (72%) of alcohol 66 as a colorless oil. IR: 3380, 2930, 1651 cm$^{-1}$. $^1$H NMR (400 MHz): d 1.63–1.73 (m, 1), 1.77–1.82 (m, 1), 1.94–2.02 (m, 1), 2.06–2.16 (m, 1), 2.79 (br s, 1), 3.62–3.71 (m, 2), 3.88–3.93 (m, 1), 4.68–4.72 (m, 1), 6.38 (d, 1, J=6.2). $^{13}$C NMR (101 MHz): d 19.3, 23.9, 65.2, 75.6, 100.8, 143.3. HRMS (EI): m/z calcd for $C_6H_{10}O_2$: 114.0681. Found: 114.0682.

2. Derivatization of a Solid-Phase Resins with the Functionalized Dihydropyran a. Polystyrene/Divinyl Benzene Solid Support The derivatized resin of this procedure is shown as structure 63 of Reaction Scheme IX.

Chloromethylated polystyrene resin (1% crosslinked divinylbenzene-styrene, 100–200 mesh, substitution levels 0.6–1.0 meq/g) is solvated in three volumes of freshly distilled tetrahydrofuran (from sodium/benzophenone ketyl) with slow stirring under positive nitrogen atmosphere in a flame-dried round bottom flask. In a separate flame-dried flask is added 2-hydroxymethyl-3,4-dihydro-2H-pyran (3.5 mole equivalents relative to meq of chloromethyl groups). The flask is then flushed with nitrogen, then maintained under a positive nitrogen pressure. Freshly distilled THF or dimethylacetamide is then added by syringe until a 0.2M concentration is reached. The solution is then cooled to −78° C. To this solution is added 2.0M n-butyl lithium in hexanes (3.0 mol equivalents relative to meq of chloromethyl groups), dropwise with stirring. The solution is stirred at −78° C. for 0.5 hour, then transferred by cannula with stirring to the solvated support precooled to −78° C. The resulting slurry is then allowed to warm to room temperature with stirring over 1–12 hours. The solution is removed by filtration cannula, and the support is washed once with THF, then three times with $CH_2Cl_2$, then dried in vacuo for 12 hours.

b. Coupling to the Tentagel-S Support

The derivatized resin of this procedure is shown as structure 68 of Reaction Scheme X.

Into a 50 mL round bottom flask was placed 1.00 g (0.27 mequiv) of Tentagel-S (Bromide) (Rapp Polymere, 100 mesh poly(styrene)block(polyethyleneglycol)) resin. The atmosphere was replaced with nitrogen, and the resin was solvated in 3 mL of DMAc. Into a separate flask was placed 92 mg (0.81 mmol) of alcohol 66 and 3 mL of DMAc. The flask containing alcohol 66 was chilled in a isopropanol/dry ice bath until the DMAc froze. As it melted and stirring became possible, 0.87 mL (0.87 equiv, 1.0M solution in THF) of sodium hexamethyldisilazide was added and the solution was stirred for 5 min. The resin slurry was then chilled until the DMAc froze, and as the solution thawed and stirring became possible, the solution containing the cold sodium anion of alcohol 66 was added via a cannula. The temperature of the system was increased to 25° C., and the slurry was stirred for 14 h. The resin was then washed with a solution of 1:1 N,N-dimethylformamide (DMF)/water (3×20 mL), pure DMF (3×20 mL), and $CH_2Cl_2$ (4×20 mL), and dried in vacuo (0.2 torr).

3. Coupling of 4-Hydroxycyclopent-2-en-one to Derivatized Resins a. Polystyrene/Divinyl Benzene Solid Support The coupled product of this procedure is shown as structure 64 of Reaction Scheme IX.

To a flame-dried round bottom flask fitted with stir bar is added the derivatized support prepared in the preceding section of this example and 5 mole equivalents of 4-hydroxycyclopent-2-en-one. After flushing with nitrogen, freshly distilled $CH_2Cl_2$ is added until the solution is 0.2–0.5M in hydroxycyclopentenone. Toluenesulfonic acid (0.05–0.5 mole equivalents) is added with stirring for 1–24 hours. The solution is then removed by filtration cannula, and the support is washed five times with $CH_2Cl_2$, then dried in vacuo.

b. Polystyrene-polyethyleneglycol (Tentagel-S) Solid Support

This is structure 68 of Reaction Scheme X.

To 500 mg (approx. 0.125 mmol) of linker derivatized resin was added 130 mg (1.30 mmol) of 4-hydroxy-2-cyclopentenone and 5 mL of 1,2 dichloroethane. To the slurry was added 65 mg of pyridinium p-toluene sulphonate as an acid catalyst, and the solution was heated at 60° C. for 14 h. The reaction solution was then drained from the resin, and the resin was washed with 3×DMF and 4×$CH_2Cl_2$. 4-Hydroxy-2-cyclopentenone was determined to be bound to the solid support by both $^{13}$C NMR and by FT IR analysis. $^{13}$C NMR: 163.3, 135.2, 97.5, 90.2, 42.5, 41.6, 29.5, 27.2, 17.5; IR (cm$^{-1}$ KBr) 1718 (C=O)

4. General Procedure for Cleaving a Prostaglandin from the Tentagel-S Support

The following is a general procedure for cleaving the product alcohol from the Tentagel-S support. To 600 mg of $PGE_1$ was added 20 mL of 3:1:1 acetic acid/$H_2O$/THF. The reaction temperature was raised to 40° C. and the slurry was stirred for 14 h. The solution was collected by cannula filtration, and the resin was washed with THF (3×20 mL). The combined solutions were concentrated in vacuo (1 torr) to provide 21 mg of the addition product as colorless crystals. Spectra were in excellent agreement with a commercial sample of $PGE_1$.

IV. β-Turn Mimetics

A. Description

A third example of a class of compounds to which the present invention may be applied are β-turn mimetics. These are compounds having molecular structures similar to β-turns which are one of three major motifs in a protein's molecular architecture. As one of the structural motifs, β-turns play a critical role in protein-ligand and protein-protein interactions. This role often takes the form of recognition between peptide hormones and their respective receptors. The development of a combinatorial library of β-turn mimetics will provide potential therapeutic agents whose activity is a result of the enhanced affinity between the β-turn structure and its receptor.

β-turns are loosely defined as a reverse in the direction of a peptide chain which takes place over four amino acid residues. A number of β-turns have been classified based on the geometries observed along the peptide backbone. Examples of a generic β-turn 71 and a generic β-turn mimetic 72 are shown below.

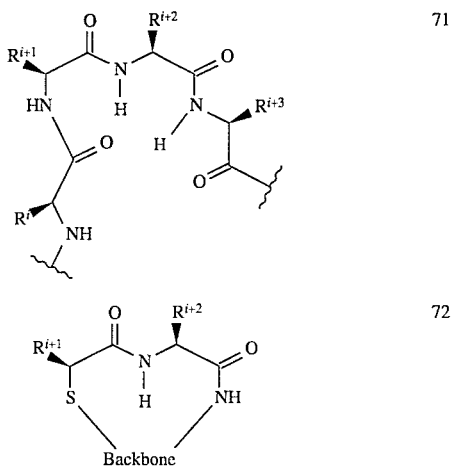

While orientation of side chains i+1 and i+2 is critical for receptor recognition, significant structural variations exist along the β-turn backbone which affect the relative orientations of these side chains. The vast number of spatial combinations possible for these side chains has resulted in tremendous difficulty in identifying the optimal structure of a β-turn mimetic for high affinity binding to a specific receptor. This problem can now be addressed by the synthesis and screening of a combinatorial library of β-turn mimetics which encompasses virtually all possible side-chain combinations and multiple orientations for each combination.

To apply the methods of this invention to β-turn mimetics 72, a solid-phase synthesis strategy has been developed, as outlined in Reaction Scheme XI.

REACTION SCHEME XI

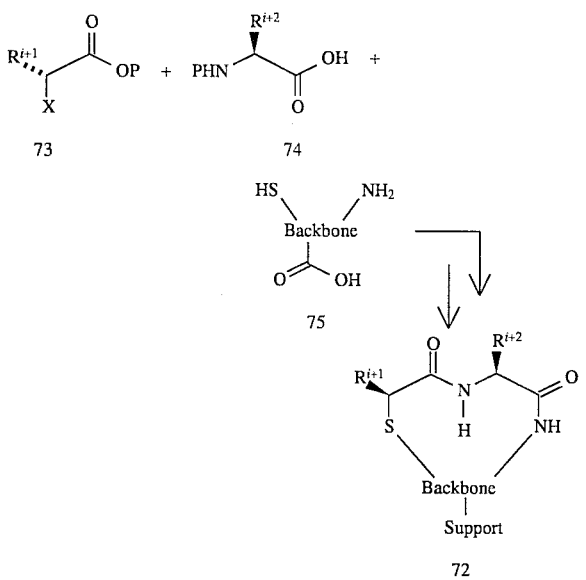

The components required to introduce the amino acid side-chains of the mimetic include the protected amino acids themselves 74 and α-halo acids or esters 73 which are available in one step from the corresponding amino acids or esters. See, Evans et al., *J. Am. Chem. Soc.* (1989) 111:1063–1072, and Koppenhoefer et al., *Organic Synthesis* (1987) 66:151–159, incorporated herein by reference. Utilizing both (R) and (S) enantiomers of components 73 and 74 increases the diversity in side-chain orientations which are synthesized. A third component 75 serves to define the geometry of the two side-chains and further provides a site for attachment to a solid support. Examples of readily available derivatives of component 75 are shown below.

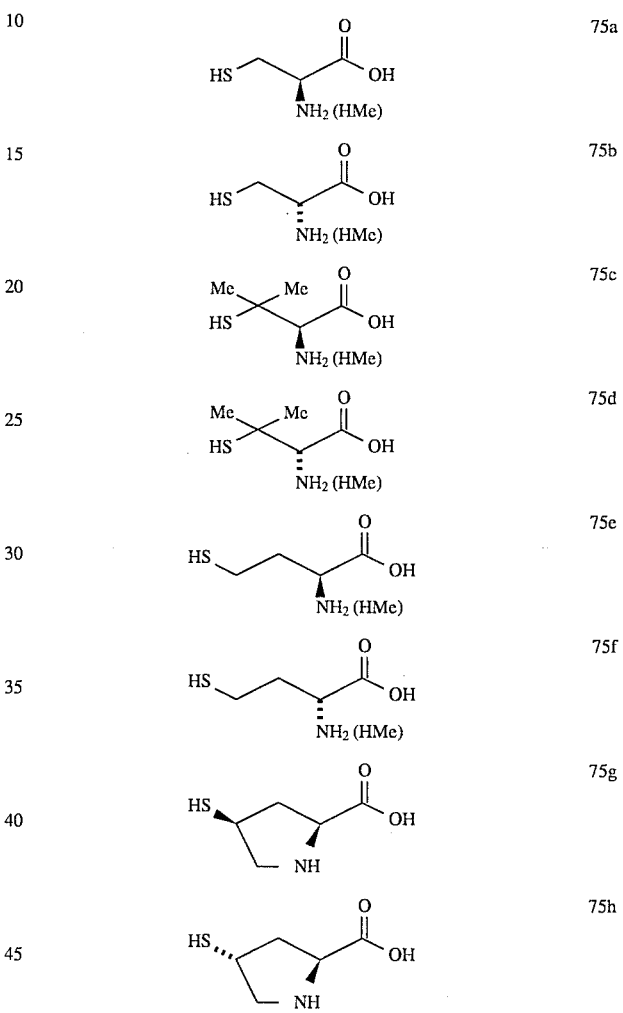

Preferred compounds of the formula 75 have the structure HS—CRR'(CH$_2$)$_n$CR"R'"— NH$_2$ where R, R', R" and R'" are selected independently from the group consisting of hydrogen, alkyl, substituted alkyl, aryl, substituted aryl, heteroaryl, substituted heteroaryl, alkoxy, amino, amido, or groups which together form an alkyl, aromatic or heteroaromatic ring, provided that one of R,R',R", or R'" is an carboxyl, activated carboxyl or acyl halide. Activated carbonyl is defined herein a carboxy group which includes a moiety known to activate the carboxyl carbon to nucleophilic attack. Examples of such groups are carbodiimides (e.g., diisopropylcarbodiimide). Preferred values of n are 0, 1, 2, and 3. Because many derivatives of each of the components 73–75 are available or can be synthesized in very few steps, a large combinatorial library based upon β-turn mimetics can be constructed rapidly and efficiently.

1. Solid Phase Synthesis of Class I β-Turns

A more complete synthesis route to 72 is shown in Reaction Scheme XII.

REACTION SCHEME XII

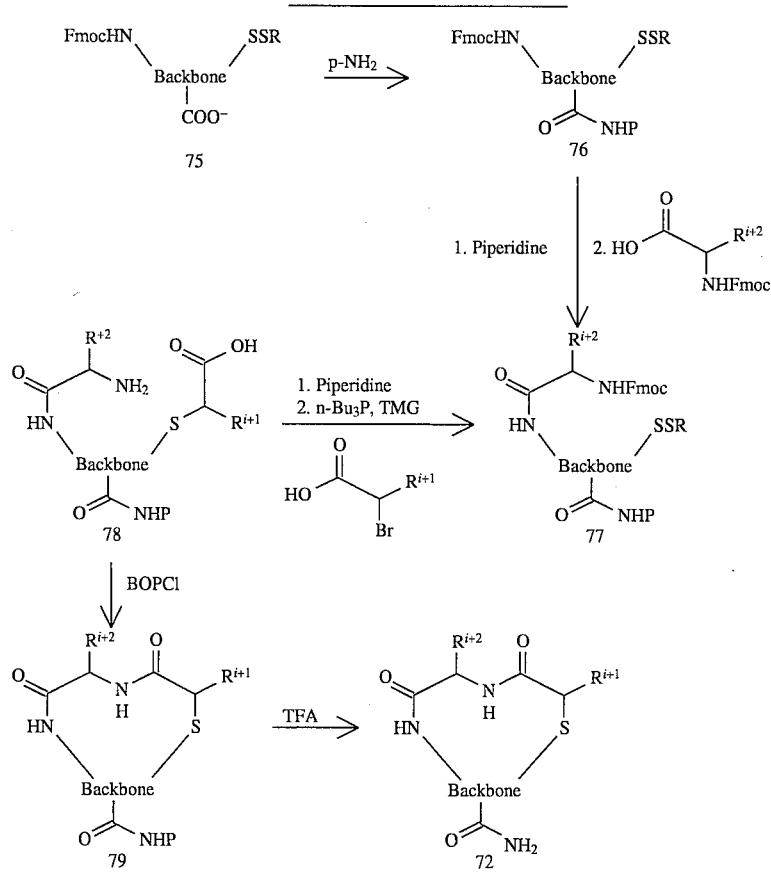

The particular couplings en route to 72 are all well precedented. Initial coupling of the backbone component 75, having the general formula $P_1S$—$CRR'(CH_2)_nCR''R'''$—$NHP_2$ where $P_1$ and $P_2$ are selected from the group consisting of thiol and amine protecting groups respectively; and R, R', R" and R''' are selected independently from the group consisting of hydrogen, alkyl, substituted alkyl, aryl, substituted aryl, heteroaryl, substituted heteroaryl, alkoxy, amino, amido, carboxyl, acyl or groups which together form an alkyl, aromatic or heteroaromatic ring, and n is 0, 1, 2, or 3, provided that at least one of R, R', R" and R''' is carboxyl or acyl, with a solid support to yield 76 can be achieved using amide forming reactions which are well known in the art. A preferred support is one comprising a polyethylene glycol and polystyrene block copolymer, such as that available from Millipore or Rappe Polymere (Tübingen, Germany) and described in Bayer, E., *Ang. Chem. Int. Ed., Eng.*, 1991, 30, 113–129. In structure 75, the amine and thiol are protected as the Fmoc-amine and disulfide, respectively; however, other means of protecting these functionalities will be apparent to those having skill in the art (see Green). Subsequent deprotection of the amine (by treatment with 20% piperidine in DMF) to form the free amine of 76 can be carried out without racemization of the chiral centers using the methods employed by several groups for similar alkylations. See, Benovitz et al., *Peptides* (1985) 6:648; Nicolaides et al., *J. Med. Chem.* (1986) 29:959–971 (1986); and Spatola et., *J. Org. Chem.* (1981) 46:2393–2394 (1981). The resulting free amine can then be coupled to an Fmoc-protected amino acid having the desired $R^{i+2}$ side chain using standard conditions to produce 77. Removal of the Fmoc protecting group is performed as described above. Reduction of the disulfide using known methods (e.g., n-Bu$_3$P and tetramethylguanidine (TMG)) and subsequent reaction with an s-halo acid having the desired $R^{i+1}$ side chain to form 78 is accomplished preferably by combining the phosphine and n-halo acid with 77 in a solvent mixture containing BuOH/DMF/H$_2$O in a preferred ratio of 5:3:2. Another preferred solvent mixture is one in which butyl alcohol is replaced with propyl alcohol. Other preferred reductants are dithiothreitol (DTT), mercaptoethanol, or sodium borohydride. Macrocyclization involving the amine and carboxylic acid functionalities of 78, using benzotriazole-1-yl-oxy-tris-pyrrolidinophosphonium hexafluror-phorosphate (PyBOP) as a carboxyl-activating agent as described by Felix et al., *Int. J. Pept. Protein Res.* (1988) 31:231–238 and 32:441–454, produces the solid supported β-turn mimetic 79. It will be appreciated by those of skill in the art that other well-known activating reagents such as carbodiimides and hydroxybenzotriazole (HOBT) may be used in place of PyBOP. Finally, removal of the desired class I β-turn mimetic 72 from the solid support is performed by exposing the bound product 79 to a trifluoroacetic acid/dimethyl sulfide solution. Each of the reference publications cited above is incorporated herein by reference.

Reaction Scheme XIII below illustrates a specific synthesis of a class I β-turn mimetic. Fmoc-protected L-homocystine 80 is attached to a solid support using the procedures just described. The Fmoc protecting groups were removed with 20% piperidine in DMF and the free amines were coupled with Fmoc-Phe—OPfp or Fmoc-(p-NO$_2$)-Phe—OPfp (OPfp=O-pentafluorophenyl) in dioxane/water solution containing diisopropylethylamine (DIEA) as a base to form 81a and 81b respectively. The disulfide and thioalkylation to form 82a and 82b were performed by treating the disulfides with excess tributylphosphine and (S)-2-propionic acid along with tetramethylguanidine in a solvent mixture of 5:3:2 PrOH/DMF/H₂O. Cyclization was performed with PyBOP as discussed above. ¹H NMR and FAB mass spectrum analysis of the product indicated that the major product was the cyclized monomer 83, although a small amount of dimer 84 was formed.

A combinatorial library of different combinations of the substituent groups $R^{i+1}$ and $R^{i+2}$ is developed in a manner analogous to that described above for the benzodiazepines and prostaglandins. Screening and cleavage are then likewise conducted in an analogous manner. For example, as described above with respect to the benzodiazepines, the support would comprise a plurality of amino-derivatized pins. Two or more Backbone structures would be coupled to said pins, and the support-bound Backbone structures would

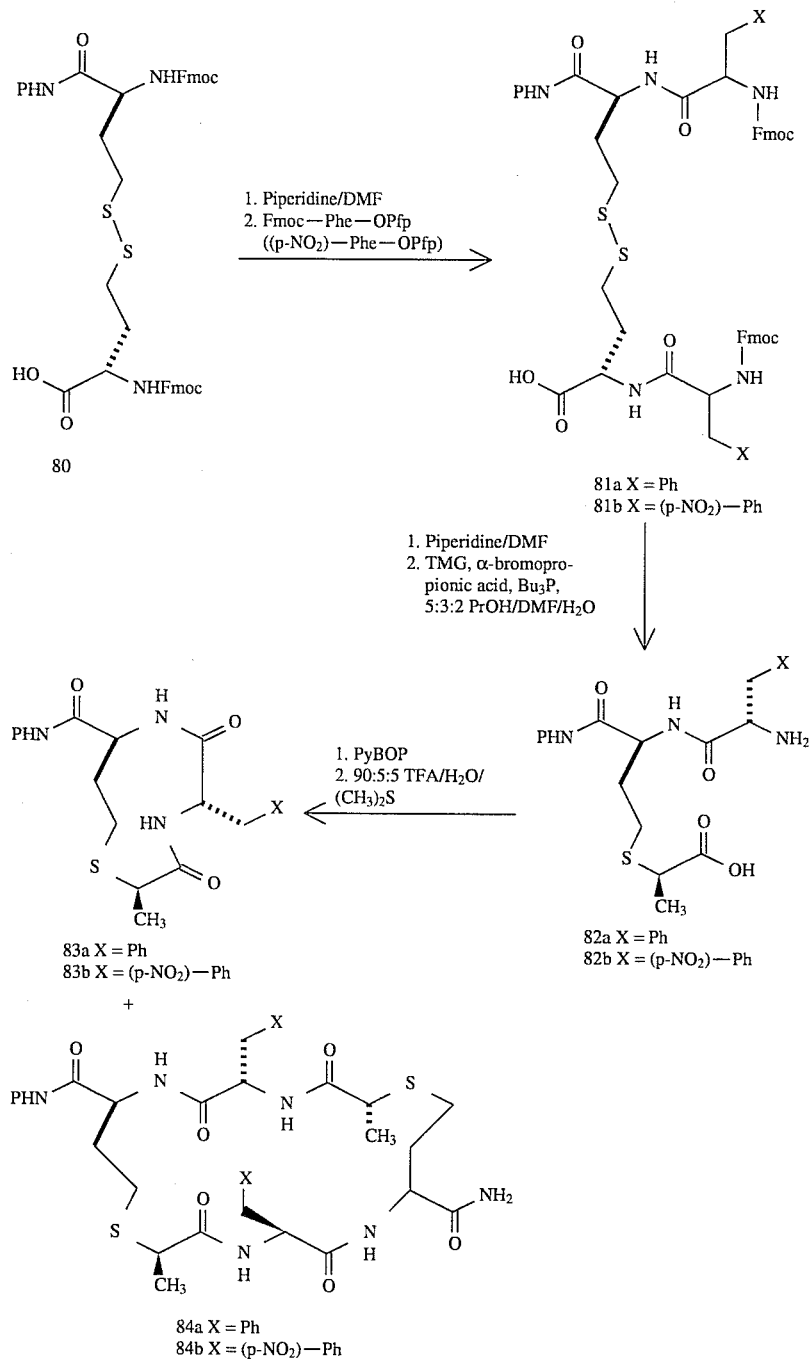

be reacted with a plurality of amino acid derivatives to produce a plurality of support-bound amides. The support-bound amides would next be reacted with a plurality of first amino acid derivatives after deprotection of the thiol functionality and cyclized to form bound β-turn mimetics which could be cleaved or assayed for biological activity while attached to the pins.

The synthetic route to class II β-turn mimetics is shown in Reaction Scheme XIV below. Class II β-turn mimetics are distinguished by a third side chain $R^{i+3}$. Thus, it will be appreciated that yet more combinatorial possibilities exist with class II turn mimetics as compared with class I turns. As shown in the Reaction Scheme, an α-bromo amide 90 is bound to a solid phase support using the standard conditions described by Zuckerman (*J. Am. Chem. Soc.*, 1992, 114, 10646–10647, which is incorporated herein by reference). Compound 90 carries the side chain $R^{i+3}$ of the β-turn. This is reacted with a Backbone-containing structure 91 having the general formula $P_1S$—$CRR'(CH_2)_nCR''R'''$—$NH_2$ where $P_1$ is a thiol protecting group, R, R', R" and R''' are selected independently from the group consisting of hydrogen, alkyl, substituted alkyl, aryl, substituted aryl, heteroaryl, substituted heteroaryl, alkoxy, amino, amido, or groups which together form an alkyl, aromatic or heteroaromatic ring, to form 92. A sample of preferred compounds having such structures is shown below. As discussed above, Backbone-containing structure 91 may include any of the protecting groups known in the art (disulfide protecting groups are illustrated here).

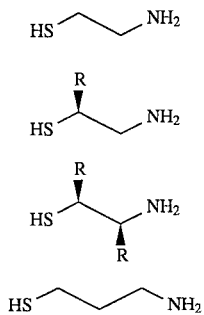

91a

91b

91c

91d

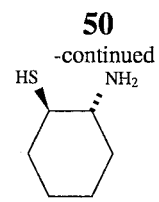

91e

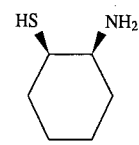

91f

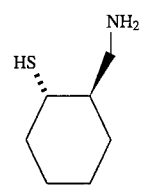

91g

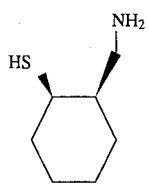

91h

Following the formation of 92, the next amino acid in the β-turn mimetic is added to form 93 by reacting the corresponding $N^\alpha$ -protected amino acid bearing the $R^{i+2}$ side chain using the steps described above for the class I turns (for example, activation of the carboxyl group, e.g., using BOPCl, followed by reaction with 92 in DMF). Deprotection of the amino moiety of 93, followed by deprotection and reduction of the sulfur protecting group, yields The addition of an $N^\alpha$-protected amino acid carrying the $R^{i+1}$ side chain, yields 95, which is cyclized under the conditions described above to form the desired β-turn mimetic 96.

REACTION SCHEME XIV

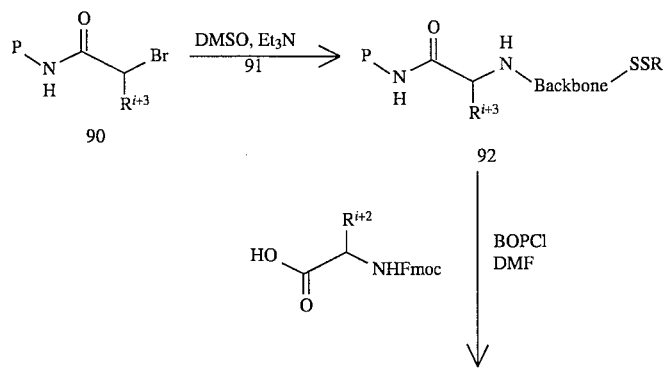

-continued
REACTION SCHEME XIV

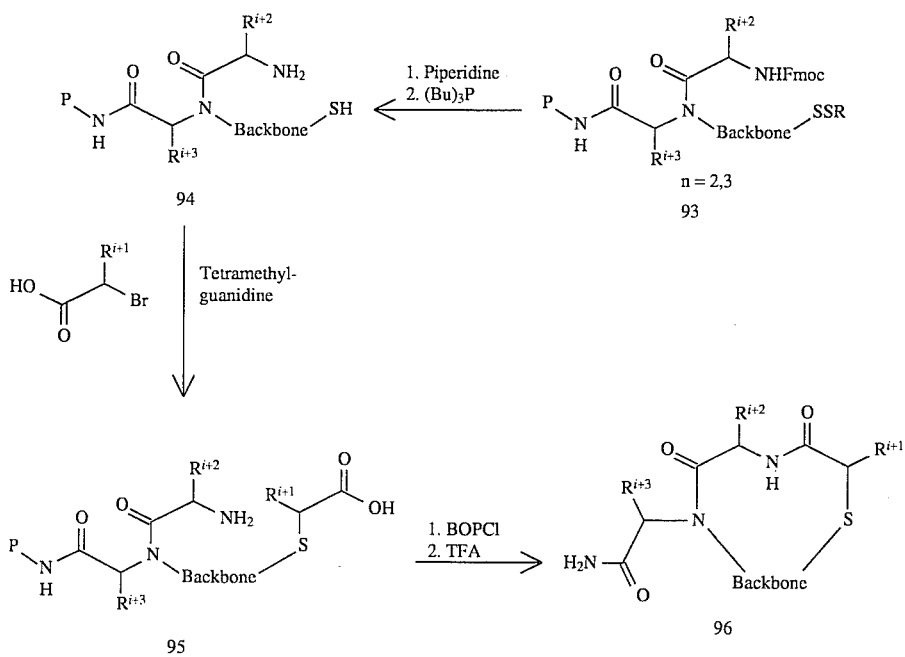

An variation of this pathway is shown in Reaction Scheme XV below. Compound 93 is reacted with the a-bromoamino acid bearing the $R^{i+1}$ substituent and DICI in pyridine to form intermediate compound a which differs from 94 only in that the thiol protection remains intact. Reaction of 94a with $Bu_3P$ and water, followed by reaction tetramethylguanidine and then TFA yields 96.

REACTION SCHEME XV

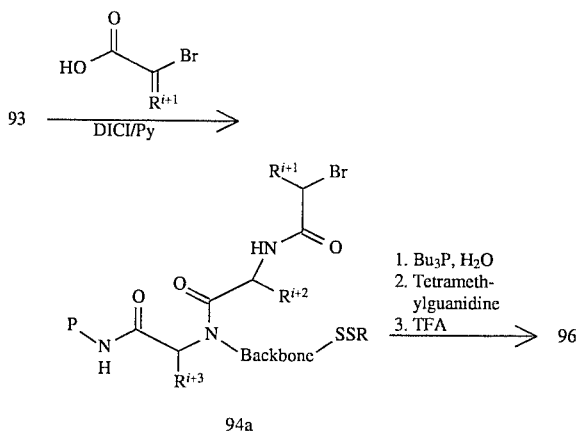

Reaction Scheme XVI illustrates the synthesis of two specific β-turn mimetics 105 (Backbone=—$(CH_2)_2$— and —$(CH_2)_3$—) following the sequence shown in Reaction Scheme XIV above. Support-bound α-bromo amide 100 is reacted with 1-mercapto-3-amino-propane or 1-mercapto-2-amino-ethane and triethyl amine in DMSO to form the secondary amine 101. The amine is coupled to Fmoc-protected p-nitrophenylalanine to make intermediate 102, whereupon the Fmoc group is cleaved with piperidine followed with and the disulfide protecting group is removed by reduction with tri-butylphosphine to form the thiol 103. Reaction of 103 with α-bromo propionic acid and tetramethylguanidine leads to 104. The cyclization and cleavage of 104 to form the desired mimetic 105 is performed by activating the carboxyl group with BOPCl, followed by reaction with TFA to cleave the cyclized mimetic from the solid support. These transformations are well documented in the art.

REACTION SCHEME XVI

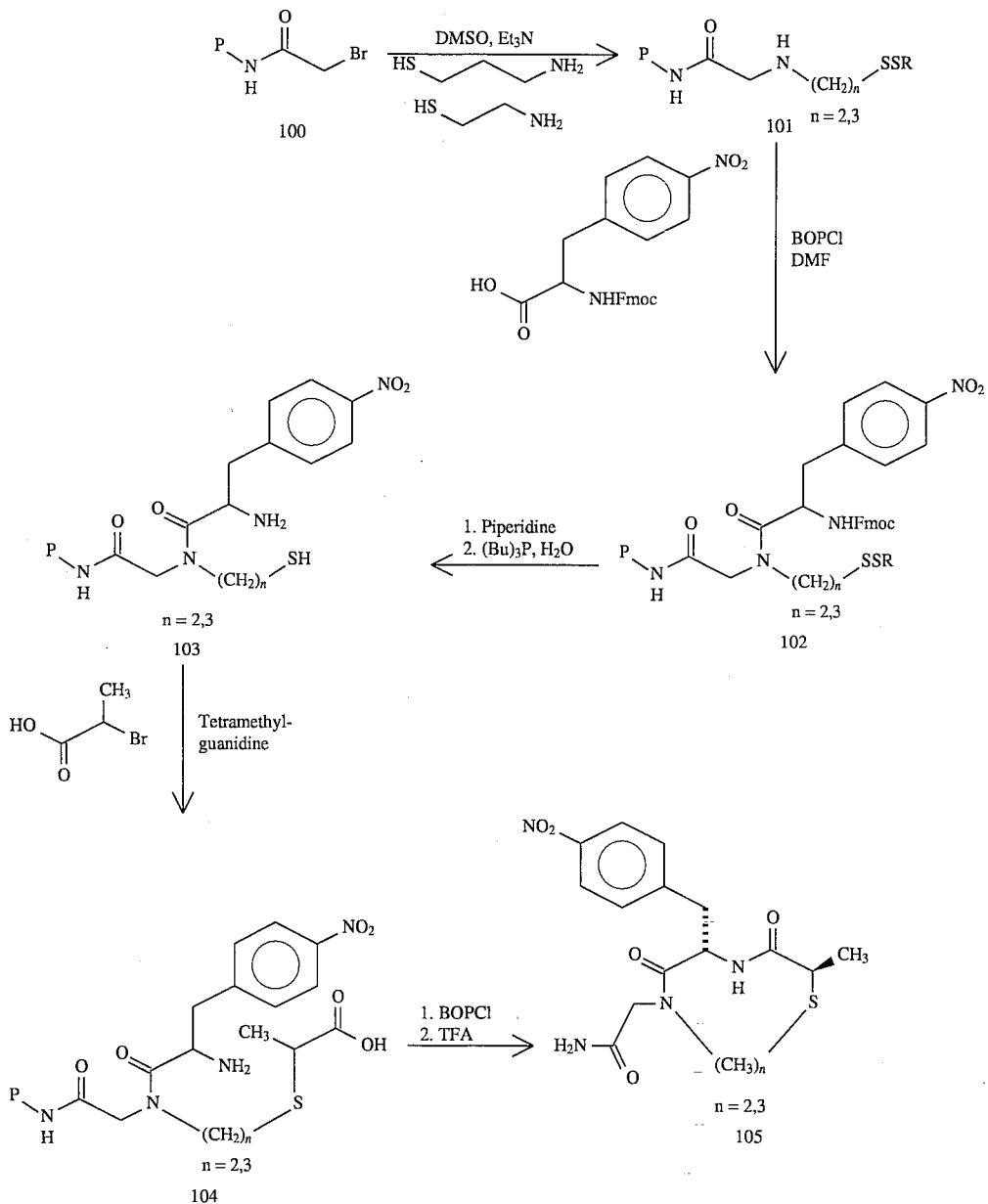

Three alternative pathways to intermediate 92 are feasible in addition to the sequence shown above. These alternatives are illustrated below in Reaction Scheme XVII. In the first alternative method, structure 110, the $N^\alpha$-Fmoc-protected amino acid bearing the $R^{i+3}$ side chain, is attached to a solid support using the standard techniques described above. This may be followed by reaction with trifluroracetic anhydride to form the trifluoroacetamide 111. Deprotonation of the trifluoroacetamide followed by reaction with a Backbone structure having the formula X—CRR'(CH$_2$)$_n$CR"R'"—NH$_2$ where X is a leaving group such as halogen, tosyl, or the like (see March), and R, R', R" and R'" are selected independently from the group consisting of hydrogen, alkyl, substituted alkyl, aryl, substituted aryl, heteroaryl, substituted heteroaryl, alkoxy, amino, amido, or groups which together form an alkyl, aromatic or heteroaromatic ring, yields structure 112. Reaction of 112 in basic medium, e.g., NaOH in water, removes both the trifluroracetamide and the disulfide to produce 92. Similarly, formation of bound element 110 may be followed by removal of the protecting group as described above followed by reaction with the just-described Backbone structure to yield 92 directly. Finally, 110 may be reacted with piperidine, again to remove the protecting group, followed by reaction with a Backbone structure having the formula H(O)C—CRR'(CH$_2$)$_n$CR"R'"—NH$_2$ where R, R', R" and R'" are selected independently from the group consisting of hydrogen, alkyl, substituted alkyl, aryl, substituted aryl, heteroaryl, substituted heteroaryl, alkoxy, amino, amido, or groups which together form an alkyl, aromatic or heteroaromatic ring, sodium cyanborohydride and acetic acid in DMF to form 92.

REACTION SCHEME XVII

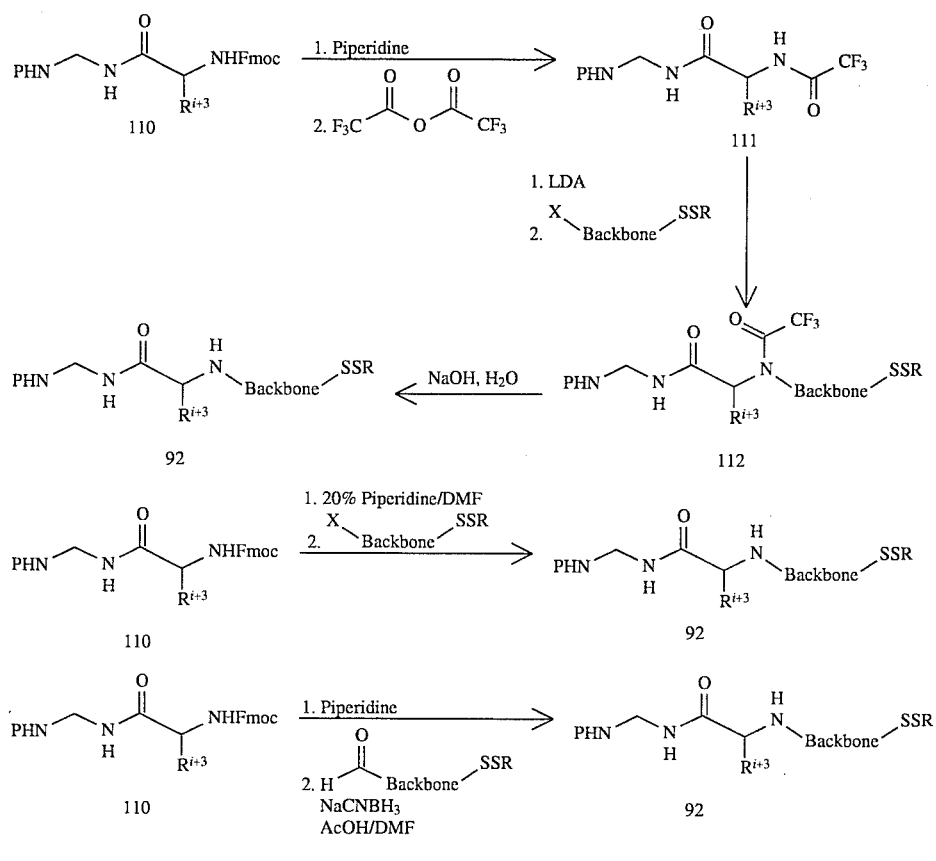

B. Examples

The following generalized protocol follows Reaction Scheme XIV. The protocol describes a solid-phase synthesis using a particulate resin. Translation of the protocol into a combinatorial synthesis and screening is achieved in the same manner described above in the benzodiazepine derivative examples.

General Conditions for Solid-Phase Chemistry

The support employed in solid-phase chemistry consisted of a polyethylene glycol-polystyrene (PEG-PS) block copolymer with loading levels of 0.17 and 0.26 milliequivalents (meq)/g and came protected as the amine hydrochloride salt. Liquid reagents and reaction solvents were added to the support via syringe and all solvents were removed from the support via filtration cannula. The support was rinsed for durations of 30 seconds unless otherwise indicated. Fmoc protecting groups on support-bound compounds were removed according to the general procedure detailed below. To the support, 20% piperidine in DMF (10 mL/g of the support) is added and allowed to react for 1 minute, then drained. An equivalent volume of 20% piperidine in DMF is added and the reaction is allowed to proceed for 20 min to ensure complete deprotection. The solvent is drained and the resin is rinsed with DMF (4×10 mL) and $CH_2Cl_2$ (5×10 mL). The Kaiser ninhydrin test was performed as described below. To a small aliquot (10 mg) of resin in a test tube is added several drops of each of the following solutions: KCN in pyridine (20 mM), ninhydrin in EtOH (500 mg/10 mL), and phenol in EtOH (8 g/2 mL). The test tube is heated at 70° C. for several minutes and a positive result is indicated by an intense blue color. The substitution level of the support-bound material was determined by spectrophotometric analysis of the Fmoc-chromophore according to the procedure described by Milligen.1 Briefly, a known amount (several mg) of dry resin is deprotected in 0.4 mL of piperidine and 0.4 mL of $CH_2Cl_2$. After 30 min, 1.6 mL of MeOH and 7.6 mL of $CH_2Cl_2$ are added to bring the total volume to 10 mL. The absorption at 301 nm relative to a blank (prepared with the above reagents without the addition of resin) is used to calculate the substitution level according to the equation: $meq/g=(A_{301}/7800)\times(10$ mL/g of resin). The linkage of support-bound material was severed and the compounds were liberated as primary amides by the addition of and reaction with 10 mL of 90:5:5 $TFA/H_2O/Me_2S$ for 1–3 h. Cleaved material was collected by draining the solvent and combining it with subsequent rinses with $CH_2Cl_2$ (1×10 mL), and 1:1 $CH_2Cl_2/MeOH$ (2×10 mL), and then concentrating in vacuo.

Construction of Class I Turns

1. Coupling the Backbone to the Support

The structure prepared in this procedure is structure 76 of Reaction Scheme XI.

A peptide reaction flask is charged with aminomethyl resin (1.91 g, 1.51 mmol of crosslinked divinylbenzene-styrene, 200–400 mesh size, substitution level 0.79 milliequivalents/g), two equivalents of an S-fluorenylmethyl protected, N-fluorenylmethoxycarbonyl protected cysteine analog (having the structure of the desired backbone), and hydroxybenzotriazole (2.2 equivalents). Anhydrous DMF is then added to provide a solution 0.2–0.4M in the protected cysteine derivative. The resulting mixture is vortexed for 0.5 hour to fully solvate the resin. Either diisopropylcarbodiimide or benzotriazol-1-yl-oxy-tris(dimethylamino)-phosphonium hexafluorophosphate (2.2 equivalents) is then added by syringe. The reaction flask is stoppered and then vortexed until the Kaiser ninhydrin test on approximately 10 mg of the solid support demonstrates that coupling is complete (approximately 24 hours). The solvent and agents are then filtered away from the solid support and the support is rinsed five times with 20 mL dimethylformamide and five times with 20 mL $CH_2Cl_2$, then dried in vacuo for 12 hours.

2. Removal of the Protecting Groups from the Support-Bound Backbone (76) and Coupling to the α-Amino Acid and the α-Halo Acid This procedure results in structure 78.

The product of the Section 1 of this example is added to a round bottom flask fitted with stir bar and filtration cannula. The flask is flushed with nitrogen, and then degassed 50% piperidine in DMF is added by the cannula. The resulting slurry is stirred for 2–24 hours at ambient temperature, and the solution is then removed by the cannula. The support is then washed five times with DMF, following which a degassed 0.2–0.5M solution of 10 equivalents of sodium phenoxide or ethoxide in 2:1 ethanol/DMF is added. The appropriate protected α-amino acid (5 mole equivalents) is then added, with stirring. The resulting slurry is stirred under a nitrogen atmosphere for 1–24 hours. The solution is then removed by the cannula, and the support is washed with 5% acetic acid in DMF, followed by three times with DMF and twice with $CH_2Cl_2$. The support-bound intermediate (structure 77) is then diluted with a solution 0.2M in the pentafluorophenyl ester of the appropriate Fmoc-protected n-halo acid and 0.2M in diisopropylethylamine in DMF. The resulting mixture is stirred until the Kaiser ninhydrin test shows that a free amine is no longer present (2–24 hours). The solution is then removed by the cannula and the support is washed three times each with DMF and $CH_2Cl_2$. The support-bound intermediate (structure 78) prepared above is treated with 20% piperidine in DMF for twenty minutes. This results in support-bound intermediate 79.

3. Cyclization to the β-Turn Mimetic

The solution containing 79 is removed by the cannula, and the remaining support is washed five times each with DMF and $CH_2Cl_2$. Cyclization is then performed by adding a 0.025–0.2M solution of benzotriazol-1-yl-oxy-tris(dimethylamino)-phosphonium hexafluorophosphate (BOPCl) in DMF and stirring for 4–12 hours, followed by removal of the solution by the cannula. The BOPCl solution is then added again, stirring is continued for another 4 hours and the solution removed. This process is repeated until no free amines are observed as indicated by a Kaiser test. The result is the support-bound product 72.

4. Coupling of the 4-[(R,S)1-[1-(9H-Fluorenyl-9-yl)- methoxycarbonylamino]-(2',4'-dimethoxybenzyl]-phenoxyacetic Acid Linker to Support Dry support (aminomethyl-substituted polyethylene glycol and polystyrene block copolymer purchased from Rapp Polymere, Tübingen, Germany) (5.0 g, 0.17 meq/g, 0.85 meq) was washed with DMF (1×20 mL), $CH_2Cl_2$ (1×20 mL), 5% (i -Pr)$_2$EtN in $CH_2Cl_2$ (3×20 mL), DMF (1×20 mL), and $CH_2Cl_2$ (2×20 mL) to obtain the free base. The linker, 4-[(R,S)-1-[1-(9H-Fluorenyl-9-yl)-methoxycarbonylamino]-(2',4'-dimethoxybenzyl]-phenoxyacetic acid, (0.92 g, 1.70 mmol) was coupled to the support solvated in 17 mL of DMF by the addition of 260 mg (1.70 mmol) of HOBt·1 $H_2O$ and 266 ml (1.70 mmol) of DICI. After 12 h, the reaction solvent was drained and the resin was rinsed with DMF (4×20 mL) and $CH_2Cl_2$ (5×20 mL). A negative ninhydrin test was observed and the substitution level was determined to be 0.12 meq/g (77%). Coupling of the linker to the support was repeated for another batch of resin (5.00 g, 0.26 meq/g, 1.30 mmol). The amount of reagents used was increased by a factor of 1.53. A negative ninhydrin test was observed and the substitution level was determined to be 0.20 meq/g (88%). All mention of support hereinafter refers to linker-functionalized support.

5. N,N'-Di[(9-fluorenylmethoxy)carbonyl]-L-homocystine (80)

A suspension of 3.00 g (11.0 mmol) of L-homocystine in 40 mL of dioxane was stirred vigorously before the addition of 5.68 mL (45.0 mmol) of TMS-Cl. The reaction slurry was stirred 2 h before dilution with 80 mL of $CH_2Cl_2$ and subsequent cooling in an ice-water bath. To the cooled solution was added 6.21 g (24.0 mmol) of Fmoc-Cl and 7.84 mL (45.0 mmol) of (i -Pr)$_2$EtN. After 12 h, the appearance of the reaction mixture had changed from a milky-white to a dark yellow but remained opaque. The mixture was concentrated in vacuo and distributed between 150 mL of EtOAc and 150 mL of aqueous 1M HCl. The layers were separated and the EtOAc layer was washed with aqueous 1M HCl (3×40 mL). The combined aqueous layers were extracted with EtOAc (3×40 mL). The organic layers were then combined, concentrated in vacuo, and the resultant material was suspended in 50 mL of hot acetone and filtered. The filtrate was transferred to a Buchner filtration funnel, washed with aqueous 1M HCl (2×25 mL), $H_2O$ (2×25 mL), and ether (2×25 mL), and dried in vacuo to yield 2.55 g of a white solid, mp 213°–214° C. The combined washes were concentrated in vacuo and rinsed as above to yield a second crop of 1.23 g (48% combined yield). IR (KBr pellet): 3310, 3000 (br), 1710 (br), 1520 $cm^{-1}$. $^1H$ NMR (500 MHz, $d_6$-DMSO): d 1.94–1.96 (m, 2), 2.10–2.12 (m, 2), 2.71–2.76 (m, 4), 4.07–4.09 (m, 2), 4.21 (t, 2, J=7.0), 4.29 (d, 4, J=5.9), 7.31 (t, 4, J=7.4), 7.40 (t, 4, J=7.4), 7.70 (d, 4, J=7.1), 7.87 (d, 4, J=7.6). $^{13}C$ NMR (101 MHz, $d_6$-DMSO): d 30.3, 34.0, 46.7, 52.5, 66.0, 120.1, 125.2, 127.0, 127.6, 7140.7, 143.8, 158.1, 173.4. Anal. Calcd for $C_{38}H_{36}N_2O_8S_2$: C, 64.03; H, 5.09; N, 3.93. Found: C, 63.67; H, 5.21; N, 4.01.

6. Synthesis of β-turn Mimetic (83a)

Dry support (1.0 g, 0.20 mmol) was rinsed with DMF and then the FMOC group was removed with 20% piperidine in DMF according to the general experimental procedure. Diprotected 80 (370 mg, 0.52 mmol) was then coupled to the support in 5.2 mL of DMF by the addition of 80 mg (0.52 mmol) of HOBt·1 $H_2O$ and 81 mL (0.52 mmol) of DICI. The coupling was allowed to proceed 12 h and the solvent was drained and the resin was rinsed with DMF (4×10 mL) and $CH_2Cl_2$ (5×10 mL). A negative ninhydrin test was observed and the substitution level was determined to be 0.20 meq/g (100%). To the support-bound 80 (2.05 g, 0.41 mmol), prepared as described above, was added a solution of 1.11 g (2.0 mmol) of Fmoc-Phe—OPfp in 20 mL of 90:10 NMP/$H_2O$ followed by 174 mL (1.0 mmol) of (i -Pr)$_2$EtN. After 12 h, the solvent was drained and the resin was rinsed with DMF (5×10 mL) and $CH_2Cl_2$ (5×10 mL). A negative ninhydrin test was observed. The Fmoc protecting group of 81a was removed and the support-bound material was solvated in 30 mL of 50:30:20 BuOH/DMF/$H_2O$ and the solution was deoxygenated. Under $N_2$, 270 mL (3.0 mmol) of (S)-2-bromopropionic acid and 564 mL (4.5 mmol) of tetramethylguanidine were added. The reaction vessel was sealed under an atmosphere of $N_2$ with a rubber septum. After 12 h, the solution was drained and the resin was rinsed with 1:1 DMF/$H_2O$ (2×10 mL), DMF (2×10 mL), and $CH_2Cl_2$ (4×10 mL) to give 82a. Half of the support-bound material 82a (1.00 g, 0.20 mmol) was carried on to cyclization. The resin was rinsed with DMF (1×15 min) and solvated in 20 mL of DMF. Cyclization was initiated by the addition of 300 mL (1.5 % v/v) of (i-Pr)$_2$EtN and 312 mg (0.60 mmol) of PyBOP. Ninhydrin tests performed at 2, 4, 6, 12, and 18 h were used to monitor the progress of the reaction. A negative ninhydrin test was observed after 18 h and the reaction was stopped. The solvent was drained and the resin was rinsed with DMF (4×10 mL) and CH$_2$Cl$_2$ (5×10 mL). The material was cleaved from the support and collected. The impure material was dissolved in 5 mL of 1:1 CH$_2$Cl$_2$/MeOH and the precipitate was removed by filtration. The filtrate was concentrated and analyzed by TLC to reveal one major band (Rf=0.25 using 90:10:1 CH$_2$Cl$_2$/MeOH/40% aqueous NH$_4$OH). Spectral analysis indicated that cyclic material was obtained, but the distinction between monomer 83a and dimer 84a could not be made. $^1$H NMR (500 MHz, d$_6$-DMSO): d 1.06 (d, 3, J=7.0), 1.98–2.04 (m, 1), 2.17–2.23 (m, 1), 2.35–2.40 (m, 2), 2.77 (dd, 1, J32 8.8, 13.8), 2.98 (dd, 1, J=5.7, 13.8), 3.44–3.49 (m, 1), 4.16–4.18 (m, 1), 4.58 (q, 1, J=6.2), 6.65 (s, 1), 7.03 (s, 1), 7.16 (t, 1, J=6.9), 7.20–7.28 (m, 4), 8.11 (d, 1, J=7.8), 8.35 (d, 1, J=8.4). HRMS (EI): exact mass calcd for C$_{16}$H$_{22}$N$_3$O$_3$, 335.1303, found 335.1302.

7. [(9-Fluorenylmethoxy)carbonyl]-O-pentafluorophenyl-p-nitro-L-phenylalanine

Nitro-L-phenylalanine (5.00 g, 22.0 mmol) was Fmoc-protected with 11.1 mL (88.0 mmol) of TMS-Cl, 7.66 mL (44.0 mmol) of (i-Pr)$_2$EtN, and 6.23 g of (24.1 mmol) of Fmoc-Cl in 50 ml of CH$_2$Cl$_2$ using standard techniques. The mixture was then concentrated in vacuo and acidified by the addition of concentrated HCl in the presence of 150 mL of H$_2$O and 75 mL of EtOAc. The aqueous layer was extracted with EtOAc (3×75 mL). The organic extracts were combined and the material which had precipitated was collected by filtration (4.02 g upon drying). The filtrate was concentrated in vacuo, suspended in EtOAc, and refiltered to recover a second crop of 0.70 g (50% combined yield) of Fmoc-(p-NO$_2$)-L-Phe which was used without further purification. To an ice-cold solution of 2.27 g of DCCI (11.0 mmol) in 35 mL of dioxane was added 3.68 g (20.0 mmol) of pentafluorophenol followed in about 5 min by the addition of 4.34 g (10.0 mmol) of Fmoc-(p-NO$_2$)-L-Phe suspended in 15 mL of dioxane. The reaction flask remained on ice and was stirred for 12 h with gradual warming to rt. The solution was filtered to remove N,N'-dicyclohexylurea which had precipitated. The filtrate was then concentrated in vacuo to afford impure material which was purified by flash-chromatography on 300 g of silica gel with 70:30 hexanes/EtOAc (2 L) to afford 3.14 g (44% from Fmoc-(pNO$_2$)-L-Phe, 22% overall) of a white, flaky solid, mp 143°–145° C. IR (KBr pellet): 1795, 1710 (br), 1520 cm$^{-1}$. $^1$H NMR (500 MHz, CDCl$_3$): d 3.30 (dd, 1, J=6.5, 14.0), 3.42 (dd, 1, J=5.8, 14.0), 4.20 (t, 1, J=6.3), 4.48 (dd, 1, J=6.4, 10.5), 4.55 (dd, 1, J=6.7, 10.5), 5.02–5.06 (m, 1), 5.21 (d, 1, J=8.2), 7.26–7.37 (m, 4), 7.41 (t, 2, J=7.4), 7.54 (d, 2, J=7.5), 7.78 (d, 2, J=7.5), 8.16 (d, 2, J=8.3). $^{13}$C NMR (101 MHz, CDCl$_3$): d 37.7, 47.1, 54.2, 67.5, 120.0, 123.9, 124.8, 127.1, 127.9, 130.2, 141.4, 142.1, 143.0, 147.2, 155.6, 196.3. Anal. Calcd for C$_{30}$H$_{19}$N$_2$O$_6$F$_5$: C, 60.21; H, 3.20; N, 4.68. Found: C, 60.43; H, 3.08; N, 4.51.

8. Synthesis of β-turn Mimetic (83b)

The β-turn mimetic 83b was synthesized identically according to the synthesis of 83a above substituting Fmoc-(pNO$_2$)-L-Phe for Fmoc-L-Phe. HPLC analysis (Rainin Dynamax, Microsorb 5 mm C18 column with UV detection at 274 nm) with a 40 min elution gradient from 30% MeOH in H$_2$O to 80% MeOH in H$_2$O revealed two compounds (t$_R$=13.79 min, area=91.4%; t$_R$=20.90 min, area=4.57%) postulated to be the monomer 83b and dimer 84b, respectively. Preparative HPLC employing a Rainin Dynamax, Microsorb C18 column provided purified material. $^1$H NMR (400 MHz, d$_6$-DMSO, 150° C.): d 1.28 (d, 3, J=6.9), 1.81–1.90 (m, 1), 2.11–2.19 (m, 1), 2.55–2.61 (m, 2), 3.14 (dd, 1, J=8.4, 14.5), 3.35 (dd, 1, J=6.4, 14.9), 3.51 (q, 1, J=6.9), 4.27–4.36 (m, 1), 4.50–4.58 (m, 1), 6.64 (br s, 2), 6.85 (br s, 1), 7.54 (d, 2, J=8.6), 7.97 (br s, 1), 8.09 (d, 2, J=8.6). HRMS (FAB): exact mass calcd for C$_{16}$H$_{21}$N$_4$O$_5$ (MH$^+$) 381.1234, submitted (found 381.0 LRMS).

Synthesis of Class II Turn Mimetics

1. Coupling the α-bromo Acid (i+3 residue) to the Solid Support

The resin coupled with the 4-[(R,S)-1-[1-(9H-Fluorenyl-9-yl)methoxycarbonylamino]-(2',4'-dimethoxybenzyl]-phenoxyacetic Acid linker prepared as described above was solvated with DMF and then the FMOC protecting group was removed by treatment with 20% piperidine in DMF according to the general procedure. A solution of 0.3M solution of bromoacetic acid (6 equiv) in DMF was added to the resin followed by 6.6 equiv of diisopropyl carbodiimide. The coupling was allowed to proceed for 12 h. After the solvent was drained the resin was rinsed with DMF (x) and CH$_2$Cl$_2$ (x5). If ninhydrin tests indicates that the reaction is not complete then the coupling reaction is repeated.

2. Introduction of the Backbone Component

The resin prepared above is washed once with DMF and once with DMSO. Then, a solution of the backbone element, containing a free amine or amine hydrochloride and a thiol protected as a disulfide, (>5 equiv) as a 1.0M solution in DMSO is added to the solid support followed by addition of tetramethylguanidine (>5 equiv) as a 1.0M solution in DMSO. The resulting mixture is stirred at room temperature for 24 h. After the resin is drained, the resin is rinsed with DMF (4x) and CH$_2$Cl$_2$ (4x).

3. Introduction of the PMOC-protected Amimo Acid (the i+2 Side-chain)

Dry resin from the step above is rinsed with DMF (2 x). To the resin is then added a DMF soln that is 0.33M in FMOC protected amino acid (>5 equiv), 0.33 M in PyBOP (>5 equiv), 0.15M in hydroxybenzotriazole (>5 equiv) and 0.66 M in diisopropylethylamine (>10 equiv). The reaction was stirred overnight at room temperature. After draining rxn soln, resin was rinsed with DMF (4x) and with CH$_2$Cl$_2$ (4x). If ninhydrin test shows no free amine carried on to next step, if the tests indicates that there is free amine then the reaction is repeated.

4. Thiol Alkylation With an α-bromo Acid (Introduction of the i+1 Residue)

The FMOC protecting group was removed under standard conditions. The resin was then solvated in a comixture of 5:3:2 n-propanol/DMF/H$_2$O. The slurry is deoxygenated by bubbling N$_2$ through the slurry for 20 min. The following reagents are then added in the order listed: tributylphosphine (>5 equiv, a final concentration of 0.1M), a-bromo acid (>5 equiv, a final concentration of 0.1M), and tetramethylguanidine (>7.5 equiv, a final concentration of 0.1M). The reaction was stirred overnight under N$_2$, and then the reaction mixture was diluted with approx. one volume of H$_2$O, and then drained. The resin was then rinsed with DMF (4x) and CH$_2$Cl$_2$ (4x).

5. Cyclization to Provide the Support-bound β-turn Mimetic

The resin was rinsed with DMF, and then solvated in DMF. Cyclization was initiated by addition of PyBOP (>5 equiv, a final concentration of 0.03M) and diisopropylethylamine 1.5% volume/volume. After stirring overnight the reaction solution is drained and the support is rinsed with DMF (4x) and with $CH_2Cl_2$ (4x). If the ninhydrin test is positive the reaction is repeated until a negative test is observed.

6. Cleavage of the β-Turn from the Resin

Product is cleaved from the resin by addition of 10 mL of the following cleavage cocktail: 7/3/0.5/0.5 trifluoroacetic acid/$CH_2Cl_2$/$H_2O$/dimethyl sulfide followed by stirring for approx. 6 h. The cleavage solution was then combined with resin rinses, 1×$CH_2Cl_2$, and 2×$CH_2Cl_2$ and methanol comixture, and concentrated in vacuo. Purification by preparative reverse phase HPLC employing a Rainin 22 mm×25 cm C18 column provided pure cyclic monomer and pure cyclic dimer as the two predominate products.

V. Glycerol-Based Compounds

A. Description

The techniques of the present invention lend themselves naturally to the synthesis of substances having a glycerol-based framework. Over 11,000 such compounds were reported in the chemical literature between 1980 and 1990 alone. These compounds include: andrenergic receptors used to treat glaucoma, hypertension, arrhythmia, and angina, phospholipase $A_2$ inhibitors, radiosensitisors, HIV protease inhibitors, 5-lipoxygenase inhibitors, bactericidal antirust agents and mesogenic materials.

Reaction Scheme XVIII illustrates the general approach to synthesizing a combinatorial library of glycerol-based compounds on a solid support, such as beads or pins. Starting with support-bound pyranyl-glycerol derivative 120, having derivatized hydroxyl groups $P_1O$- and $P_2O$-, a first reagent $Nu_1$ may be substituted for $P_1O$- as shown in structures 121 or the $P_1O$- group may first be oxidized, so that reaction with $Nu_1$ leads to the addition product 122. These steps may be performed using techniques which are known in the art. See, Hanson, R. M., *Chemical Reviews*, 1991, 91, p. 437, which is incorporated by reference. Similarly, a second nucleophile $Nu_2$ may be substituted for $P_2O$- or added to the oxidized compound to form compounds 123–127. Cleavage from the substrate under conditions substantially as described above leads to the free compounds (not shown). Preferred nucleophiles include alkoxides, phenoxides and amines.

The extension of these reactions to the synthesis of diverse compounds attached to a solid support is analogous to the descriptions provided above. Attachment of compound 100, and/or its oxidized analog, to amino-derivatized pins would follow substantially the procedures described above. The bound structures may then be reacted with a plurality of first nucleophiles to form various bound substitution and/or addition variants using standard chemical transformations. These compounds may be derivatized further by oxidation and/or reaction with a second nucleophile to produce still more substituted glycerol derivatives, again using standard chemical transformations. The final products may then be removed from the support on assayed in situ.

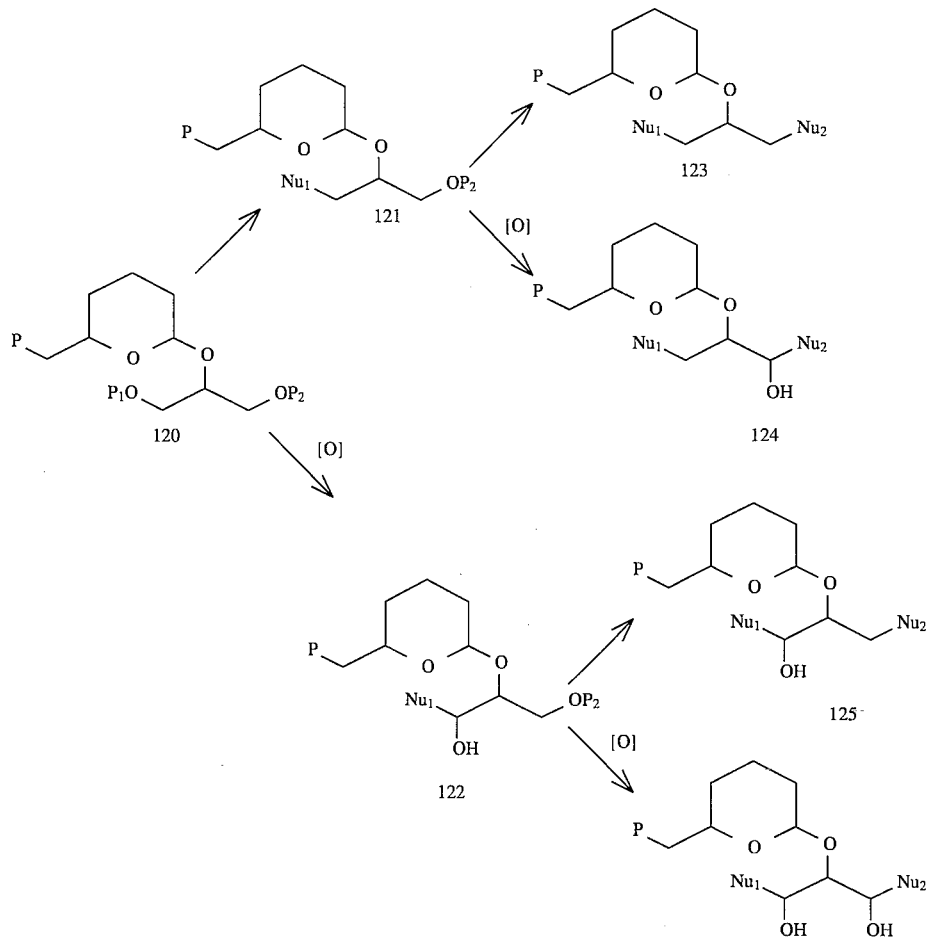

One preferred nucleophile is piperazine. Reaction of 120 where $P_1$ is nitrobenznensulfonyl and $P_2$ is phenyl with piperazine leads to structure 121 where $Nu_1$ is N-piperazyl. These derivatives are useful in the synthesis of many important compounds, such as α,β blockers.

B. Examples

Reaction Schemes XIXA and XIXB demonstrate the application of the methods of the invention to the synthesis of a glycerol-based compound. Starting with dihydropyran 130, reaction with sodium hydride and sodium chloroacetate leads to compound 131. Reaction of 131 with cyanochloromethane in DMF at 60° C. yields the cyanomethyl ester 132. This is reacted with 1-(triisopropylsilyl)-3-tosylglycerol to form compound 133. Reaction of 133 with the amine-derivatized support in DMF at 60° C. forms the support-bound structure 134. As shown in Reaction Scheme XIXB, the tosyl group is replaced with a phenoxy moiety by reaction of 134 with sodium phenoxide in DMF at 65° C. to make 135. Reaction of 135 with terra-butylammonium flouride (TBAF) followed by reaction with p-nitrophenylsulfonylchloride in pyridine and then reaction with tertbutylamine forms 136. Clevage from the support and formation of the desired glycerol derivative, 1-(tert-butylamonium)-3-phenoxyglycerol chloride, 137 is achieved by reaction of 136 with butyl alcohol and HCl.

REACTION SCHEME XIXA

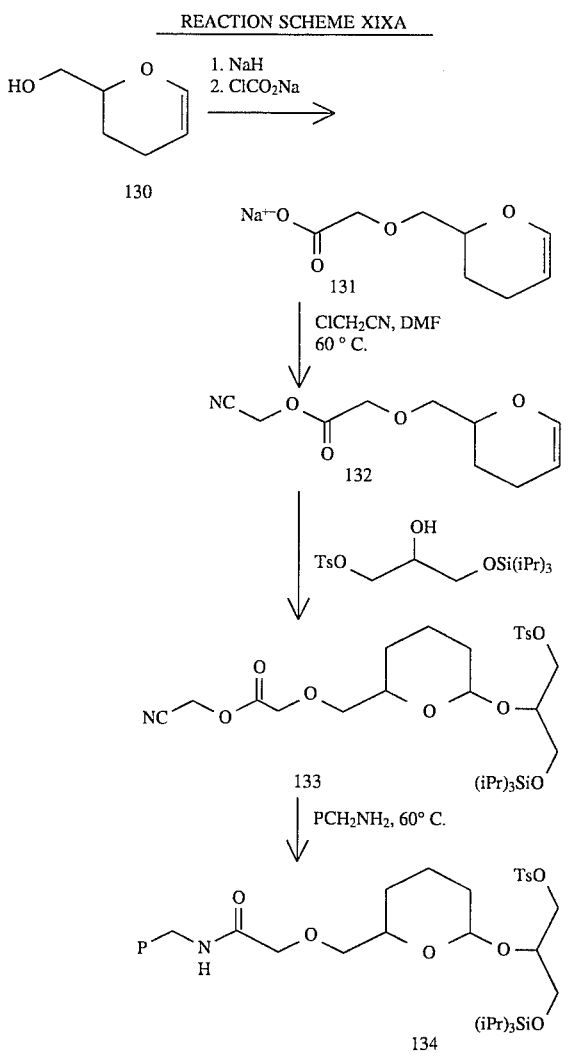

REACTION SCHEME XIXB

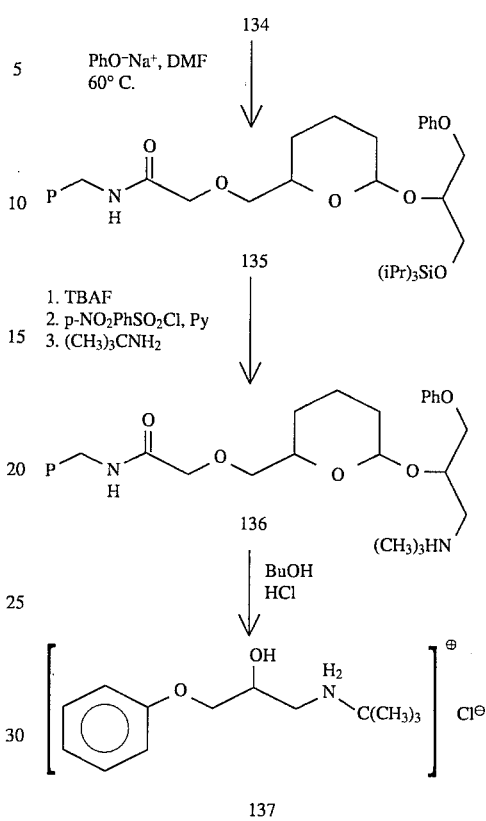

One preferred class of compounds made using the method described in Reaction Scheme XIXB are those where the phenyl ring includes a halogen substituent. It will be appreciated that such compounds can be derivatized further by employing the Suzuki reaction described above. Another preferred class of compounds which can be made using transformations just described include the aspartic acid protease inhibitors, shown generally below at left. This compound have sidechains ($R_2$, $R_3$ and $R_5$) identical to the corresponding peptide (shown at right), but the compound at left is not a polymer and does not have the repeating backbone structure of the corresponding peptide.

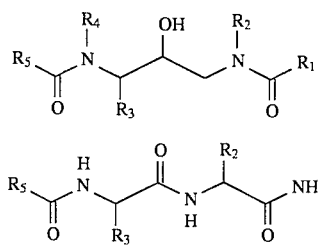

The synthesis of the inhibitor is shown below in Reaction Scheme XX.

REACTION SCHEME XX

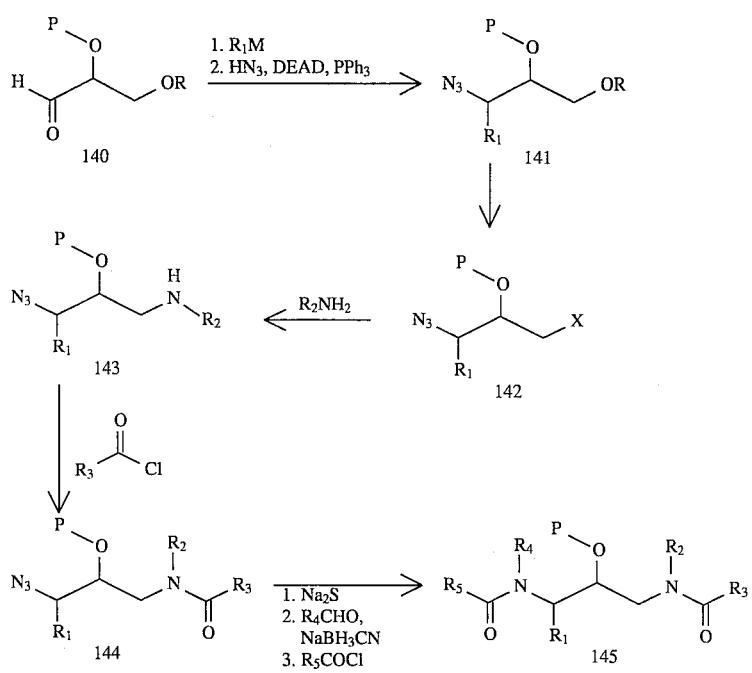

Starting from the support-bound aldehyde 140, reaction with an organometallic reagent carrying $R_1$, such as $R_1MgBr$, forms the corresponding addition product, which is an alcohol. Reaction with azide using Mitsonobu conditions forms the corresponding azide 141. Conversion of the —OR group to a leaving group such as halogen 142, followed by displacement with $R_2NH_2$ forms 143. Reaction with an acyl chloride bearing $R_3$ to make 144, reduction of the azide, reaction with $R_4CHO$ and sodium cyanoborohydride, and $R_5COCl$ yield the desired product 145. These reactions are well-known in the art.

VI. Methods of Forming Libraries of Monomers

Thus, from the above descriptions it will be seen that the present invention provides a method of synthesizing a library of monmeric compounds having a plurality of chemical structures on a solid substrate. The method comprises the steps of binding a amino acid monomers to a solid support and reacting the monomers with a plurality of reagents under conditions effective to create a plurality of chemical structures. In one preferred embodiment, the step of reacting the monomers and reagents includes exposing the monomers to the reagents simultaneously. Below, several preferred methods of solid phase synthesis are discussed in detail.

A. Pin Based Synthesis

Preferably, the techniques described above are used to synthesize more than 3, preferably more than 5, preferably more than 10, more preferably more than 50, more preferably more than 100, and more preferably more than 1,000 different molecules simultaneously. FIG. 1 illustrates apparatus for preparation of the various compositions described herein. Such apparatus is described in greater detail in association with the synthesis of peptides in Geysen et al., *J. Immun. Methods* (1987) 102:259–274, incorporated herein by reference for all purposes. The method utilizes a substrate 201 having a plurality of pins or other extensions 204. The pins are each inserted simultaneously into individual reagent containers 206 in tray 208. It will be recognized that only a few pins/trays are shown in FIG. 1, but in most embodiments a large array of such pins/containers will be provided. In a common embodiment, an array of 96 pins/containers is utilized.

Each tray is filled with a particular reagent for coupling in a particular chemical reaction on an individual pin. Accordingly, the trays will often contain different reagents. Since the chemistry disclosed herein has been established such that a relatively similar set of reaction conditions may be utilized to perform each of the reactions, it becomes possible to conduct multiple chemical coupling steps simultaneously.

Figure 2:
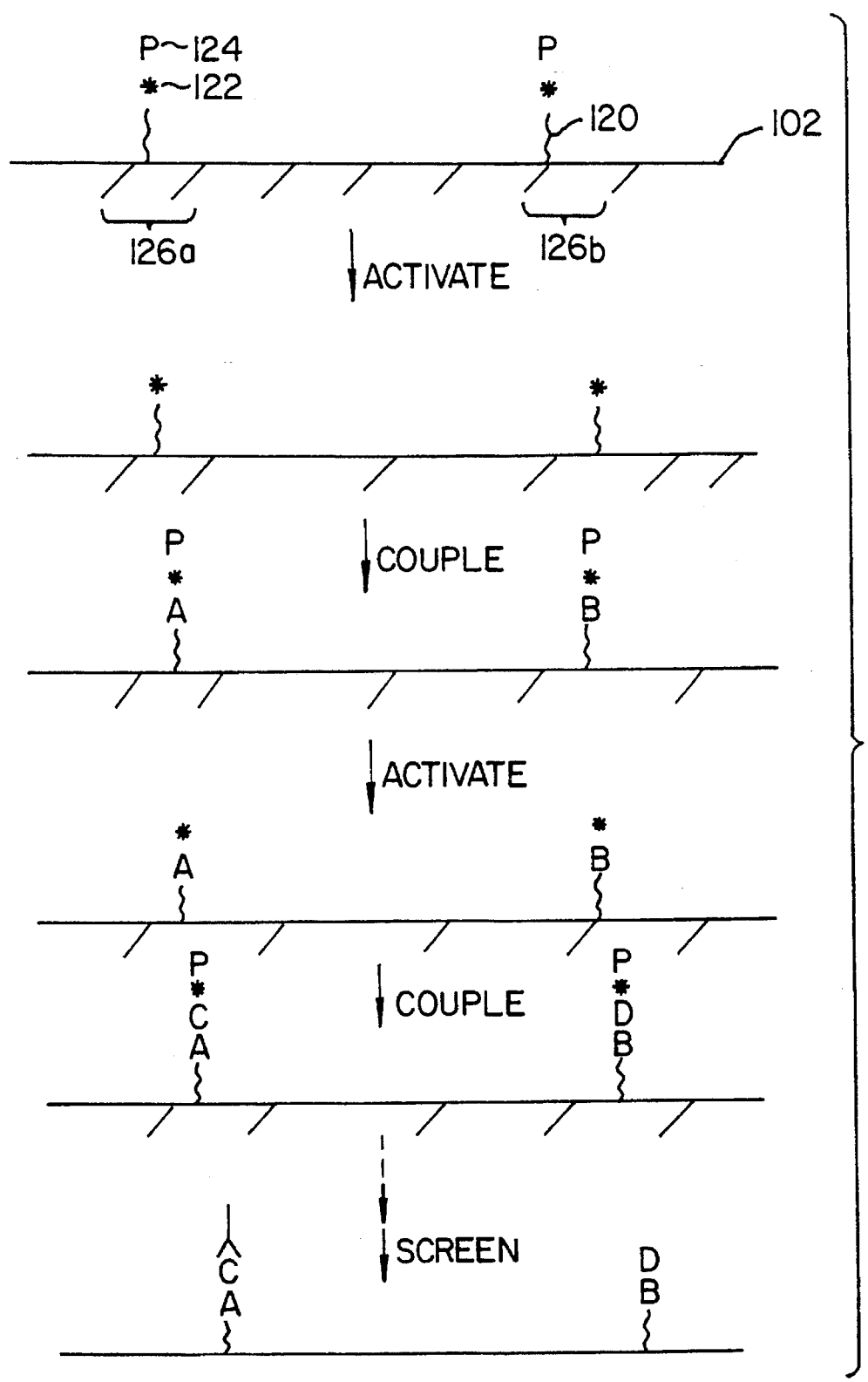
FIG. 2 illustrates the method of forming diverse molecules according to the methods herein.

FIG. 2 illustrates the method utilized to form the various molecules discussed herein. As shown, in the first step of the process the invention provides for the use of substrate(s) on which the chemical coupling steps are conducted. As shown therein, the substrate is optionally provided with linker molecules 220 having active sites 222. In the particular case of benzodiazepines, for example, the linker molecules may be selected from a wide variety of molecules such as HMPA. The active sites are optionally protected initially by protecting groups 224. Among a wide variety of protecting groups are materials such as Fmoc, BOC, t-butyl esters, t-butyl ethers, and the like. Various exemplary protecting groups are described in, for example, Atherton et al., *Solid Phase Peptide Synthesis,* IRL Press (1989), incorporated herein by reference. In some embodiments, the linker molecule may provide for a cleavable function by way of, for example, exposure to acid or base.

The substrate includes a plurality of spatially addressable regions such as 226a and 226b. In the particular embodiment described herein, the regions 226a and 226b are pins extending from a common substrate.

In an initial step, one or more of the regions of the substrate are activated by removal of the protecting groups. It will be recognized that both regions may be activated in some embodiments simultaneously, or the regions may be individually activated. In the case of pin-based techniques, the regions may be activated by, for example, dipping selected pins in trays having an appropriate activating agent. In the particular case of acid labile protecting groups, such activating agents may include acid, while in the case of base labile groups, such agents may include base.

Thereafter, a first portion of a molecule to be synthesized is added to the support. In the particular case of benzodiazepine synthesis, for example, the first portion will be a substituted amino benzophenone in many cases. The first portion of the molecule to be synthesized is provided with an active site, such as an amino site in the case of amino benzophenones, which is preferably protected by an appropriate protecting group. The protecting group on the first portion of the molecule to be synthesized will in some cases be the same as the protecting group on the substrate, although in many cases a different protecting group will be utilized. Appropriate protecting groups for an amino group on an amino benzophenone are described in Atherton et al., previously incorporated herein by reference. In the case of pin-based synthesis the first portion of the molecule to be added is coupled by way of dipping the appropriate pins in an a tray having containers with the appropriate material to be added. In most cases, the various regions will be coupled to different molecules, represented by A and B in FIG. 2. For example, in the case of benzodiazepine synthesis, A and B will be represented by different amino benzophenones.

A and B will be coupled at the same time in many embodiments, although the regions 226a and 226b may, alternatively, be activated at different times, in which case the entire surface may be washed with, for example, A after region 226a is activated followed by activation of region 226b and washing of both regions with B. Since A and B are also protected, undesirable coupling will not take place in the regions where it is not desirable. It will be recognized by those of skill in the art that additional steps of washing and the like will be desirable in some embodiments, but are not illustrated in FIG. 1 for the sake of simplicity.

Thereafter, an additional activation step is conducted by removal of the protecting groups from the molecule portions A and B either at the same or different times. In the case of Fmoc protecting groups, for example, such activation will be conducted by exposure to, for example, a basic solution. Thereafter, an additional coupling step is performed in which molecule portions C and D are added to the molecule portions A and B respectively. In the particular case of benzodiazepine synthesis, for example, the molecule portions C and D will be represented by activated acyl fluoride derivatives of Fmoc-protected natural or unnatural amino acids.

Thereafter, optional additional coupling steps, cyclization steps, or the like are performed on the growing molecules. For example, in the case of benzodiazepines, the additional steps will normally include removal of the Fmoc protecting group using base followed by exposure to 5% acetic acid in DMF for cyclization, followed by alkylation of the amide nitrogen.

Since a wide array of substituted amino benzophenone groups, and a wide array of acyl fluoride amino acid derivatives are readily available, the synthesis technique herein results in an array of materials on the substrate that are at known locations on the substrate and which may be effectively used in screening studies to determine which of the synthesized materials show significant affinity for a receptor or receptors of interest. As shown in FIG. 2, receptor affinity is studied by exposing the substrate to the receptor or receptors of interest, and determining where the receptor has bound to the substrate. In some embodiments, the location of the receptor on the substrate may be conveniently located by labelling the receptor with an radioactive or fluorescent label, and scanning the surface of the substrate for the presence of the receptor. In some embodiments, the receptor of interest may be unlabelled, but later exposed to a second receptor that is labelled and known to be complementary to the receptor of interest. As indicated in FIG. 2, the receptor will bind to the molecules that are complementary to the receptor (such as AB in FIG. 1) while it will not bind to other molecules on the substrate (such as BD in FIG. 1). Accordingly, the present method provides an effective way to identify ligands that are complementary to a receptor.

In alternative embodiments, the synthesized benzodiazepine is cleaved and screened in solution, using the methods described in detail above.

B. Bead Based Synthesis

Figure 3:
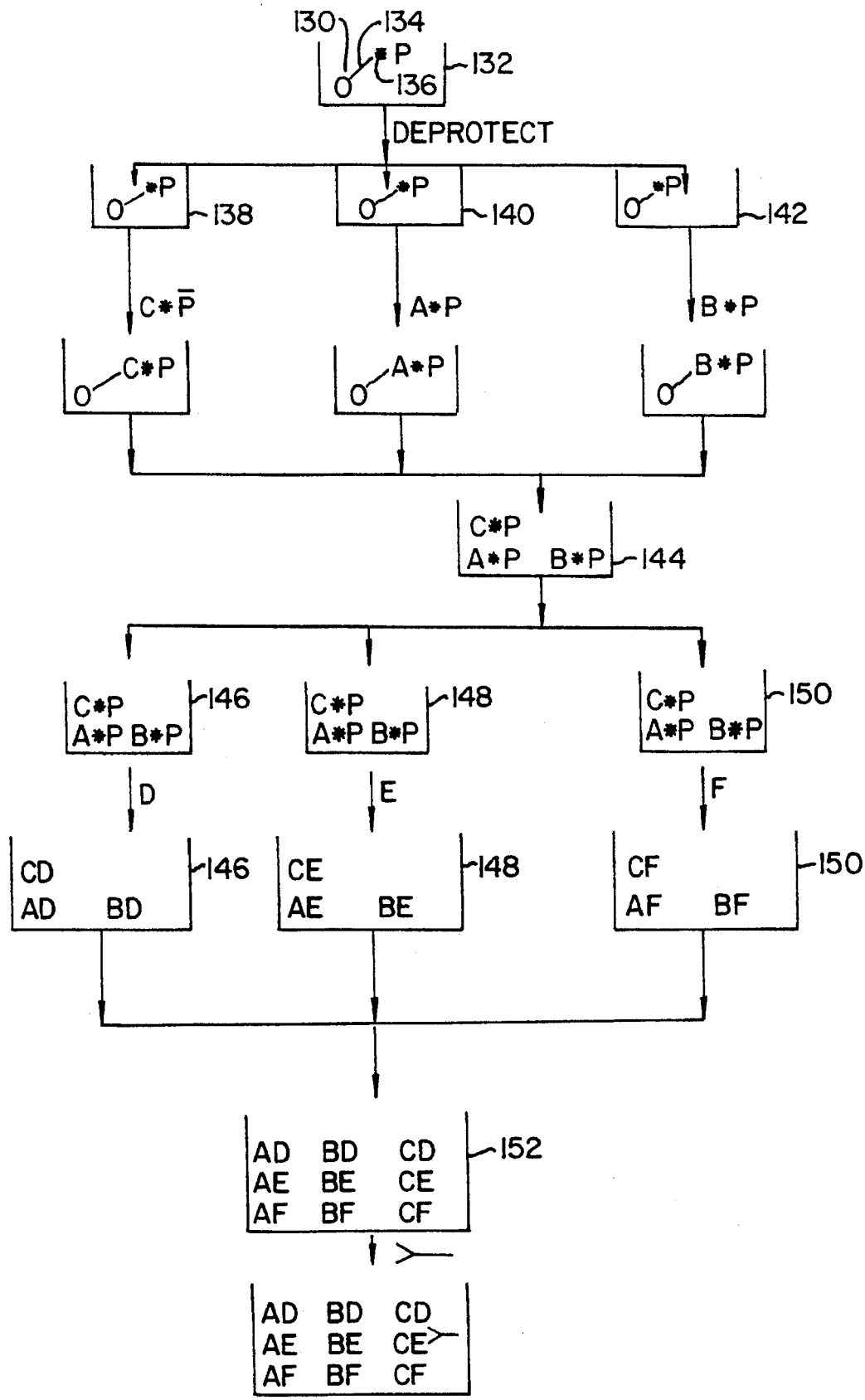
FIG. 3 illustrates bead based synthesis.

In an alternative embodiment of the invention a similar series of chemical coupling/cyclization steps are conducted, except that the synthesis steps are conducted on discrete solid substrates such as beads. A general approach for bead based synthesis in conjunction with peptides is described in Lam et al., "A new type of synthetic peptide library for identifying ligand-binding activity," *Nature* (1991) 354:82–84, incorporated herein by reference for all purposes, and further described in PCT application no. 92/00091 and Houghten et al., "Generation and use of Synthetic Peptide Combinatorial Libraries for Basic Research and Drug Discovery," *Nature* (1991) 354:84–86, and also incorporated herein by reference for all purposes FIG. 3 illustrates the synthesis of molecules such as benzodiazepines on such beads. A large plurality of beads 230 are suspended in a suitable carrier (such as water) in a container 232. Although only a single bead is illustrated in FIG. 3 for the purposes of simplifying the illustration, it will be recognized that a large number of beads are utilized. The beads are provided with optional linker molecules 234 having an active site 236. The active site is protected by an optional protecting group P.

In a first step of the synthesis, the beads are divided for coupling into containers 238, 240, and 242. The protecting groups are then removed and a first portion of the molecule to be synthesized is added to the various containers. For example, in the case of benzodiazepines, the first portion of the molecule to be synthesized may be various Fmoc protected substituted amino benzophenones, represented herein by A, B, and C. The first portion of the molecules to be synthesized comprise active sites protected by a protecting group P.

Thereafter, the various beads are appropriately washed of excess reagents, and remixed in container 244. Again, it will be recognized that by virtue of the large number of beads utilized at the outset, there will similarly be a large number of beads randomly dispersed in the container 244, each having a particular first portion of the monomer to be synthesized on a surface thereof. For the purpose of simplifying the illustration, the beads and linker molecules are not shown in the bottom portion of FIG. 3.

Thereafter, the various beads are again divided for coupling in containers 246, 248, and 250. The beads in container 246 are deprotected and exposed to a second portion of the molecule to be synthesized, represented by D, while the beads in the containers 248 and 250 are coupled to molecule portions E and F respectively. In the particular case of benzodiazepine synthesis, molecule portions D, E, and F would be, for example, acyl fluoride derivatives of natural or natural amino acids. Accordingly, molecules AD, BD, and CD will be present in container 246, while AE, BE, and CE will be present in container 248, and molecules AF, BF, and CF will be present in container 250. Each bead, however, will have only a single type of molecule on its surface. In the particular embodiment shown in FIG. 3, all of the possible molecules formed from the first portions A, B, C, and the second portions D, E, and F have been formed.

Optionally, the beads are then recombined into container 52. Additional steps such as cyclization, and the like are conducted on the completed polymer molecules.

Thereafter, the beads are exposed to a receptor of interest. In a preferred embodiment the receptor is fluorescently or radioactively labelled. Thereafter, one or more beads are identified that exhibit significant levels of, for example, fluorescence using one of a variety of techniques. For example, in one embodiment, mechanical separation under a microscope is utilized. The identity of the molecule on the surface of such separated beads is then identified using, for example, NMR, electron impact mass spectrometry, or the like.

In alternative embodiments the identity of the molecule that is complementary to the receptor is determined with respect to the "bin" or container in which the labelled receptor is located. For example, by exposing the molecules in containers 246, 248, and 250 to the labelled receptor, the identity of one terminal portion of the molecule may be identified. For example, if fluorescence is noted after exposure to the molecules in container 246, but not 248 or 250, it is readily determined that the terminal molecule that produces a complementary receptor is "D." Thereafter, one will synthesize all of the molecules AD, BD, and CD in separate containers. The identity of the other terminal portion of the molecule can then be determined by identifying where receptor binding is located among these molecules.

C. Light Directed Synthesis

Figure 4:
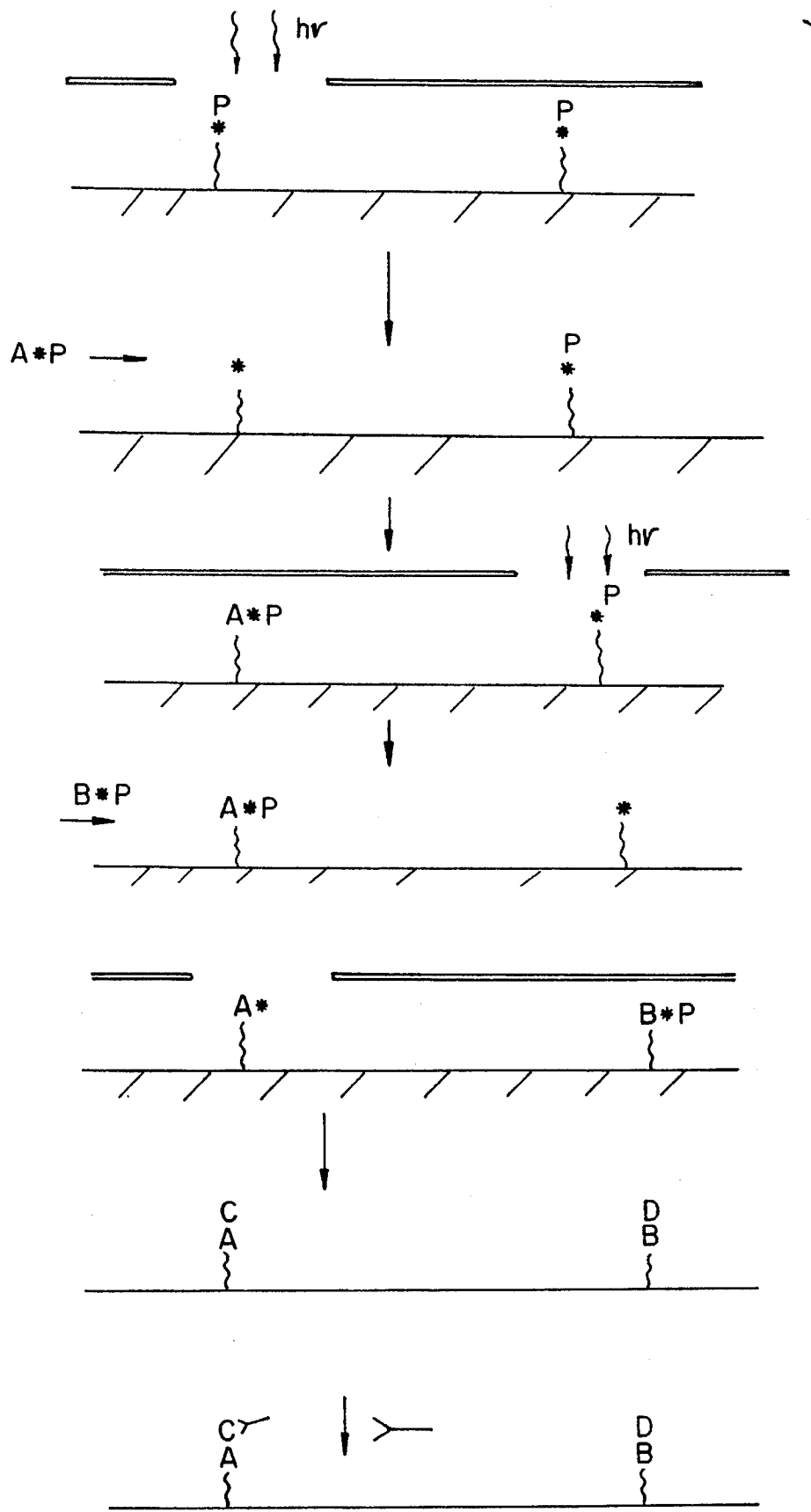
FIG. 4 illustrates light based synthesis.

In an alternative embodiment, different β-turn mimetics or other materials are synthesized on a substrate using light directed techniques as shown in FIG. 4, preferably using wavelengths of light greater than 400 nm and more preferably more than 500 nm. As shown therein, the substrate is similarly provided with protecting groups, optionally coupled to the substrate via linker molecules. In this case, the protecting groups are removable upon exposure to light. Accordingly, the protecting groups in a first selected region are removed by exposing the first selected region to light, but not exposing the second selected region to light. As illustrated in FIG. 4, this selective irradiation step may be accomplished through the use of a mask such as the masks commonly used in the semiconductor industry. Such techniques are described in greater detail in U.S. Pat. No. 5,143,854 (Pirrung et al.), incorporated herein by reference for all purposes.

Thereafter, the entire substrate or a part thereof is exposed to a first portion of the molecule to be synthesized (indicated by A in FIG. 4). In the case of benzodiazepines, the first portion of the molecule will, for example, be substituted amino benzophenones with appropriate light, base, or acid labile protecting groups. Thereafter, second regions of the substrate are exposed to light using the same or a different mask, and B is coupled to these regions. Coupling of the portions C and D follows in a similar manner, wherein C and D are representative of, for example, activated acyl fluoride derivatives of Fmoc protected amino acids.

VII. Screening

It will be appreciated that the present invention is easily extended to the screening of the library of diverse monomers described above for biological activity. Generally this embodiment requires the additional step of screening the library of compounds against a receptor and determining which of the compounds are ligands for that receptor. For example, as shown in FIG. 1, the substrate bearing the library of monomers is exposed to a receptor of interest that is appropriately labelled with, or coupled to, another receptor with a label, such as a fluorescent or radioactive label.

The substrate is then scanned to determine the location of the label. From knowledge of the composition of the molecule synthesized at each site, those molecule(s) that are complementary to the receptor can be identified.

In a related application, it will be appreciated that the arrays of compounds having biological activity constructed in accordance with the disclosure above can be produced in the form of "kits" of substrate-bound compounds. "Biological activity" is defined herein to indicate that the substance in question is capable of a physical or chemical interaction with another substance of known biological significance, e.g., binding to a known receptor. These kits may include, for example, 50 or more different compounds having biological activity. These compounds may be benzodiazepines, β-turn mimetics, prostaglandins, or glycerol derivatives as described above. Such kits may be used to screen various biological receptors of interest.

VIII. Conclusion

The above description is illustrative and not restrictive. Many variations of the invention will become apparent to those of skill in the art upon review of this disclosure. Merely by way of example a wide variety of process times, reaction temperatures, and other reaction conditions may be utilized, as well as a different ordering of certain processing steps. The scope of the invention should, therefore, be determined not with reference to the above description, but instead should be determined with reference to the appended claims along with their full scope of equivalents.

What is claimed is:

1. An array comprising a plurality of benzodiazapines at selected, known positions on a substrate wherein each of said benzodiazapines is substantially pure within each of said selected locations and has a composition different than selected other benzodiazepines on said substrate.

2. The array of claim 1, wherein said substrate comprises amino-derivatized polyethylene pins.

3. A method of synthesizing benzodiazapines and analogs thereof on a solid substrate, comprising the steps of:
   (a) coupling a first compound selected from the group consisting of an unsaturated carbocyclic compound, a unsaturated heterocyclic compound or a carbocyclic compound, to a substrate, said first compound including a first substituent selected from the group consisting of acyl halide or organometallic, and a second substituent selected from the group consisting of amino, protected amino, nitro, halogen, hydroxyl, azide, —OSO$_2$R, —OR, —SR, hydrogen, alkyl, aryl, heteroaryl, substituted alkyl, substituted aryl, substituted heteroaryl and —N=NAr where R is alkyl and Ar is aromatic;
   (b) reacting said first compound with a second compound selected from the group consisting of an unsaturated carbocyclic compound, a unsaturated heterocyclic compound or a carbocyclic compound, under conditions effective to form a ketone, said second compound including a first substituent selected from the group consisting of acyl halide or organometallic, and a second substituent selected from the group consisting of amino, substituted amino, nitro, halogen, hydroxyl, azide, —OSO$_2$R, OR, —SR, hydrogen, alkyl, aryl heteroaryl, substituted alkyl, substituted aryl or substituted heteroaryl and —N=NAr where R is alkyl and Ar is aromatic;

provided that if said first compound includes an acyl halide substituent, then said first substituent of said second compound is organometallic and vice versa, and further provided that one of said second substituents of either of said compounds must be selected from the group consisting of amino, substituted amino, nitro, halogen, hydroxyl, azide, —OSO$_2$R, —OR, —SR, and —N=NAr where R is alkyl and Ar is aromatic and be located adjacent said first substituent;

(c) forming a free amine;

(d) coupling an amino acid derivative to said free amine to form an amide; and (e) cyclizing said amide to form support-bound benzodiazapines or benzodiazapine analogs.

4. The method of claim 3, wherein said organometallic substituent is selected from the group consisting of trialkyltin or triaryltin.

5. The method of claim 4, wherein said first compound is a substituted aryltrimethyltin, and said second compound is a substituted aryl chloride.

6. The method of claim 6, wherein said amino acid derivative is an acyl fluoride amino acid derivative.

7. The method of claim 3, wherein said substrate comprises amino-derivatized pins.

8. The method of claim 3, further comprising the step of cleaving said benzodiazapine from said support.

9. The method of claim 3, further comprising the step of reacting said amide with a compound having the formula RX, wherein R is selected from the group consisting of alkyl, aryl, or heteroaryl, and X is halogen.

* * * * *